(12) United States Patent
Horowitz et al.

(10) Patent No.: US 8,148,085 B2
(45) Date of Patent: Apr. 3, 2012

(54) DONOR SPECIFIC ANTIBODY LIBRARIES

(75) Inventors: Lawrence Horowitz, Atherton, CA (US); Ramesh Bhatt, Belmont, CA (US); Arun K. Kashyap, San Francisco, CA (US)

(73) Assignee: Sea Lane Biotechnologies, LLC, Atherton, CA (US)

( * ) Notice: Subject to any disclaimer, the term of this patent is extended or adjusted under 35 U.S.C. 154(b) by 0 days.

(21) Appl. No.: 11/853,795

(22) Filed: Sep. 11, 2007

(65) Prior Publication Data

US 2008/0152657 A1   Jun. 26, 2008

Related U.S. Application Data

(63) Continuation-in-part of application No. 11/748,980, filed on May 15, 2007, now abandoned.

(60) Provisional application No. 60/800,787, filed on May 15, 2006, provisional application No. 60/855,679, filed on Oct. 30, 2006.

(51) Int. Cl.
G01N 33/53 (2006.01)
C07H 21/04 (2006.01)

(52) U.S. Cl. ................................ 435/7.1; 536/23.53

(58) Field of Classification Search .................. None
See application file for complete search history.

(56) References Cited

U.S. PATENT DOCUMENTS

| | | | | |
|---|---|---|---|---|
| 5,925,559 | A * | 7/1999 | Collins et al. | 435/252.33 |
| 6,169,175 | B1 * | 1/2001 | Frace et al. | 536/23.72 |
| 6,607,878 | B2 * | 8/2003 | Sorge | 506/4 |
| 2002/0054882 | A1 | 5/2002 | Okuno et al. | |

FOREIGN PATENT DOCUMENTS

| | | |
|---|---|---|
| EP | 1 647 600 A | 4/2006 |
| WO | WO 84/00687 | 3/1984 |
| WO | WO 96/07754 | 3/1996 |
| WO | WO 00/57183 A | 9/2000 |
| WO | WO 02/46235 | 6/2002 |
| WO | WO 02/061071 | 8/2002 |
| WO | WO 03/052101 A | 6/2003 |
| WO | WO 03/078600 | 9/2003 |
| WO | WO 2005/042759 A | 5/2005 |
| WO | WO 2007/031550 A | 3/2007 |
| WO | WO 2007/052242 | 5/2007 |
| WO | WO 2007/089753 | 8/2007 |
| WO | WO 2007/134327 A | 11/2007 |
| WO | WO 2008/028946 | 3/2008 |
| WO | WO 2008/118970 | 10/2008 |

OTHER PUBLICATIONS

Hammond, P.W., et al., "In Vitro Selection and Characterization of Bcl-XL-Binding Proteins from a Mix of Tissue-Specific mRNA Display Libraries," The Journal of Biological Chemistry, 276(24): 20898-20906, 2001.

Kashyap, Arun K., et al., "Combinatorial Antibody Libraries from Survivors of the Turkish H5N1 Avian Influenza Outbreak Reveal Virus Neutralization Strategies," The National Academy of Sciences of the USA, 105(16): 5986-5991, 2008.

Kim, Sang Jick, et al., "Neutralizing Human Monoclonal Antibodies to Hepatitis A Virus Recovered by Phage Display," Virology, 318: 598.607, 2003.

Mao, Shenlan, et al., "Phage-Display Library Selection of High-Affinity Human Single-Chain Antibodies to Tumor-Associated Carbohydrate Antigens Sialyl Lewisx and Lewisx," Proc. Natl. Acad. Sci. USA, 96: 6953-6958, 1999.

Qui, Fang, et al., "DNA Sequence-Based 'Bar Codes' for Tracking the Origins of Expressed Sequence Tags from a Maize cDNA Library Constructed Using Multiple mRNA Sources," Plant Physiology, 133: 475-481, 2003.

Throsby, Mark, et al., "Isolation and Characterization of Human Monoclonal Antibodies from Individuals Infected with West Nile Virus," Journal of Virology, 80(14): 6982-6992, 2006.

Ada, et al., "The Immune response to influenza infection", Current topics in Microbiology and Immunology, vol. 128, pp. 1-54, (1986).

Colman. et al., "Structure or the catalytic and antigenic sites in influenza virus neuraminidase", Nature, vol. 303, pp. 41-44, (1983).

Couch, et al., "Immunity to influenza in man", Ann. Rev. Microbiology, vol. 37, pp. 529-549, (1983).

Gocnik, et al., "Antibodies specific to the IIA2 glycopolypeptide of influenza. A virus haemagglutinin with fussion-inhibition activity contribute to the protection of mice against lethal infection", Journal of General Virology, vol. 88, Part 3., pp. 951-955, (2007).

Goudsmit, Japp, Presentation at 5$^{th}$ International Bird Flu Summit, Sep. 27, 2007, URL link http://investors.crucell.com/C/132631/present 2007 v2.html.

Goudsmit, Japp, Presentation at Symposium for 10$^{th}$ Anniversary of Inflexal V, Apr. 26, 2007.

Govorkova, et al., "Immunization with reverse-genetics-produced H5N1 influenza vaccine protects ferrets against homologous and heterologous challenge", Efficacy of H5N1 vaccine in ferrets, pp. 159-167, (2006).

Hanson, et al., "Passive immunoprophylaxis and therapy with humanized monoclonal antibody specific for influenza A H5 hem agglutinin in mice", Respiratory Research, 7:126, pp. 1-10, (2006).

Knappik, et al., "Fully synthetic human combinatorial antibody libraries (HuCAL) based on modular consensus frameworks and CDRs randomized with trinucleotides", Journal of Molecular Biology, 296(1): 57-86 (2000).

Kong, et al., "Successful treatment of avian influenza with convalescent plasma", Hong Kong Med., vol. 12, No. 6, p. 489, (2006).

Law, et al., "Broadly neutralizing antibodies protect against hepatitis C virus quasispecies challenge", Nature Medicine, vol. 14, No. 1, pp. 25-27, (2008).

(Continued)

Primary Examiner — Stacy B. Chen
(74) Attorney, Agent, or Firm — Jeffery P. Bernhardt; Arnold & Porter LLP

(57) ABSTRACT

The present invention concerns donor-specific antibody libraries derived from a patient donor who has suffered from, or is suffering from one or more diseases discussed herein. The present invention also concerns the method of making and using the donor-specific antibodies. The present invention further concerns the neutralizing antibodies obtained from the donor-specific antibody libraries and the methods of using these antibodies for the prevention/treatment of human disease.

18 Claims, 31 Drawing Sheets

OTHER PUBLICATIONS

Lerner, et al., "Manufacturing immunity to disease in a test tube: the magic bullet realized", Angew. Chem. Int. Rd., 45, pp. 8106-8125, (2006).

Lu et al. "Passive immunotherapy for influenza A H5N1 virus infection with equine hyperimmune globulin F(ab')2 in mice", Respiratory Research, 7: 43 (7 pages), (2006).

Luke, et al., "Meta-analysis: Convalescent blood products for Spanish influenza pneumonia: A future H5N1 treatment?", Annals of Internal Medicine, 145(8): 599-609, (2006).

Okuno et al. "Protection against the mouse-adapted A/FM/1/47 strain of influenza A virus mice by a monoclonal antibody with cross-neutralizing activity among H1 and H2 strains", J. Virology, 68(1): 517-520, (1994).

Okuno, et al., "A common neutralizing epitope conserved between hemagglutinins of influenza, a virus of H1 and H2 strains", Journal of Virology, vol. 67, No. 5, pp. 2552-2558, (1993).

Oner, et al., "Avian influenza A (H5N1) infection in eastern Turkey in 2006", The New England Journal of Medicine, vol. 355, No. 21, pp. 2179-2185, (2006).

Palese, et al., "Orthomyxoviridae: The viruses and their replication", Fields Virology, vol. 2, pp. 1647-1654, (2008).

Rimmelzwaan, et al., "Influenza virus subtype cross-reactivities of haemagglutination inhibiting and virus neutralising serum antibodies induced by infection or vaccination with an ISCOM-based vaccine", Vaccine 17(20-21): 2512-2516 (1999).

Shahzad et al. "Passive immunization against highly pathogenic Avian influenza virus (AIV) strain H7N3 with antiserum generated from viral polypeptides protect poultry birds from lethal viral infection", Virology Journal, 5:144 (6 pages), (2008).

Simmons, et al., "Prophylactic and therapeutic efficacy of human monoclonal antibodies against H5N1 influenza", PLOS Medicine, vol. 4, Issue 5, pp. 928-936, (2007).

Smirnov, et al., "An epitope shared by the hemagglutinins of II1, 112, II5, and II6 subtypes of influenza A virus", Acta Virologica, 43(4): 237-244 (1999).

Smirnov, et al., "Prevention and treatment of bronchopneumonia in mice caused by mouse-adapted variant of avian H5N2 influenza A virus using monoclonal antibody against conserved epitope in the HA stem region", Arch Virol., 145(8):1733-1741, (2000).

Stephenson, et al., "Cross-reactivity to highly pathogenic avian influenza II5N1 viruses after vaccination with Nonajjuvanted and MF59-adjuvanted influenza A/Duck/Singapore/97 (H5N3) vaccine: A potential priming strategy", The Journal of Infectious Diseases, 191(8): 1210-1215, (2005).

Throsby, et al., "Heterosubtypic neutralizing monoclonal antibodies cross-protective against II5N1 recovered from human IgM memory B cells", PLOS One, vol. 3, Issue 12, pp. 1-15, (2008).

Xu, et al., "Combinatorial surrobody libraries", Proceedings of the national academy of sciences, vol. 105, No. 31, pp. 10756-10761, (2008).

Zhang et al., "Improved breadth and potency of all HIV-1-neutralizing human single-chain antibody by random mutagenesis and sequential antigen panning", Journal of Molecular Biology, 335: 209-219, (2004).

Zhou, et al., "Treatment with convalescent plasma for influenza A (II5N1) infection", The New England Journal of Medicine, 357:14, pp. 1450-1451, (2007).

* cited by examiner

H3 DESTINATIONAL EXAMPLE
CDR H3

| 2SD4 CODONS | T ACN | K AAR | A GCN | S TCN | Y TAY | L CTN | S AGY | T ACN | S AGY | S AGY | L CTN | D GAY |
|---|---|---|---|---|---|---|---|---|---|---|---|---|
| DEGENERATE OLIGO | | | | | | | | | | | | |
| COCONS | RCN | MRN | GSN | WYN | NTA | YTN | AGY | ACN | AGY | AGY | YTN | GAY |
| Raptiva | GCN | CGN | GGN | ATH | YTA | YTN | WRY | RSN | NAS | NWR | TTY | GAY |
| | A | R | G | I | Y | F | | T | T | Y | F | D |

DESTINATIONAL COPRODUCTS

| | AAY | ACN | ACN | | TTR | AYA | AGY | AGR | AGR | AAY | TTR | |
| | CAY | TTY | TTY | | L | AYN | | AGR | | NGY | L | |
| | CAR | TTR | TTR | | | TGY | | R | | TGY | | |
| | AGY | ATG | ATG | | | C | | GCN | | C | | |
| | S | M | M | | | | | A

| Positions from 241 till 300 | | |
|---|---|---|
| consensus | VPEIGARPKVNGQSGRMDFYWTLLKPGDTITFESNGNLIAPRYAYKLIKGGPSGIEYNGK |  |
| AAA43678 | T.D.AT......LGS..E.S...DMW..N...T....E.GF.IS.R.----SS |  |
| AAA79775 | .V.V....Q......H...VQ...N....SD..G...SRVS..T-----.R |  |
| AAA96134 | S..SP.........A..I..H.M..D....V..TF..AF..DR.TF.RSNA.------ |  |
| AAC40998 | .SP.....Q......I..H.LM.N...V....SF..AF..DR.SF.R----------- |  |
| AAD17229 | T.....A....RD.A....NY......E.......AT...W..FA.NR.S--------S |  |
| AAD21159 | ....AT.........E.F..I....N.A.N.....F....E..IV.K.----------- |  |
| AAF99711 | ...D...S....L.R....VS......IVE..L.V.NTI......GH...NNQ-----DS |  |
| AAK51718 | I.N...S....W.R.L.S.ISI....IV....VLVIN......GYF.MRT-------K. |  |
| AAX78820 | S.....A....R..I.Y....SV..E.LNV......W.....FTSSN-------N. |  |
| ABB87356 | EL...T..IG-D..RSW.KI..H.MH..ER.M....G.L..-I.EKY----------.T |  |
| BAA14334 | Q.N..P..L.R..Q....Y..GI..R.E.LKIRT....EFG..L..E---------SY |  |
| BAA14336 | T...NT..R....A...T...KIV...ES.....AFL....F-E..VSV-------N |  |
| BAA14337 | K.N..P..L.R..Q....Y..AV...Q..VKIQT....E.GH..T.K----------SH |  |
| BAA14338 | KL.T.V..GY...RSW.KI..S.IH..EM....GFL...G.-I.EEY.----------- |  |
| CAB95856 | K.V..P..L....LQ..I.Y...SV....Q.LRVR.....W.GH-VLS.----------SH |  |

FIG. 7E

```
Positions from 301 till 360
consensus   GRIIQSEDLPIGANCNTKCQTPGGAINTSKPFQNISPLTIGECPKYVKSGSLKLATGLRN
AAA43678    -.MKT-EGTLE-..E....L.....TL.H.VH.........EK.V...........
AAA79775    DLG....-EAL.DNS.ES.FWR..S.....KL....L.R.V.Q.....NQR..L...M.
AAA96134    SLG....-.AQ.DES.EGE.FYS..T....SPL....DSRAV.K....R..QS..P.L.MK
AAC40998    SMG....-.EVQVD..EGD.YHS.T.LS.L.......NSR.V....R..QE..L..MK
AAD17229    -....T-..A.VH-D......H....S.L....H.V.......R.TK.RM.....
AAD21159    T-..MK.-E.EY..-........M..H.........H.......NR.V.....
AAF99711    ST.LNT-AI...-S.VS..H.DK.SLS.T......RIAV.D..R.....Q....M.
AAK51718    SS.MR..-.A..D-T.ISE.I..N.S.PND.....VNKI.Y.A.......QNT......
AAX78820    .AVFK.-N...E-..DAV...VA..LR.N.T....V....W......D..R.....
ABB87356    .F..-GIRMA-K.....SM.GV..N.T....ERNAL.D......H...Q.......
BAA14334    ..N..I..-..........YA...S.......A.RHYM.........KA..R.V...
BAA14336    KLFR.-E.N.E-S.S.....EI.G....N.S.H.VHRN..D.....NVK.......
BAA14337    .LKN-N..M.-Q.V.E..LNE.VM....T.KHY.K........IP....H...
BAA14338    .F..-RIRMS-R.......SV.G..NRT........DKNAL.D....I...Q.....
CAB95856    .LKT-..KG...VVQ...EK.GL.STL..H...KYAF.T....RVN......V...
```

FIG. 7F

```
Positions from 361 till 420
consensus  VPEIIERRRKSRGLFGAIAGFIEGGWPGLIDGWYGFHHQNAQGTGIAADKKSTQKAIDQI
AAA43678   ..Q.......-.................Q.M.....Y..S.D..S.Y....E....F.G
AAA79775   ...VVQ---G..................E.MV....R.........Q....Y..A...
AAA96134   ...K.R---T..................E................T....Y..A...
AAC40998   ...PK---G..................E..V....R.........Q.T....Y..S...
AAD17229   I..S.-Q-I..................T.M.....Y........E.T....Y....G.
AAD21159   T.QR-..K..................Q.MV....Y..S.E..S.Y....Q....N...
AAF99711   I..K-A-I.....................Q....Y..S.E..S.Y....QE....GV
AAK51718   ...K-Q---T..................E.M....R..SE....T....L...A.N..
AAX78820   ...QA---T..................T.M....Y..E.S....Q....L...A...
ABB87356   ..S.-G---E..................E.........E............E..G.
BAA14334   T.SV-..-P..................S.M....Q...S.........A....S...
BAA14336   ..A.-A-I.....................S.SE....M....Q....E....E..K.
BAA14337   ..QV-Q-I--D...................Q.RDEE........E........R..NM
BAA14338   ..A.-S---N...................Q...E......E....E......
CAB95856   ..AR-S-I.....................Q..S.D.V.M....RD....K.
```

FIG. 7G

```
Positions from 421 till 480
consensus TNKVNNIIEKMNTQFEAIDHEFSEVEKRINNLNKKVDDGFTDIWSYNAELLVLLENQHTL
AAA43678  ..............SV............................................
AAA79775  .G.L.RL.......T......E...S.ES...T.HQ.G.VINWTK.SI..T....AM..ER..I
AAA96134  .G.L.RL.......T..K...L...N......T...QQ.G.VINWTR.SL.E........
AAC40998  .G.L.RL.......T.Q....L...N......T...Q..G.VINWTR.SL.EM...AM..ER..I
AAD17229  ..............SV...........T.VGK..NNL.R...E........L.T.........
AAD21159  .............S..N............VGR..NNL.R...E.....ME..L.V.T..M..ER..
AAF99711  NG.L.RL.......T..DKYHQ.EK...EQ..G..QD.ENY.E.TKI.L...........A..I
AAK51718  NG.L.RV.......T..EK.HQ.EK...EQ..G..QD.E.Y.E.TKI.L...........A..I
AAX78820  ..............S..D..........V..........NL.R.VD...RME..L.V.T....ER..
ABB87356  ..T..I..........GNTDS.RG....NQ........M.ADR...AV........K....DR..
BAA14334  ............VD......RE...VVN..........MI.D.I..QIE.L.A....I....K
BAA14336  ....S.......VDR.....N....SVQ..........Q.S.H...SVV......Q....EK..
BAA14337  Q.L........V.D.......K...VVN...........MI.S.I...QI....A...K....K
BAA14338  .T.I..........D......GNYDS.RG..........M.ADRI..AV........K....DK..
CAB95856  .S............VD.....K.Y.I..........T.L.MI.N.I..QIQ.V.A........K
```

FIG. 7H

```
Positions from 481 till 540
consensus  DLHDSNVKNLYEKVRRQLRDNAEDDGNGCFEIYHKCDDECMESIRNGTYDHPEYREESKL
AAA43678   .F..........D...M.....VKEL.....F.............N.VK....Y.K.E...
AAA79775   .MA..EML....R..K...Q..E..K.....F..T..........N........SQ..AL.
AAA96134   .A...EMNK...R.....E...E..T.....F.R...Q.........N.T...Q.ALQ
AAC40998   .A...EMNK...R.....E...E..T.....F.......D.A....N.....SK...AIQ
AAD17229   .F.......R........KS..KEI.....F...........A....V.....Y.K.S...
AAD21159   .F..........D...L.....KEL.....F............N......VK....Y.Q.S..AR.
AAF99711   .VT..EMNK.F.R.....E...K........F.....NN..I......DI..D.AID
AAK51718   .T...EMNK.F...T...E...M........K.....NA..I......DV..D.ALN
AAX78820   .........A........KS..K.L.....FW........IN.VK....Y..QD...
ABB87356   .A.......H.Q.K.A..KN..I.E.D...NLL.........N.S....T......N.ED...Q.
BAA14334   .E.......FDE.K.R.SA..I.A...D.L....N......T.K....K..E..A.
BAA14336   .A.......R..H.....M.K..K.E...TF...NK.I.RV........T.RV...K.FE...I
BAA14337   .E.A...R..HDR...V..E..I.T.D...L...NN..DT........N.K..E...I
BAA14338   .M.A.....H.Q......E.K..I.E...LL...NN.........T.A...
CAB95856   .E.A...N....N...K.A.GS..ME..K...L....Q..N.S....T......NRRK....R.
```

FIG. 7I

```
Positions from 541 till 595
consensus  NRQEIDGVKLESGGNVYKILSIYSTVASSLVLAALIAGFIFWACSNGNCRCTICI
AAA43678   .N..K....S.M..Q....A..A..G..S..IMM..IS..M....SLQ.R....
AAA79775   .LN.NP...S......-YKD.ILWF.FGE.CF..L.VVM.LV..FCLK......
AAA96134   .IM.NP...S......-YKD.ILWF.FG...CVM.L.IAM.L...MCVK.L...
AAC40998   .IQ..P...S......-YKD.ILWF.FG...CVM.L.IAM.LV..ICVK..M..
AAD17229   .E.......M...Q...A..............CFI.L.IAM.LV..ICVK..M..
AAD21159   .E..S....M..T.Q.................LVSLGAIS..M....SLQ.R..
AAF99711   .FQ.Q....TQ.-YKD.ILWI.FSI.CFL.V..LLA..L..Q..H..Q.......
AAK51718   .FQ.K..E.K...-YKDWILWI.FAI.CFL.CVVLL..M..QR..I..N......
AAX78820   ........S..NL..Q...A.........S..VG..IAMGL..M..SMP.K....
ABB87356   K....E.I.KTED....V..........CI..I.MVG..LA..M..S..FNV...
BAA14334   E..SK.N..ENT-T..................A..C..I..GLILGMQ..S..MF.
BAA14336   ....E....D.S.A..................CI.....M..M...............
BAA14337   E..KVN...ENS-T..............S...CI.....LLM.I.GFIFG.Q..V..F.
BAA14338   K....I...K.ED....A..........V...VG..LS..M....S..FNV...
CAB95856   E..K.E...E.-T...T...............MGF.A.L..N......S..N...
```

FIG. 7J

TURKISH SEROLOGY

VARIOUS SERUM SAMPLES TESTED ON H5 ANTIGEN

FIG. 12

SEQUENCE ALIGNMENTS COMPARING TURKISH DONORS TO VIETNAMESE DONOR

3-30 HEAVY CHAIN CLONES

3-23 heavy chain clones

Round 2:
Clone H8 heavy chain
```
R2_H11*   ---Q----L----G---------------L-T-----------A------------S-----R-E---------F-D-----N--------------EV-GM-S---S------K-----
VH3-30    QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAK
R2_H11*   ----L--------G---------GP---------------------E------E-----------------G------------R------I--------------S-FWTFGQGTKLEIKR
VKI_L12   DIQMTQSPSTLSASVGDRVTITCRASQSISSWLAWYQQKPGKAPKLLIYDASSLESGVPSRFSGSGSGTEFTLTISSLQPDDFATYYCQQYNSYS
```

Clone H02 heavy chain
```
R2_H02    E----------------------------------------------------H-------TETH-T--------ME-A-------D---------DVSLRAYDHYGMDVWGRGTLVRV
VH3-30    QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAK
```

Light chains and germline origins
```
R2_H02    ------------------------------E-----N-----N------R-----------------------G-S------A----I---------D-----D--RVFGGRTQLTVLS
VL3_31    SSELTQDPAVSVALGQTVRITCQGDSLRSYYASWYQQKPGQAPVLVIYGKNNRPSGIPDRFSGSSSGNTASLTITGAQAEDEADYYCNSRDSSGNH
```

* Heavy chain sequence found in additional clones with different light chains from Round 2 panning

Round 3:
Clone G12 heavy chain
```
G12       ----Q-----------------------------------G-----L-T-----------A------------S-----R-E---------F-D-----N--------------E-GM-S---S-----------
VH3-30    QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAK
```

Light chains and germline origins
```
G12       ----L-----------------D-N---------B-----V-FG-------------------------------E-----------A----------S-N--YTFGQGTKLEIKR
VKI_L19   DIQMTQSPSSVSASVGDRVTITCRASQGISSWLAWYQQKPGKAPKLLIYAASSLQSGVPSRFSGSGSGTDFTLTISSLQPEDFATYYCQQANSFP
```

Clone F01 heavy chain
```
F01       E------------------T------------T---------------------RK---L---------ME-A-------D---P-----------D--------------------Q------
VH3-30    QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAK
```

Light chains and germline origins
```
F01       ---------------------------------------------------------------------------F--QSY-T--FTFGGGTKVDIKR
VKI_A20   DIQMTQSPSSLSASVGDRVTITCRASQGISNYLAWYQQKPGKVPKLLIYAASTLQSGVPSRFSGSGSGTDFTLTISSLQPEDVATYYCQKYNSAP
```

FIG. 14

FIG. 15A           DONOR SPECIFIC H5N1 ELISA HITS

FIG. 15B    DONOR SPECIFIC H5N1 ELISA HITS

```
            81                                                                                                          160
A05  (80)  NQFSLKLSSVTAADTAMYYCAR-GV----YDWGNSYQLDVWGQGTLVTVSSGGGGSGGGGSGGGGSGGGGSSALDIQMTQSPSTLS
A11  (79)  NTAYLQMWSSLKTADTAMYFCAR-QA---DGYRSFYGMDVWGRGTLVTVSSGGGGSGGGGSGGGGSGGGGSSALDIQLTQSPSTLS
D12  (79)  NTAYMELRSLKSEDTAVYYCARDQGD--LWPHQYQGTDVWGKGTTVTVSSGGGGSGGGGSGGGGSGGGGS-SAEIVLTQSPLSLP
C03  (79)  DTLYLQMDSLRAEDTAVYFCAR------NRFTGYNYFEHWGQGTLVTVSSGGGGSGGGGSGGGGSGGGGSSALEIVMTQSPGTLS
B12  (79)  NSLYLQMSSLRAEDTAVYYCAR------TRFSGYDYFEDWGKGTLVTVSSGGGGSGGGGSGGGGSGGGGSSALEIVLTQSPGTLS
B07  (79)  NTLFLQMNSLRGEDTAIYYCAR------VRFSGYNYFENWGKGTTVTVSSGGGGSGGGGSGGGGSGGGGS--VHLKLTQSPATLS
A01  (79)  NTLYLQMDSLRGEDTAVYFCAR------VRFSGYNYFENWGKGTTVTVSSGGGGSGGGGSGGGGSGGGGSSALDIVMTQSPGTLS
C08  (79)  NTLYLQMDSLRGEDTAVYYCAR------VRFSGYFENWGQGTLVTVSSGGGGSGGGGSGGGGSGGGGSSALDVMTQSPSTLS
C06  (79)  NTLYLQMNSLRGEDTAVYYCAR------VRFSGYDYFENWGQGTLVTVSSGGGGSGGGGSGGGGSGGGGSSALEIVLTQSPGTLS    DONOR 1
D10  (79)  NTLTLQMNSLRGEDTAIYYCAR------VRFSGYDYFENWGKGTLVTVSSGGGGSGGGGSGGGGSGGGGSSALEIVMTQSPATLS
C11  (79)  NTLFLQMDSLRGEDTAVYYCAR------VRFSGYEYFENWGQGTLVTVSSGGGGSGGGGSGGGGSGGGGSSALEIVMTQSPGTLS
C04  (79)  NTLYLQMDSLRGEDTAVYYCAR------VRFSGYEYFENWGRGTLVTVSSGGGGSGGGGSGGGGSGGGGSSALEIVLTQSPGTLS
A03  (79)  NTLFLQMNSLRGEDTAIYYCAR------VRFSGYEYFENWGKGTLVTVSSGGGGSGGGGSGGGGSGGGGSSALEIVMTQSPSTLS
A02  (79)  NTLYLQMNSLRGEDTAVYYCAR------VRFSGYDYFENWGKGTLVTVSSGGGGSGGGGSGGGGSGGGGSSALEIVMTQSPGTLS
D05  (79)  NTLFLQMNSLRGEDTAIYYCAR------VRFSGYDYFENWGKGTLVTVSSGGGGSGGGGSGGGGSGGGGSSALEIVLTQSPGTLS
D04  (79)  NTLFLQMNSLRAEDTAIYYCAR------VRFSGYDYFENWGKGTLVTVSSGGGGSGGGGSGGGGSGGGGSSALEIVLTQSPGTLS
A04  (79)  NTLFLQMDSLRGEDTAIYYCAR------VRFSGYDYFENWGKGTLVTVSSGGGGSGGGGSGGGGSGGGGSSALDIQLTQSPSSVS
B10  (79)  NTLFLQMNSLRGEDTAIYYCAR------VRFSGYDYFENWGKGRGTLVTVSSGGGGSGGGGSGGGGSGGGGSSALEIVMTQSPGTLS
D02  (79)  NTLYLQMNRLRGEDTAVYYCAR------VRFSGYDYFENWGRGTTVTVSSGGGGSGGGGSGGGGSGGGGSSALEIVMTQSPATLS
H06  (79)  NTLYLQMDSLRGEDTAVYYCAR------VRFSGYEYFENWGKGTLVTVSSGGGGSGGGGSGGGGSGGGGSSAQSALTQ--PRSVS
F01  (79)  STTYMELSSLRSEDTAVYYCARSG----AGYNYYGMDVWGQGTLVTVSSGGGGSGGGGSGGGGSGGGGG---ALEIVLTQSPLSLP   DONOR 2
F02  (79)  STTYMELSSLRSEDTAVYYCALSG----AGYNYYGMDVWGKGTTVTVSSGGGGSGGGGSGGGGSGGGGSSALEIVLTQSPLSLP
G01  (79)  DTLYLQMNNLRAEDTAVYYCAKEVG---MRSYDSYGMDYWGQGTMVTVSSGGGGSGGGGSGGGGSGGGGSSALDIQMTQSPSSLS
A05  (79)  NSLYLQMDSLRGEDTAVYYCAR------AGSGYSSGPTDYWGKGTMVTVSSGGGGSGGGGSGGGGSGGGGS--AQSVLTQLP-SVS
A01  (79)  NALYLQMDSLRGEDTAVYYCARDRFGRSGIKLKVTYLDYWGEGTTVTVSSGGGGSGGGGSGGGGSGGGGSSALEIVLTQSPASLS
C01  (79)  NTVSLQMSSLKTDDTAVYYCAR------DFSWSGSIDSWGQGTLVTVSSGGGGSGGGGSGGGGSGGGGSSALDVVMTQSPGTLS
D01  (79)  NALYLQMDSLRGEDTAVYYCARDRFGRSGIKLKVTYLDYWGKGTLVTVSSGGGGSGGGGSGGGGSGGGGSSALDIQMTQSPSSLS    DONOR 3
A03  (79)  NALYLQMDSLRAEDTAVYYCARDRFGRSGIKLKVTYLDYWGKGTLVTVSSGGGGSGGGGSGGGGSGGGGSSALEIVLTQSPGTLS
C09  (79)  NALYLQMNSLRGEDTAVYYCARDRFGRSGIKLKVTYLDYWGRGTLVTVSSGGGGSGGGGSGGGGSGGGGSSALDIQLTQSPSTLS
C06  (79)  NALYLQMNSLRGEDTAVYYCARDRFGRSGMKLKVTYLDYWGKGTLVTVSSGGGGSGGGGSGGGGSGGGGSSALDIQMTQSPSSLS
C11  (79)  NALYLQMDSLRGEDTAVYYCARDRFGRSGIKLKVTYLDYWGRGTTVTVSSGGGGSGGGGSGGGGSGGGGSS-AQSVLTQ--PPSVS
G05  (79)  NTLYLQMDSLRDEDTAVYYCAK------SLSMRYFLDLWGRGTLVTVSSGGGGSGGGGSGGGGSGGGGSS-AHVILTQ--PPSAS
H05  (79)  NTLFLQMNNLRDEDTAIYYCAKN-----GGDYMGAYIDNWGKGTLVTVSSGGGGSGGGGSGGGGSGGGGSS-AQSVLTQ--PPSVS
E07  (79)  SVGYMDILNSLITPEDTAVYYCAG----GDHVVKAALAYWGGGTTVTVSSGGGGSGGGGSGGGGSGGGGSS-AQSALTQ-PASES    DONOR 4
G01  (79)  NQLSLRLNSVTAADTAVYYCAR------HRLRSDQAFDLWGKGTLVTVSSGGGGSGGGGSGGGGSGGGGSS-AQSVLTQ--PPSVS
H01  (79)  NTLYLQMNSLRDEDTAVYYCAK------SLSMRYFLDLWGRGTLVTVSSGGGGSGGGGSGGGGSGGGGSALPELTQ--PPSAS
F02  (79)  NTLYLQMNSLRDEDTAVYYCAK------SLSMRYFLDLWGQGTMVTVSSGGGGSGGGGSGGGGSGGGGSS-AQSVLTQ--PPSAS
E01  (79)  NQFSLSLITSVTAADTAVFYCARS----NGDYDTFTAYYWGRGTMVTVSSGGGGSGGGGSGGGGSGGGGSS-AQAVLTQ--PPSVS
H10  (80)  NQFTLKLSAVTAADTAVYYCAR------DVWEPGTFEHWGKGTMVTVSSGGGGSGGGGSGGGGSGGGGSSALSSELTQDP-AVS
```

FIG. 15C    DONOR SPECIFIC H5N1 ELISA HITS

FIG. 15D

DONOR SPECIFIC H5N1 ELISA HITS

| Clone | Position | 241 … 291 | Donor |
|---|---|---|---|
| A05 | (231) | CQQYYR-S---WTFGQGTKLEIKRAAAHHHHHHGEQKLISEEDL------- | DONOR 1 |
| A11 | (230) | CQQSYS-TP--VTFGQGTRLEIKRAAAHHHHHHGEQKLISXEDL------- | |
| D12 | (236) | CMQALQ-VP--HTFGQGTKVEIKRAAAHHHHHHGEQKIDLX---------- | |
| C03 | (229) | CQQYA--ASP-ETFGQGTKVEIKRAAAHHHHHHGEQKLISEEDL------- | |
| B12 | (229) | CQQYG--RSP-LTFGGGTKVEIKRAAAHHHHHHGEQKLISXEDL------- | |
| B07 | (226) | CQQYG--SSP-VTFGQGTKLEIKRAAAHHHHHHGEQKLISXEDL------- | |
| A01 | (229) | CQQYA--ASP-ETFGQGTKVEIKRAAAHHHHHHGEQKLISXXNL------- | |
| C08 | (228) | CQQYN--TYSSATFGQGTKVEIKRAAAHHHHHHGEQKLISEEDL------- | |
| C06 | (229) | CQQYG--SSPPYTFGQGTKLEIKRAAAHHHHHHGEQKLISXEDL------- | |
| D10 | (228) | CQQYD--NWP-LTFGGGTKVEIKRAAAHHHHHHGEQKLISXEDL------- | |
| C11 | (229) | CQQYG--SSP-FTFGGGTKVEIKRAAAHHHHHHGEQKLISEXDL------- | |
| C04 | (229) | CQQYA--SSP-LTFGGGTKVEIKRAAAHHHHHHGEQKLISXEDL------- | |
| A03 | (229) | CQQYG--SSS-YTFGQGTKLEIKRAAAHHHHHHGEQKLISEEDL------- | |
| A02 | (229) | CQQYG--SSP-GTFGQGTKVEIKRAAAHHHHHHGEQKLISEEDL------- | |
| D05 | (229) | CQQYG--SSLALTFGGGTKVEIKRAAAHHHHHHGEQKLISXEDL------- | |
| D04 | (228) | CQQYN---SFPLTFGGGTKVEIKRAAAHHHHHHGEQKLISEEDL------- | |
| A04 | (229) | CQQYA--ASP-ETFGQGTKVEIKRAAAHHHHHHGEQKLISXEDL------- | |
| B10 | (229) | CQQYA--ASP-ETFGQGTKVEIKRAAAHHHHHHGEQKLISXEDL------- | |
| D02 | (228) | CQQYD--NWP-LTFGGGTKVEIKRAAAHHHHHHGEQKLISEEDLX------ | DONOR 2 |
| H06 | (229) | CSSYTS-SSTLVIPGGRTKLTVLGAAAHHHHHHGEQKLISXENC------- | |
| F01 | (231) | CMQALQ-TP--LTFGGGTKVEIKRAAAHHHHHHGEQKLISEXNCKLLKVV- | |
| F02 | (234) | CMQALQ-TP--RTFGPGTKVEIKRAAAHHHHHHGEQKLISX--XDLX---- | |
| G01 | (231) | CQQSY---STPYTFGQGTKVEIKRAAAHHHHHHGEQKLISXEDL------- | |
| A05 | (230) | CQSYDT-NLRAYVFGTGTKLTVLXAAAHHHHHHGKQN-SQ----------- | DONOR 3 |
| A01 | (234) | CQQYN--SWPPITFGQGTRLEIKRAAAHHHHHHGEQKLISEEDL------- | |
| C01 | (228) | CQQYS--SSLSLTFGGGTKVEIKRAAAHHHHHHGEQKLISEEXL------- | |
| D01 | (234) | CQQSYN-TP--LTFGGGTKVDIKRAAAHHHHHHGEQKLISXEDL------- | |
| A03 | (235) | CQQYG----NSLNFGGGTKLEIKRAAAHHHHHHGEQKLISXEDL------- | |
| C09 | (234) | CQQYHR-FS--YSFGQGTKVEIKRAAAHHHHHHGEQKLISXENL------- | |
| C06 | (234) | CQQTYS-SP--LTFGGGTKVEIKRAAAHHHHHHGEQKLISXEDL------- | |
| C11 | (234) | CGTWDA-SLHSGLFGGGTKLTVIGAAAHHHHHHGEQKLISEEDL------- | |
| G05 | (227) | CAAWDD-SLNGWVFGGGTKVTVLXAAAHHHHHHGEQKLISEEDL------- | DONOR 4 |
| H05 | (229) | CGTWDS-SLSAGVFGGGTQLTVLGAAAHHHHHHGEQKLISEEDL------- | |
| E07 | (229) | CSSYT--TSNNLVFGGGTKLTVLGAAAHHHHHHGEQKLISXEDL------- | |
| G01 | (228) | CQSYDS-SLSGSVFGGGTQLTVLSAAAHHHHHHGEQKLISXEDL------- | |
| H01 | (227) | CAAWDD-SLNGLVFGGGTKLTVLGAAAHHHHHHGEQKLISEEDL------- | |
| F02 | (227) | CAAWDD-SLNGWVFGGGTKLTVLXAAAHHHHHHGEQKLISEEDL------- | |
| E01 | (230) | CQSYDS-SLSGSVFGGGTKVTVLXAAAHHHHHHGEQKLISXEDL------- | |
| H10 | (227) | CNSRDSNGDVLSVFGGGTKLTVLXAAAHHHHHHGEQKLISEEDL------- | |

HEAVY CHAIN DESTINATIONAL MUTAGENESIS

| SOURCE | CDR1 | CDR2 | CDR3 |
|---|---|---|---|
| G12 | - T - - - - - - - | - - - - S - - - - - - - - - - - R - E - - - | - - E - G M - S - - - |
| R2_H8* | - T - - - - - - - | - - - - S - - - - - - - - - - - R - E - - - | - - E V G M - S - - - |
| F01 | T - - - - - - - - | - - - - - - - - - - - - - - - - R K - - - - | - - D - - - - - - - - |
| R2_H02 | - - - - - - - H - | - - - - - - - - - - - - - - - - T E T H - - | D V S L  R A Y D H Y G M D |
| VH3-30 | S S Y G M H | W V A V I S Y D G S N K Y A K | |
| JH6 | | | y y y y y g m d |

DESTINATIONAL LIBRARY

| S S Y G M H | W V A V I S Y D G S N K Y A K D V G M | R y y y y y g m d |
|---|---|---|
| T T | H S  R K E H  E S L  A D H | S S |
| | D  T E T  D | D P |
| | L  P D A | R |
| | | N |

| DIVERSITY | 4 | 1024 | 384 | 1.6E+06 |
|---|---|---|---|---|
| | | | | COMBINATORIAL DIVERSITY |

FIG. 16

FIG. 17  LIGHT CHAIN DESTINATIONAL MUTAGENESIS

KAPPA

| SOURCE | CDR1 | CDR2 | CDR3 |
|---|---|---|---|
| G12 | N - - - - - | V - F G - - - - - - - - - - - - | - - - S - N - - Y |
| VKI_L19 | S S W L A W Y | L L I Y A A S S L Q Q | Q A N S F P |
| JK2 | | | y |

DESTINATIONAL LIBRARY

| | | | |
|---|---|---|---|
| S S W L A W Y<br>N | L L I Y A A S S L Q Q<br>V F G<br>C<br>D | Q A N S F P Y<br>S N | |

| DIVERSITY | 2 | 16 | 4 | 128 COMBINATORIAL DIVERSITY |
|---|---|---|---|---|

LAMBDA

| SOURCE | CDR1 | CDR2 | CDR3 |
|---|---|---|---|
| R2_H02 | N - - - N - - | - - - - - - G - S - - | D - - - - D - - - R |
| L3_31 | S Y Y A S W Y | L V I Y G K N N R P N | S R D S S G N H |
| JL7 | | | a |

DESTINATIONAL LIBRARY

| | | |
|---|---|---|
| S Y Y A S W Y<br>N | L V I Y G K N N R P N<br>G S<br>R<br>E | S R D S S G N H A<br>Q D R |

| DIVERSITY | 4 | 8 | 8 | 256 COMBINATORIAL DIVERSITY |
|---|---|---|---|---|

DONOR SPECIFIC ANTIBODY LIBRARIES

CROSS REFERENCE TO RELATED APPLICATIONS

This is a continuation-in-part of U.S. application Ser. No. 11/748,980, filed on May 15, 2007, now abandoned, which claims priority under 35 U.S.C. §119(e) from U.S. provisional patent application Nos. 60/800,787, filed May 15, 2006 and 60/855,679, filed Oct. 30, 2006, the entire disclosures of which are expressly incorporated by reference herein.

SEQUENCE LISTING

The instant application contains a Sequence Listing which has been submitted via EFS-Web and is hereby incorporated by reference in its entirety. Said ASCII copy, created on Jul. 26, 2010, is named SLN-0004.txt, and is 233,503 bytes in size.

FIELD OF THE INVENTION

The present invention concerns donor-specific antibody libraries and methods of making and using thereof. The present invention also concerns neutralizing antibodies obtained from such donor-specific antibody libraries and methods of using the antibodies obtained for the prevention and/or treatment of various human diseases and conditions.

BACKGROUND OF THE INVENTION

The generation and identification of specific agents for the diagnosis, prevention, and treatment of human diseases requires access to vast collections of useful chemistries. With the advent and rapid development of a variety of techniques for the creation and screening of antibody libraries, monoclonal antibodies against disease targets have become one of the major categories of new drug candidates. Since for human use, in addition to specificity and efficacy, safety is of primary concern, libraries of human monoclonal antibodies have become of particular importance.

At present, the development of human antibody-based drug candidates are typically identified by screening of human antibody libraries comprising a random collection of antibody sequences from human repertoires that are typically unrelated to their intended application or applications. Each antibody library created from a specific human donor potentially contains antibodies to every component, physiology, and metabolic alteration stemming from, or creating, every unique challenge that the donor has encountered, challenged, and surmounted over the course of that individual's lifetime. As typical human antibody libraries made with the current approaches are constructed without the knowledge of the health history of donors, little is known of what would be expected in the resulting immunoglobulin repertoires.

Thus, it is of great interest to create antibody libraries from individuals who have successfully survived or are surviving an encounter with specific diseases because their resulting repertoires include antibodies that were used by the donor to defend specifically against a relevant disease. It is also important to provide methods for the efficient screening and handling of such libraries, including the ability to remove or isolate negative or positive elements, eliminate undesirable content, and produce human antibodies with improved properties.

The present invention addresses these needs by providing methods and means for the creation, screening and handling of donor-specific antibody libraries from individuals who have been exposed to and survived or are surviving an encounter with a specific target disease.

SUMMARY OF THE INVENTION

In one aspect, the invention concerns a vector collection comprising a repertoire of nucleic acid molecules encoding antibody light or heavy chains or fragments thereof, derived from a human patient donor who has suffered from, or is suffering from, a disease evoking antibody production to a target antigen, wherein the collection is identified with a unique barcode.

In one embodiment, the vector collection comprises a repertoire of nucleic acid molecules encoding antibody light chains or fragments thereof, such as antibody λ light chains, or antibody κ light chains, or fragments thereof.

In another embodiment, the vector collection comprises a repertoire of nucleic acid molecules encoding antibody heavy chains or fragments thereof.

In yet another embodiment, the barcode is a nucleotide sequence linked to or incorporated in the vectors present in the collection, and/or linked to or incorporated in the nucleic acid molecules encoding the antibody light or heavy chains or fragments thereof such that it does not interfere with the expression of the nucleic acid molecules.

Thus, the barcode may be contiguous non-coding nucleotide sequence of one to about 24 nucleotides, which may, for example, be linked to the 3' or 5' non-coding region of the nucleic acid molecules.

In a further embodiment, the barcode is a nucleotide sequence that is a coding sequence of one or more silent mutations incorporated into the nucleic acid molecules encoding the antibody light or heavy chains or fragments thereof.

In a still further embodiment, the barcode is a non-contiguous nucleotide sequence. At least part of the non-contiguous nucleotide sequence may be linked to or incorporated in the vectors present in the collection. Alternatively, at least part of the non-contiguous nucleotide sequence may be incorporated into the nucleic acid molecules encoding the antibody light or heavy chains or fragments thereof such that it does not interfere with the expression of said nucleic acid molecules.

In another embodiment, the barcode is a peptide or polypeptide sequence.

In a different embodiment, the vectors present in the vector collection are phagemid vectors, which may, for example, contain a bacteriophage gene III and a stop codon between the nucleic acid molecules encoding antibody light or heavy chains or fragments thereof and the bacteriophage III gene, and may have a barcode, such as a non-coding contiguous nucleotide sequence inserted in the untranslated region following the stop codon.

In another aspect, the invention concerns host cells comprising the vector collection of the present invention. The host cells may by eukaryotic or prokaryotic host cells, such as, for example, E. coli cells.

In a further aspect, the invention concerns a donor-specific antibody library comprising library members expressing a collection of antibodies or antibody fragments to a target antigen wherein the antibodies or antibody fragments are derived from a human donor who has suffered from, or is suffering from, a disease evoking antibody production to said target antigen, wherein said antibody library is identified with at least one unique barcode.

In one embodiment, the antibody heavy and light chains are separately identified each with a barcode unique to the human donor from whom it derived.

In another embodiment, the donor-specific antibody library is identified with one unique barcode.

In yet another embodiment, the antibodies or antibody fragments are composed of antibody heavy and light chains or fragments thereof encoded by nucleic acid molecules present in a vector.

In a further embodiment, the barcode is a nucleotide sequence linked to or incorporated in the vectors present in the library, and/or linked to or incorporated in the nucleic acid molecules encoding the antibody light or heavy chains or fragments thereof such that it does not interfere with the expression of the nucleic acid molecules.

In a still further embodiment, the barcode is a contiguous non-coding nucleotide sequence of one to about 24 nucleotides, which may, for example, be linked to the 3' or 5' non-coding region of the nucleic acid molecules.

In a different embodiment, the barcode is encoded by a coding sequence of one or more silent mutations incorporated into the nucleic acid molecules encoding the antibody light or heavy chains or fragments thereof.

In another embodiment, the barcode is encoded by a non-contiguous nucleotide sequence.

In a further embodiment, a least part of the non-contiguous sequence encoding the barcode is linked to or incorporated in the vectors present in the library.

In a still further embodiment, at least part of the non-contiguous sequence encoding the barcode is incorporated into the nucleic acid molecules encoding the antibody light or heavy chains or fragments thereof such that it does not interfere with the expression of such nucleic acid molecules.

In different embodiment, the barcode is a peptide or polypeptide sequence.

In another embodiment, vectors are phagemid vectors, may, for example, contain a bacteriophage gene III and a stop codon between the nucleic acid molecules encoding antibody light or heavy chains or fragments thereof and the bacteriophage III gene.

In yet another embodiment, the medical history of the human patient donor shows that the donor has suffered from, or is suffering from said disease. In some embodiments, it is independently confirmed that the human donor suffered from, or is suffering from the disease.

In an additional embodiment, the donor-specific antibody library is substantially devoid of antibodies and antibody fragments specifically binding antigens different from said target antigen.

In one embodiment, the target antigen is an influenza A virus, such as an isolate of influenza A virus H1, H2, H3, H5, H7, or H9 subtype.

In another embodiment, the library expresses at least one antibody or antibody fragment specifically binding to more than one influenza A virus subtype.

In yet another embodiment, the library expresses at least one antibody or antibody fragment binding to and neutralizing the H5N1 subtype of influenza virus A.

In a further embodiment, the human donor has suffered from, or is suffering from a disease selected from the group consisting of the diseases listed in Table 1 below.

In a still further embodiment, the antibody library expresses at least one antibody or antibody fragment binding to an antigen associated with the target disease.

In an additional embodiment, the antibody library expresses at least one antibody or antibody fragment binding to and neutralizing an antigen associated with the target disease.

The donor-specific antibody library may, for example, be a phage library, in an embodiment, it may contain sequences encoding more than $10^6$ different members of antibodies or antibody fragments, or more than $10^9$ different members of antibodies or antibody fragments.

In other embodiments, the donor-specific antibody library is, without limitation, a spore-display library, a ribosome display library, a mRNA display library, a microbial cell display library, a yeast display library, or a mammalian display library.

In an embodiment, the nucleic acid encoding the antibodies or antibody fragments present in the library is reverse-transcribed from mRNA extracted from lymphocytes of the human patient donor, where the lymphocytes may, for example, originate from bone marrow, blood, spleen, or lymph node.

If desired, a serological profile of said human donor may be generated prior to extraction of said mRNA.

Alternatively, or in addition, the medical history of the human donor, and optionally the donor's family, is examined prior to or following extraction of the mRNA.

In another aspect, the invention concerns a method of making a donor-specific library expressing a collection of antibodies or antibody fragments to a target antigen, comprising the steps of:

a) obtaining mRNA from lymphocytes of a human patient donor who has suffered from, or who is suffering from a disease evoking antibody production to said target antigen;
b) generating a collection of nucleic acids comprising sequences encoding an immunoglobulin repertoire of the patient by reverse transcription of said obtained mRNA; and
c) identifying the donor-specific library with an unique barcode labeling said nucleic acids.

The method may further comprise steps of generating a serological profile of said patient and/or examining medical history of the patient prior or subsequent to step a).

The method may further comprise the steps of d) inserting said nucleic acids into expression vector; e) expressing the immunoglobulin repertoire; and f) displaying the immunoglobulin repertoire in a display system.

In another embodiment, the method further comprises the step of selecting members of the library based their ability to neutralize or activate the target antigen.

In a still further embodiment, the method yields at least one neutralizing antibody.

In another embodiment, the method further comprises the step of creating one or more sub-libraries comprising library members that were found to neutralize or activate the target antigen.

In yet another embodiment, the method comprises the step of sequencing at least one library member identified.

In a further aspect, the invention concerns a method of treating or preventing a disease associated with a target antigen neutralized or activated by an antibody selected by the method described above, comprising administering to a human patient in need an effective amount of the antibody selected.

The antibody may, for example, be a neutralizing antibody, such as a neutralizing antibody to at least one influenza A virus subtype.

In another embodiment, the disease is selected from the group consisting of the diseases listed in Table 1 below.

BRIEF DESCRIPTION OF THE DRAWINGS

FIG. 6 illustrates a representative mutagenesis method for generating a diverse multifunctional antibody collection by the "destinational mutagenesis" method. FIG. 6 discloses SEQ ID NOS 5, 4, 8, 6 and 7, respectively, in order of appearance. Consensus peptide disclosed as SEQ ID NO: 9.

Figure 7A:
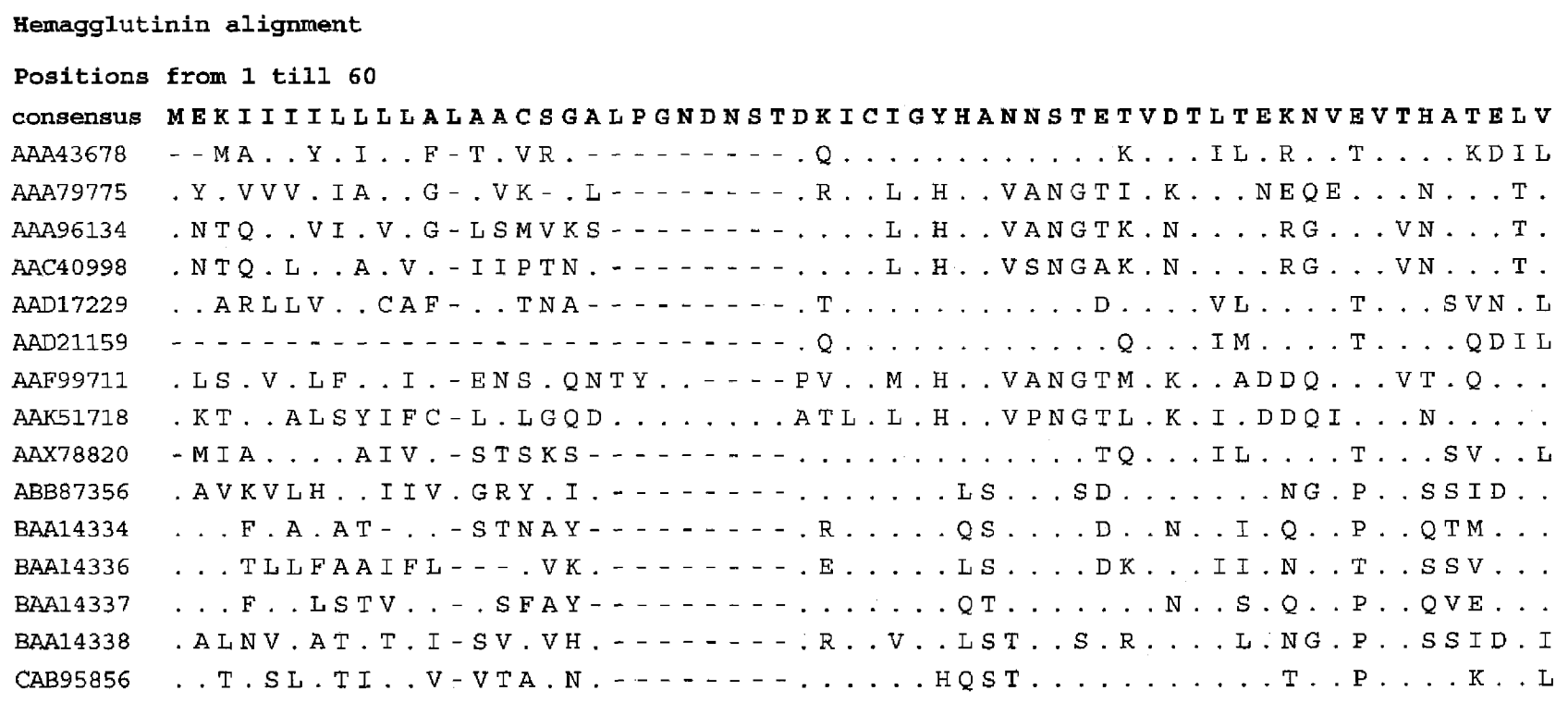
Figure 7B:
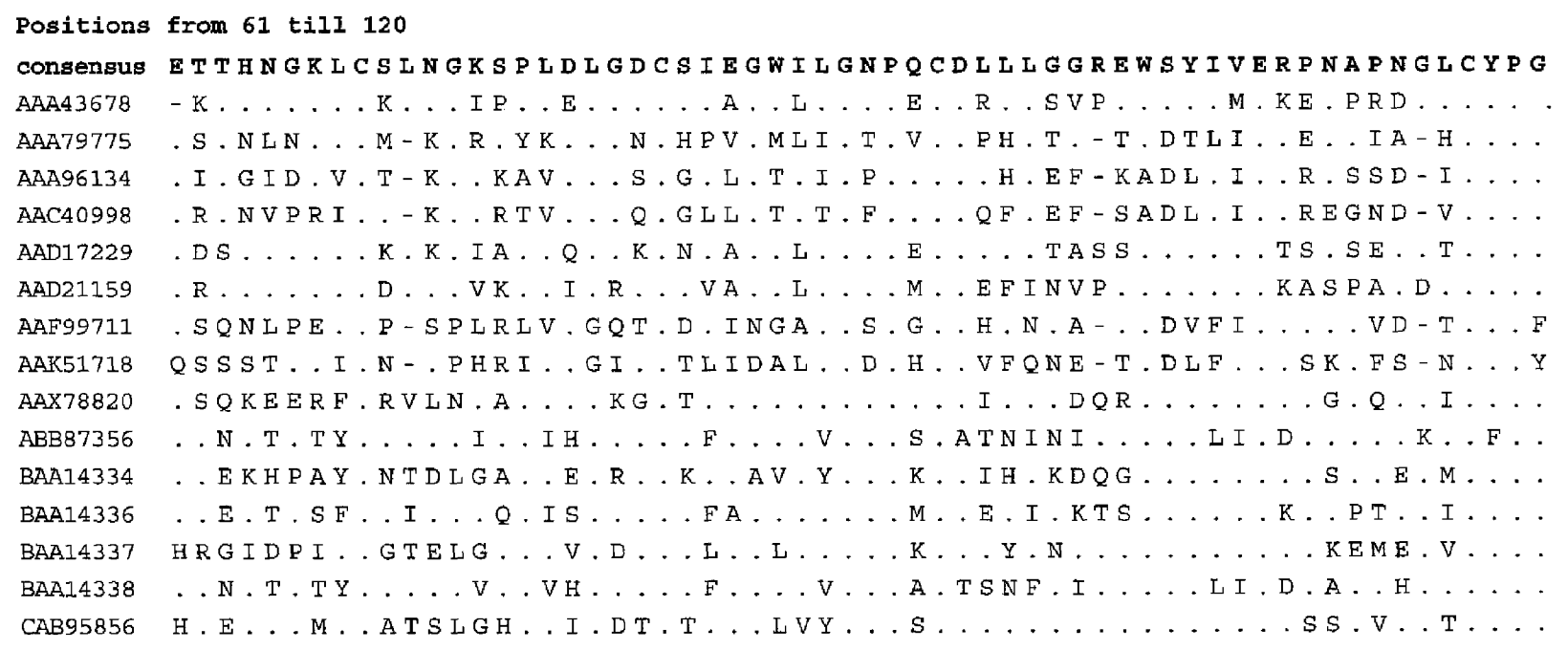
Figure 7C:
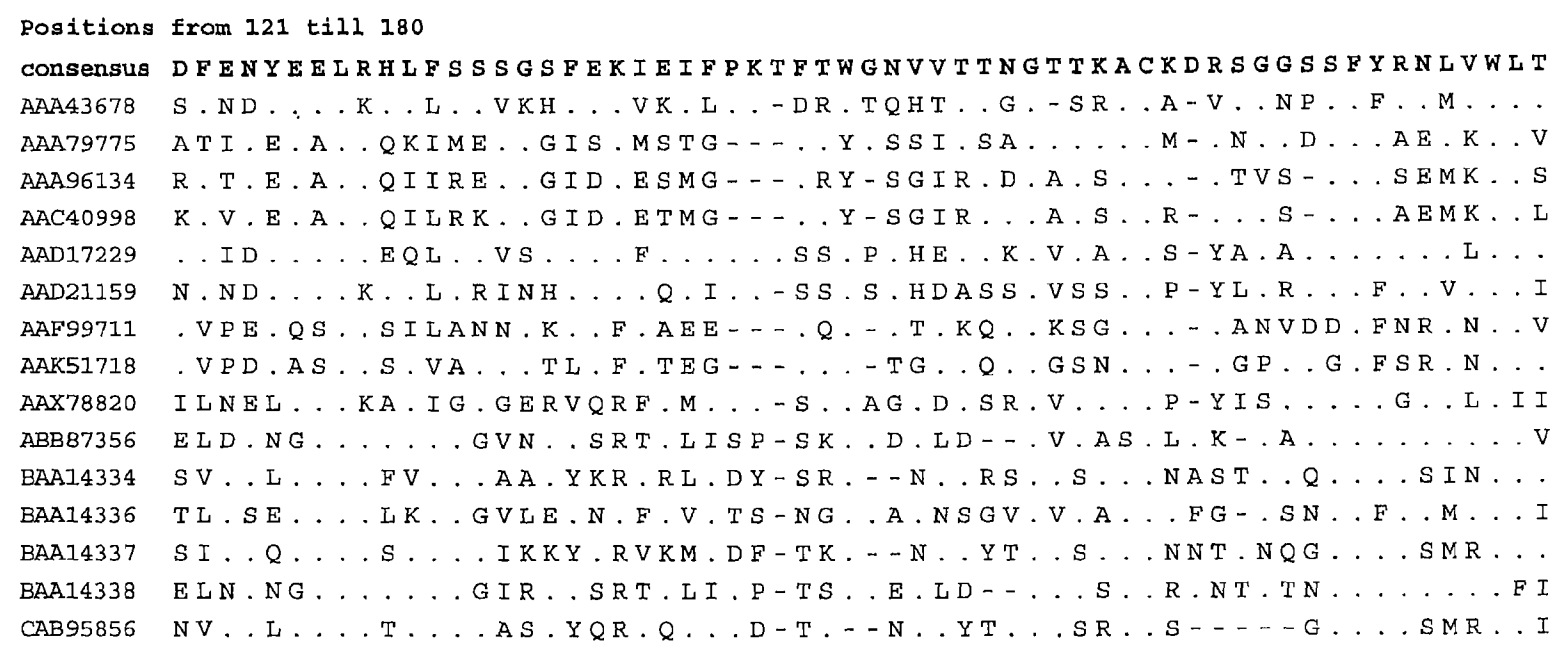
Figure 7D:
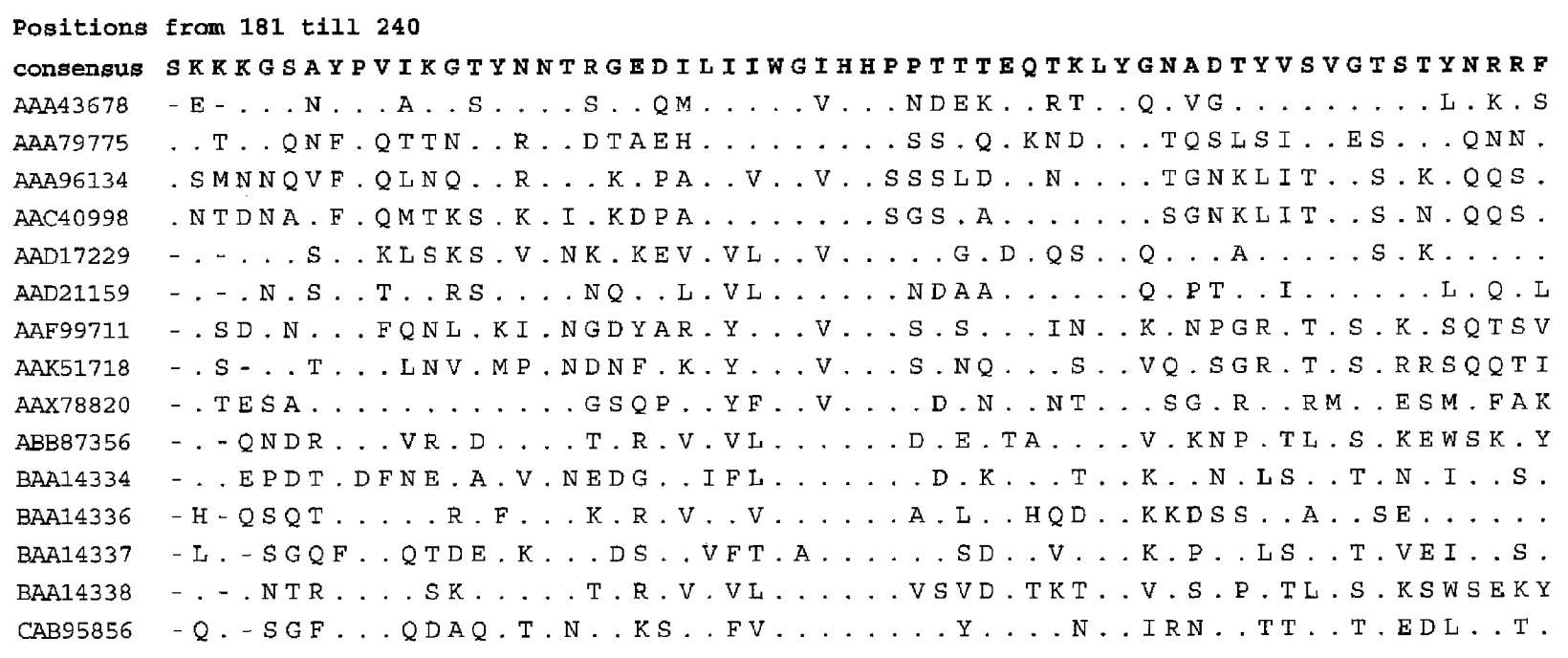

FIG. 7 shows the amino acid sequences of 15 known hemagglutinin (H) protein subtypes (SEQ ID NOS 10-25, respectively, in order of appearance).

FIG. 8 shows the H5 hemagglutinin (HA) serology results for blood samples obtained from six human survivors of a Turkish H5N1 bird flu outbreak. The data demonstrate the presence of antibodies to the HA antigen.

FIG. 9 shows serology results obtained with serum samples of twelve local donors, tested on H5 antigen (A/Vietnam/1203/2004) and H1N1 (A/New Caledonia/20/99) and H3N2 (A/Panama/2007/99) viruses.

FIG. 12 shows sequence alignments comparing the sequences of H5 hemagglutinin proteins from reported Turkish isolates (SEQ ID NOS 26-29, respectively, in order of appearance) and one Vietnamese isolate (SEQ ID NO: 30) downloaded from the Los Alamos National Laboratory sequence database.

FIGS. 13 and 14 show heavy chain variable region sequences of unique clones identified in pooled antibody libraries of Turkish donors, along with the corresponding light chain and germline origin sequences. The sequences shown in FIG. 13 (3-23 heavy chain clones) originate from a pooled library of all heavy and light chains of all Turkish donors after three rounds of panning. FIG. 13 discloses SEQ ID NOS 31-34, 31-32, 35-37, 32, 38-40, 32 and 41-42, respectively, in order of appearance. The sequences shown in FIG. 14 (3-30 heavy chain clones) originate from a pooled library of all heavy and light chains of all Turkish donors after two rounds of panning. FIG. 14 discloses SEQ ID NOS 43-47, 44, 48-50, 44, 51-53, 44 and 54-55, respectively, in order of appearance.

Figure 15A:
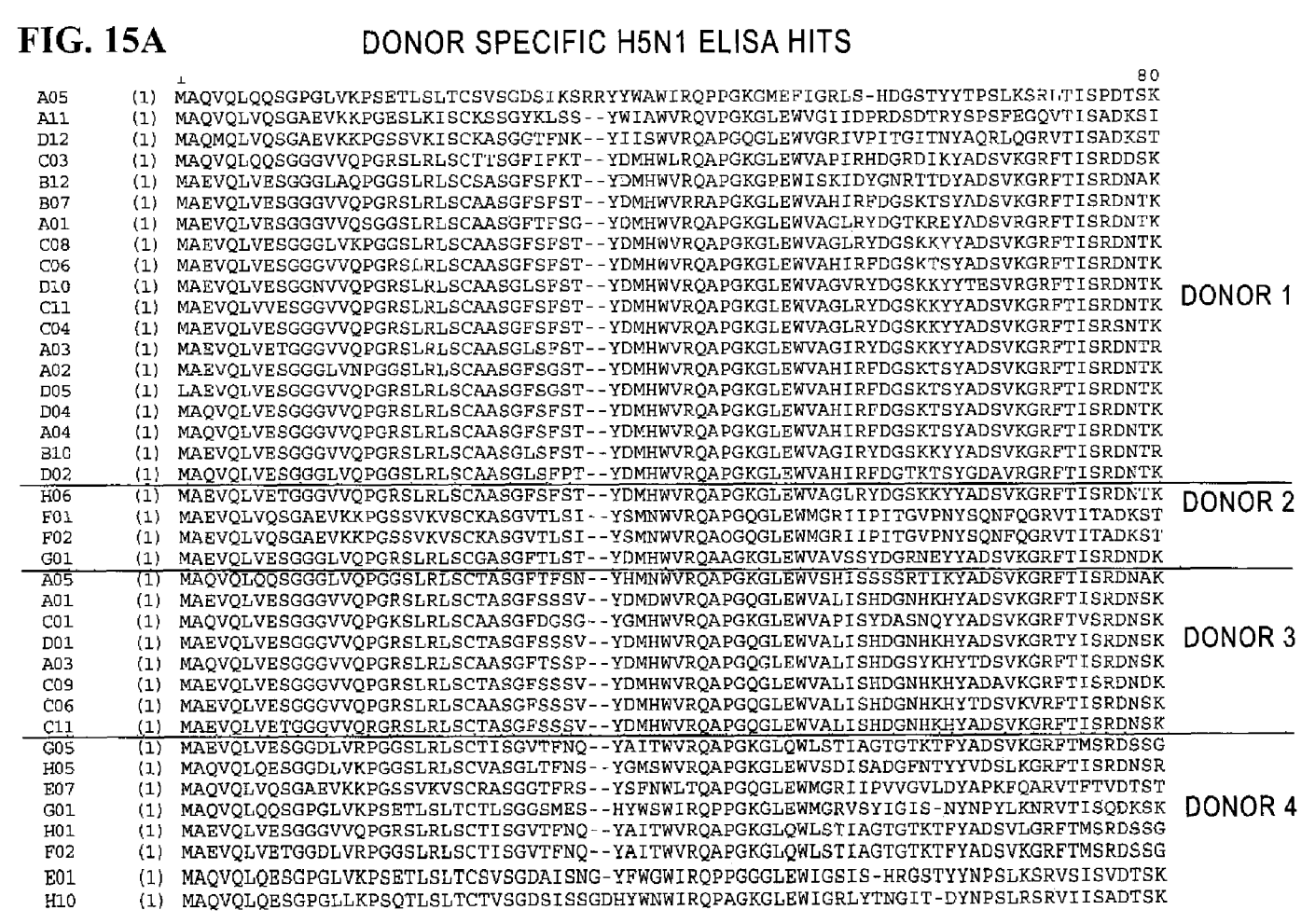
Figure 15C:
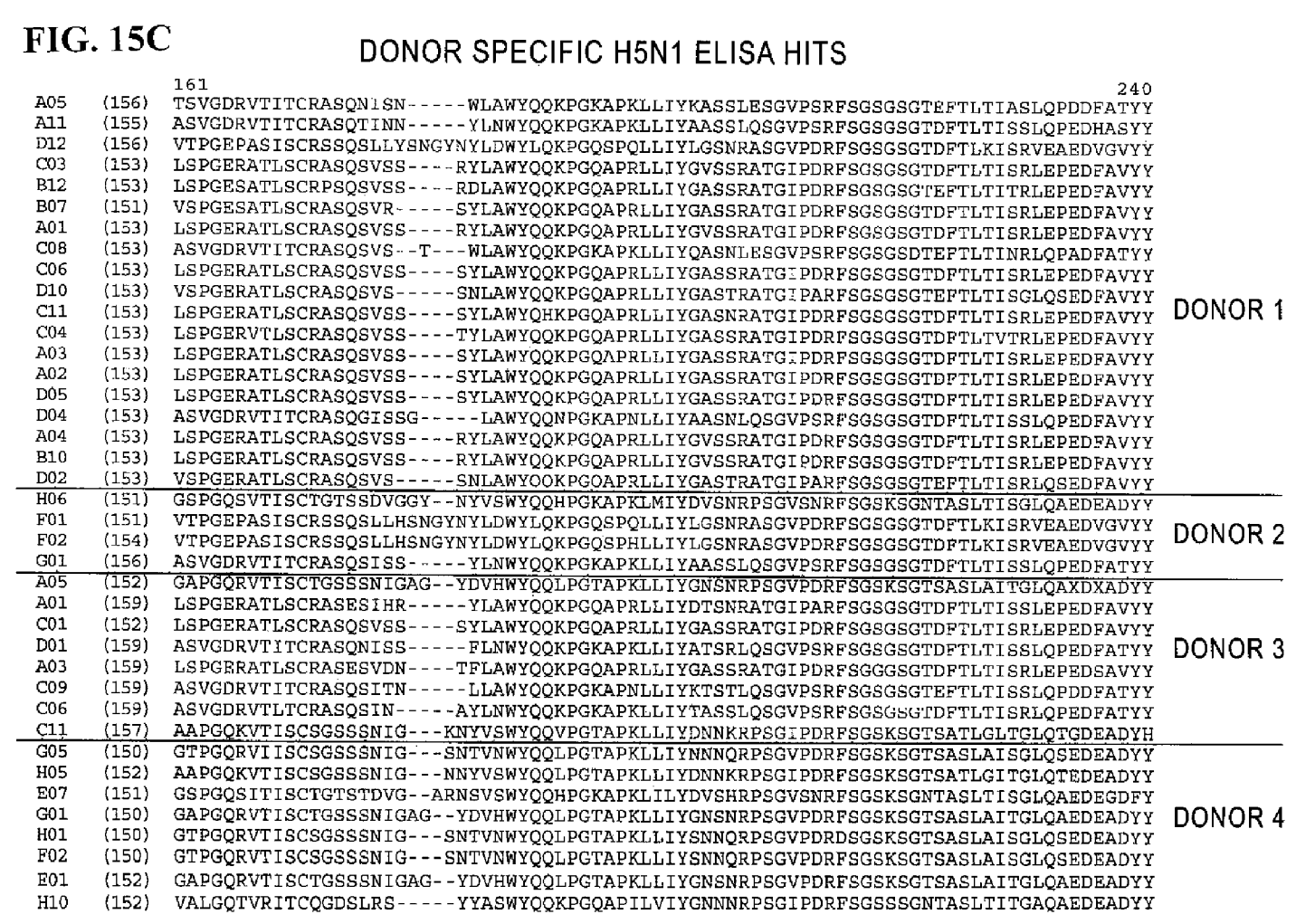

FIGS. 15A-D show additional unique H5N1-specific antibody heavy chain variable region sequences (SEQ ID NOS 56-94, respectively, in order of appearance) identified from antibody libraries of individual Turkish donors, after four rounds of panning.

FIGS. 16 and 17 illustrate the use of destinational mutagenesis to create diverse antibody heavy and light chain libraries using the antibody heavy (FIG. 16) and light chain (FIG. 17) sequences identified by analysis of sera and bone marrow of Turkish bird flu survivors. FIG. 16 discloses SEQ ID NOS 95 and 95-100, respectively, in order of appearance. FIG. 17 discloses SEQ ID NOS 101-106, respectively, in order of appearance.

DETAILED DESCRIPTION

A. Definitions

Figure 1:
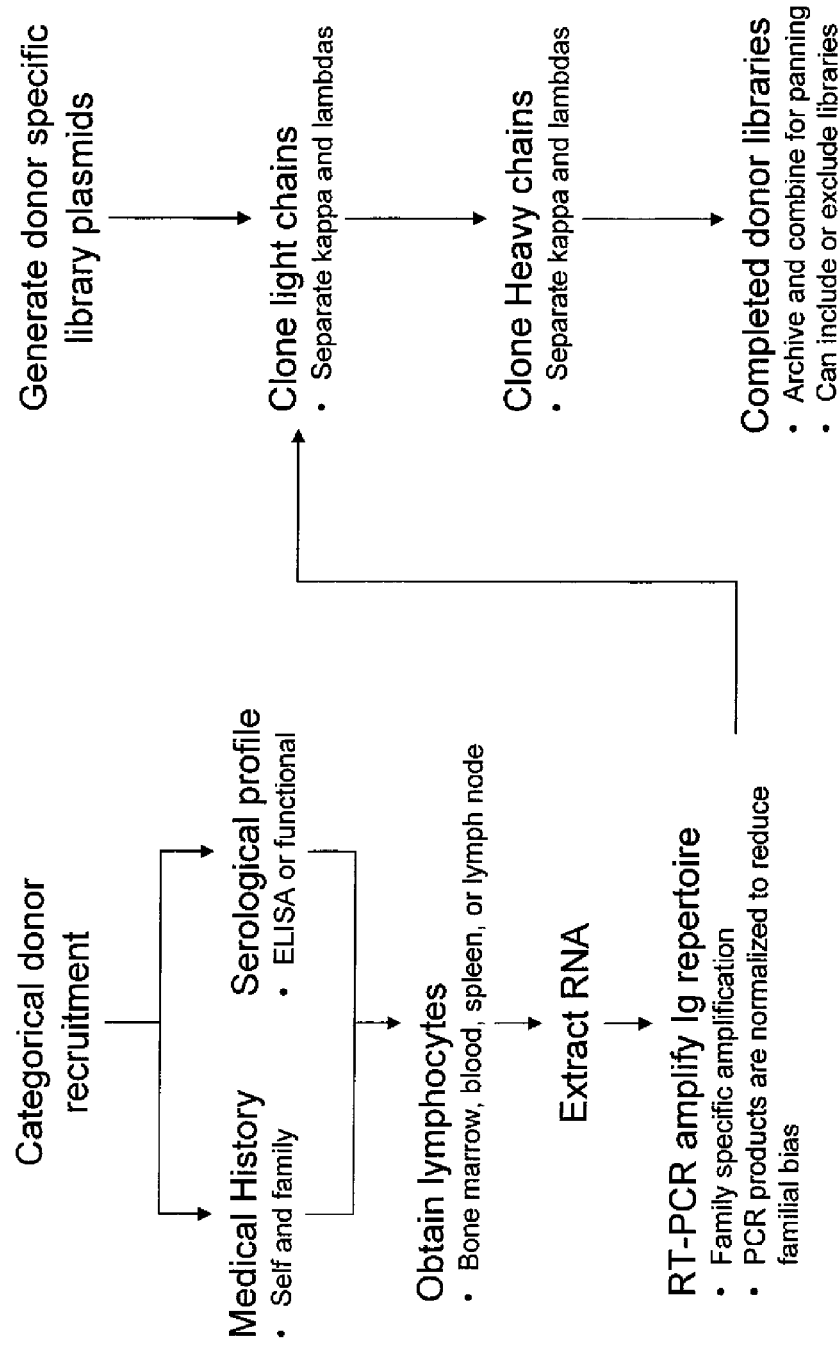
FIG. 1 is a flow chart schematically illustrating a typical method for the creation of the human antibody libraries of the present invention.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The phrase "conserved amino acid residues" is used to refer to amino acid residues that are identical between two or more amino acid sequences aligned with each other.

The terms "disease," "disorder" and "condition" are used interchangeably herein, and refer to any disruption of normal body function, or the appearance of any type of pathology. The etiological agent causing the disruption of normal physiology may or may not be known. Furthermore, although two patients may be diagnosed with the same disorder, the particular symptoms displayed by those individuals may or may not be identical.

An "effective amount" is an amount sufficient to effect beneficial or desired therapeutic (including preventative) results. An effective amount can be administered in one or more administrations.

A "composition," as used herein, is defined as comprising an active ingredient, such as a neutralizing antibody generated from the present invention, and at least one additive, such as a pharmaceutically acceptable carrier, including, without limitation, water, minerals, proteins, and/or other excipients known to one skilled in the art.

As used herein, the term "treating" or "treatment" is intended to mean an amelioration of a clinical symptom indicative of a disease.

As used herein, the term "preventing" or "prevention" is intended to mean a forestalling of a clinical symptom indicative of a disease The terms "subject" and "patient," as used herein, are used interchangeably, and can refer to any to animal, and preferably a mammal, that is the subject of an examination, treatment, analysis, test or diagnosis. Thus, subjects or patients include humans, non-human primates and other mammals, who may or may not have a disease or other pathological condition.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids may be used as desired. Thus, modified and unusual amino acids listed in 37 CFR 1.822(b)(4) are included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg).

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent to the specified residue. By insertion "adjacent" to a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301 336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

The term "vector" is used to refer to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Percent amino acid sequence identity may be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

"Antibody-dependent cell-mediated cytotoxicity" and "ADCC" are used herein to refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. Various immune cells express different Fc receptors (FcRs). Thus, the primary cells for mediating ADCC, NK cells, express FcγRIII only, whereas monocytes express FcγRI, FcγRII and FcγRIII.

The terms "influenza A subtype" or "influenza A virus subtype" are used interchangeably, and refer to influenza A virus variants that are characterized by various combinations of the hemagglutinin (H) and neuraminidase (N) viral surface proteins, and thus are labeled by a combination of an H number and an N number, such as, for example, H1N1 and H3N2. The terms specifically include all strains (including extinct strains) within each subtype, which usually result from mutations and show different pathogenic profiles. Such strains will also be referred to as various "isolates" of a viral subtype, including all past, present and future isolates. Accordingly, in this context, the terms "strain" and "isolate" are used interchangeably.

The term "influenza" is used to refer to a contagious disease caused by an influenza virus.

B. General Techniques

Techniques for performing the methods of the present invention are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; O'Brian et al., *Analytical Chemistry of Bacillus Thuringiensis*, Hickle and Fitch, eds., Am. Chem. Soc., 1990; *Bacillus thuringiensis: biology, ecology and safety*, T. R. Glare and M. O'Callaghan, eds., John Wiley, 2000; *Antibody Phage Display, Methods and Protocols*, Humana Press, 2001; and *Antibodies*, G. Subramanian, ed., Kluwer Academic, 2004. Mutagenesis can, for example, be performed using site-directed mutagenesis (Kunkel et al., *Proc. Natl. Acad. Sci USA* 82:488-492 (1985)). PCR amplification methods are described in U.S. Pat. Nos. 4,683,192, 4,683,202, 4,800,159, and 4,965,188, and in several textbooks including "PCR Technology: Principles and Applications for DNA Amplification", H. Erlich, ed., Stockton Press, New York (1989); and *PCR Protocols: A Guide to Methods and Applications*, Innis et al., eds., Academic Press, San Diego, Calif. (1990).

The methods of the present invention are not limited by any particular technology used for the display of antibodies. Although the invention is illustrated with reference to phage display, antibodies of the present invention can also be identified by other display and enrichment technologies, such as, for example, ribosome or mRNA display (Mattheakis et al., *Proc. Natl. Acad. Sci. USA* 91:9022-9026 (1994); Hanes and Pluckthun, *Proc. Natl. Acad. Sci. USA* 94:4937-4942 (1997)), microbial cell display, such as bacterial display (Georgiou et al., *Nature Biotech.* 15:29-34 (1997)), or yeast cell display (Kieke et al., *Protein Eng.* 10:1303-1310 (1997)), display on mammalian cells, spore display (Isticato et al., *J. Bacteriol.* 183:6294-6301 (2001); Cheng et al., *Appl. Environ. Microbiol.* 71:3337-3341 (2005) and co-pending provisional application Ser. No. 60/955,592, filed Aug. 13, 2007), viral display, such as retroviral display (Urban et al., *Nucleic Acids Res.* 33:e35 (2005), display based on protein-DNA linkage (Odegrip et al., *Proc. Acad. Natl. Sci. USA* 101:2806-2810 (2004); Reiersen et al., *Nucleic Acids Res.* 33:e10 (2005)), and microbead display (Sepp et al., *FEBS Lett.* 532:455-458 (2002)).

In ribosome display, the antibody and the encoding mRNA are linked by the ribosome, which at the end of translating the mRNA is made to stop without releasing the polypeptide. Selection is based on the ternary complex as a whole.

In a mRNA display library, a covalent bond between an antibody and the encoding mRNA is established via puromycin, used as an adaptor molecule (Wilson et al., *Proc. Natl. Acad. Sci. USA* 98:3750-3755 (2001)). For use of this technique to display antibodies, see, e.g., Lipovsek and Pluckthun, *J. Immunol. Methods.* 290:51-67 (2004).

Microbial cell display techniques include surface display on a yeast, such as *Saccharomyces cerevisiae* (Boder and Wittrup, *Nat. Biotechnol.* 15:553-557 (1997)). Thus, for example, antibodies can be displayed on the surface of *S. cerevisiae* via fusion to the α-agglutinin yeast adhesion receptor, which is located on the yeast cell wall. This method provides the possibility of selecting repertoires by flow cytometry. By staining the cells by fluorescently labeled antigen and an anti-epitope tag reagent, the yeast cells can be sorted according to the level of antigen binding and antibody expression on the cell surface. Yeast display platforms can also be combined with phage (see, e.g., Van den Beucken et al., *FEBS Lett.* 546:288-294 (2003)).

For a review of techniques for selecting and screening antibody libraries see, e.g., Hoogenboom, *Nature Biotechnol.* 23(9):1105-1116 (2005).

C. Detailed Description of Preferred Embodiments

I. Preparation of Donor-Specific Antibody Libraries
The present invention concerns donor-specific antibody libraries from individuals who have successfully survived or are surviving an encounter with a specific disease. The resulting antibody repertoires will include antibodies that were used by the donor to defend specifically against a relevant disease, and thus are important tools, for example, for developing neutralizing antibodies for the prevention and/or treatment of a target disease.

While the present invention is applicable to any target disease that evokes antibody production in a human subject, representative, non-limiting, examples of such diseases are listed in Table 1.

TABLE 1

| Type of disorder | Representative examples |
|---|---|
| infectious disorder | Influenza viral infection, hepatitis C virus (HCV) infection, herpes simplex virus (HSV) infection, human immunodeficiency virus (HIV) infection, Methicillin-resistant Staphylococcus aureus (MRSA) infection, Epstein-Barr virus (EBV) infection, respiratory syncytial virus (RSV) infection, Pseudomonas, Candida infections |
| Respiratory disorder | Asthma, Allergies, chronic obstructive pulmonary disease (COPD), idiopathic pulmonary fibrosis (IPF), adult respiratory distress syndrome (ARDS) |
| metabolic disorder | Frailty, cachexia, sarcopenia, Obesity, type II diabedyslipidemia, metabolic syndrome-associated myocardial infarction (MI), chronic renal failure (CRF), osteoporosis |
| digestive disorder | irritable bowel syndrome (IBS), inflammatory bowel disease (IBD), Chron's disease, fatty liver disease, fibrosis, drug-induced liver disease |
| Neurological disorder | Alzheimer's disease, multiple sclerosis (MS), Parkinson's disease, bovine spongiform encephalopathy (BSE, mad cow disease) |
| Cancer | e.g., breast, renal, stomach, melanoma, lung, colon, glioma, lymphoma |

A method of creating the donor-specific libraries of the present invention is schematically illustrated in FIG. 1. As a first step, potential donors are identified. The patient donor may currently suffer from or may have recovered from and survived a target disease. Thus, for example, as illustrated in the Examples, the donor-specific libraries herein may be created from the bone marrow of convalescent patients of prior influenza infections, including seasonal influenza outbreaks, epidemics, and pandemics.

When selecting or identifying a patient donor, it is important to confirm that the patient indeed had or is having the target disease. Part of the confirmation is the examination of the medical history of the patient donor. In addition to the medical history, various other factors, such as the medical history of the patient's family, the patient's sex, weight, health state, etc., should be taken into consideration. If the patient history is not available or unreliable, or for any other reason, such as a further confirmation measure, the serological profile of the patient may be determined. Serological assays are well known in the art and can be performed in various formats, such as in the form of various ELISA assay formats. Thus, for example, the presence of antibodies to an influenza virus can be detected by the well-known hemagglutinin inhibition (HAI) assay (Kendal, A. P., M. S. Pereira, and J. J. Skehel. 1982. *Concepts and procedures for laboratory-based influenza surveillance*. U.S. Department of Health and Human Services, Public Health Service, Centers for Disease Control, Atlanta, Ga.), or the microneutralization assay (Harmon et al., *J. Clin. Microbiol.* 26:333-337 (1988)). This step might not be necessary if the serum sample has already been confirmed to contain influenza neutralizing antibodies.

In order to prepare donor-specific human antibody libraries, samples containing lymphocytes are collected from individuals (patient donors) known to have developed a target disease, such as at least one disease from those listed in Table 1. The sample may, for example, derive from bone marrow, blood, spleen, lymph nodes, tonsils, thymus, and the like. Bone marrow is a preferred source of the antibody libraries herein, since it represents the complete "fossil archive" of individual donor's mature antibody repertoire.

Samples containing lymphocytes can be collected from the patient donor at various time points. In one embodiment, lymphocytes are collected from a patient who has recovered from the targeted disease(s) at least for 1, 5, 10, 15, 20, 25 days, at least for 1, 2, 3, 4, 5, 6, 7, 8, 9, 10, 11 months, or at least for 1, 2, 3, 4, 5, 6, 7, 8, 9, 10 years. In another embodiment, lymphocytes are collected from a patient who is having the targeted disease(s) at the time of collection, and has been diagnosed as having the disease(s) at least 1, 5, 10, 15, 20, 25 days, or at least 1, 2, 3, 4, 5, 6, 8, 9, 10 months, or 1, 2, 3, 4, or 5 years prior to collection.

Peripheral blood samples, especially from geographically distant sources, may need to be stabilized prior to transportation and use. Kits for this purpose are well known and commercially available, such as, for example, BD Vacutainer® CPT™ cell preparation tubes can be used for centrifugal purification of lymphocytes, and guanidium, Trizol, or RNAlater used to stabilize the samples. Methods and kits for isolating lymphocytes from other sources, such as lymphoid organs are also well known and commercially available.

Upon receipt of the stabilized lymphocytes or whole bone marrow, RNA is extracted and RT-PCR is performed to rescue antibody heavy and light chain repertoires, using immunoglobulin oligo primers known in the art.

Methods for preparation of RNA from bone marrow lymphocytes, or lymphocytes from any other source, are well known in the art. General methods for mRNA extraction are disclosed in standard textbooks of molecular biology, including Ausubel et al., *Current Protocols of Molecular Biology*, John Wiley and Sons (1997). RNA purification kits are available from commercial manufacturers, such as Qiagen, and can be used according to the manufacturer's instructions.

Since RNA cannot serve as a template for PCR, it is first reverse transcribed into cDNA, which is subjected to PCR amplification. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

In order to create phage-display libraries, the PCR repertoire products may be combined with linker oligos to generate scFv libraries to clone directly in frame with m13 pIII protein, following procedures known in the art. Libraries using other display techniques, such as those discussed above, can be prepared by methods well known in the art.

In a typical protocol, whole RNA is extracted by Tri BD reagent (Sigma) from fresh or RNAlater stabilized tissue. Subsequently, the isolated donor total RNA is further purified to mRNA using Oligotex purification (Qiagen). Next first strand cDNA synthesis, is generated by using random nonamer oligonucleotides and or oligo $(dT)_{18}$ primers (SEQ ID NO: 1) according to the protocol of AccuScript reverse transcriptase (Stratagene). Briefly, 100 ng mRNA, 0.5 mM dNTPs and 300 ng random nonamers and or 500 ng oligo $(dT)_{18}$ primers (SEQ ID NO: 1) in Accuscript RT buffer (Stratagene) are incubated at 65° C. for 5 mM, followed by rapid cooling to 4° C. Then, 100 mM DTT, Accuscript RT, and RNAse Block are added to each reaction and incubated at 42° C. for 1 h, and the reverse transcriptase is inactivated by heating at 70° C. for 15 minutes. The cDNA obtained can be used as a template for RT-PCR amplification of the antibody heavy and light chain V genes, which can then be cloned into a vector, or, if phage display library is intended, into a phagemid vector. This procedure generates a repertoire of antibody heavy and light chain variable region clones ($V_H$ and $V_L$ libraries), which can be kept separate or combined for screening purposes. The vector, such as a phagemid vector, can then be introduced into a host cell, such as an *E. coli* host, to generate a vector collection comprising a repertoire of nucleic acid molecules encoding antibody light chains or heavy chains or fragments thereof. In each case, the vector collection may comprise a single or more than one antibody light chain or heavy chain subtype. Thus, the vector collection may comprise sequences encoding antibody κ and/or λ light chains.

In the methods of the present invention, typically antibody light chains and antibody heavy chains are at first cloned separately, as discussed above, also separating the κ and λ light chain libraries. The libraries can be archived, and, when needed, the heavy chain library can be combined with the segregated κ and λ light chain libraries and heavy and light chain pairings can be identified, e.g. by panning, in the case of phage display. It is possible to repeat these steps multiple times with various libraries or sub-libraries, depending on the goal to be attained. The methods of the present invention provide great flexibility in including or excluding libraries, sub-libraries or clones, as needed during panning in order to maximize success.

In particular, because the sequences present in the vector collection harbor the coding sequences of the antibody heavy and light chains (or fragments) separately, the sequences may be excised and inserted into one or more expression vectors for expression of the antibody heavy and light chains, or fragments thereof. Preferably, the coding sequences of the antibody heavy and light chains, or fragments thereof, are inserted into the same expression vector for coexpression of the heavy and light chains to produce the library of the antibodies or antibody fragments.

The expression vectors of the present invention contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the antibodies-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the antibody-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding antibodies Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Transcription of the heavy chain or light chain genes in the expression vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the antibody genes by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antibody coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody heavy and light chains.

Still other methods, vectors, and host cells suitable for adaptation to the synthesis of polypeptide, in recombinant vertebrate cell culture are described in Gething et al., Nature, 293:620-625 (1981); Mantei et al., Nature, 281:40-46 (1979); EP 117,060; and EP 117,058.

In a particular embodiment, the antibody library is produced in the form of a phage library, where the coding sequences of the antibody heavy and light chains, or fragments thereof, are cloned into a phagemid vector, such as a vector comprising the bacteriophage gene III. Phagemid vectors are well known and commercially available, including, for example, the pBluescript vector SKII+ (Stratagene, Genbank Accession X52328), and other pBluescript vectors. Phage display technology enables the generation of large repertoires of human antibodies, and the biopanning procedure allows the selection of individual antibodies with any desired specificity or other properties.

For example, immunoglobulin repertoires from peripheral lymphocytes of survivors of earlier epidemics and pandemics, such as the 1918 Spanish Flu, can be retrieved, stabilized, rescued and expressed in a manner similar to that described above. For additional H1 and H3 libraries, repertoires can be recovered from properly timed vaccinated locally-sourced donors. As an additional option, commercially available bone marrow total RNA or mRNA can be purchased from commercial sources to produce libraries suitable for H1 and H3, and, depending upon the background of donor, also suitable for H2 antibody screening. In general, for target diseases where vaccination is an available treatment option, antibodies can be isolated from biological samples obtained from immunized human donors as well. From immunized patients that have developed titers of antibody recognizing the particular antigen, bone marrow, blood, or another source of lymphocytes, is collected, and antibodies produced are isolated, amplified and expressed as described above.

As discussed above, for each donor, antibody light and heavy chain libraries can be cloned separately. Thus, for each donor, various κ and λ light chain families can be separately pooled and cloned in equimolar amounts. Similarly, for each donor, various heavy chain families can be pooled and cloned in equimolar amounts. By enabling gene family specific rescue of antibodies, the methods of the present invention yield libraries more completely representing the antibody repertoire of the donor, including antibodies that are less abundant and, in the case of pooled antibody libraries, guaranteeing immunoglobulin contributions from any and all individuals. For example, as illustrated in Example 1 by the Examples, in preparing the influenza heavy and light chain libraries herein, 6 κ light chain families, 11λ light chain families and 4 heavy chain families were rescued.

A typical screen can yield zero, one, or more than one target specific positive clone(s). If a particular combinatorial antibody library or libraries have been exhaustively screened and no further solutions seem attainable this may not be a failure of the heavy and light chain repertoire(s) ability to bind target, but rather the collection may have failed to bring together the necessary heavy and light chain pair required to bind target. A typical rescued repertoire of light chains from any individual may contain between about $10^5$-$10^6$ unique light chains and between about $10^6$-$10^8$ unique heavy chains. The possible combinatorial products of such pairings range from $10^{11}$ to $10^{14}$. Such a collection exceeds the practical limits of most display systems, such as phage display, by several orders of magnitude. Consequently, with current display technologies (such as phage display), only a fraction of the combinatorial possibilities are captured and assessed in any single phage antibody library. Therefore, recloning the original set of heavy chains with the original collection of light chains will generate an entirely new set of shuffled heavy and light chain combinations with likely novel antibodies to a particular target. Such newly reshuffled collections were found to transform previously existing poorly performing donor specific libraries into highly productive collections. Specifically, for a collection from a single donor previously only 0.3x-fold enrichment could be achieved compared to background after three rounds of selection. However, when this collection was recloned and reshuffled it became capable of 15-fold enrichment following 3 rounds of panning resulting in 55 novel sequences from 92 selected clones.

As mentioned previously, a typical screen can yield any number of target specific positive clones. The present invention enables the identification of the origins of any clone by their embedded barcode. As a typical antibody screen may combine phage antibodies from numerous donor specific libraries it is possible that some of the libraries and their combinatorial clones are not completely represented as antibody bearing phage particles. In which case a positive clone may have resulted from only a limited physical set of all the possible cloned solutions present in the sub-library phage population being screened. In such an instance it is of considerable interest to more fully interrogate the collection of donor specific phage. In this case the barcode from a positive clone guides one to the specific library responsible for the clone and allows to exclusively and more deeply screen the collection of interest.

In instances where desired antibodies must have functional capabilities beyond those initially used as the basis for the initial library construction, such as neutralization, or activation, we can prospectively profile individual donor sera for evidence of such activities. If the desired activities are present at reasonable titers in any particular donor sera, one can select those corresponding libraries are selected to screen against the target of interest. In other instances the relevant selection criteria may be unrelated to serology, but related to donor characteristics such as age, gender, or medical histories. In any event, donor profiles are logical guides for library selection and possible only in donor specific and segregated antibody libraries.

It is not unusual to complete a phage panning screen and discover the presence of immunodominant clones. Furthermore, it is also not unusual to rediscover such clone upon repeated panning screening regimens. In the case of a dominant clone or clones, where either more or different clones are desirable, it is important to avoid the library material responsible for the presence of this clone. In typical phage antibody libraries the specific library or materials responsible for the clones origin are not separable from the collection, however in donor specific libraries it is possible to rescreen the libraries and simply omit the undesirable donor sublibrary or sublibraries, thereby forcing positive selection away from previously identified dominant clones.

Although, for simplicity, the libraries are described as heavy or light chain libraries, it will be apparent to those of ordinary skill in the art that the same description applies to the libraries of antibody fragments, fragments of antibody heavy and/or light chains, and libraries of antibody-like molecules.

In a particular embodiment, antibodies with dual specificities, such as, for example, showing reactivity with two different influenza A subtypes and/or with two strains (isolates) of the same subtype, and/or with human and non-human isolates, can be discovered and optimized through controlled cross-reactive selection and/or directed combinatorial and/or mutagenic engineering.

Figure 2:
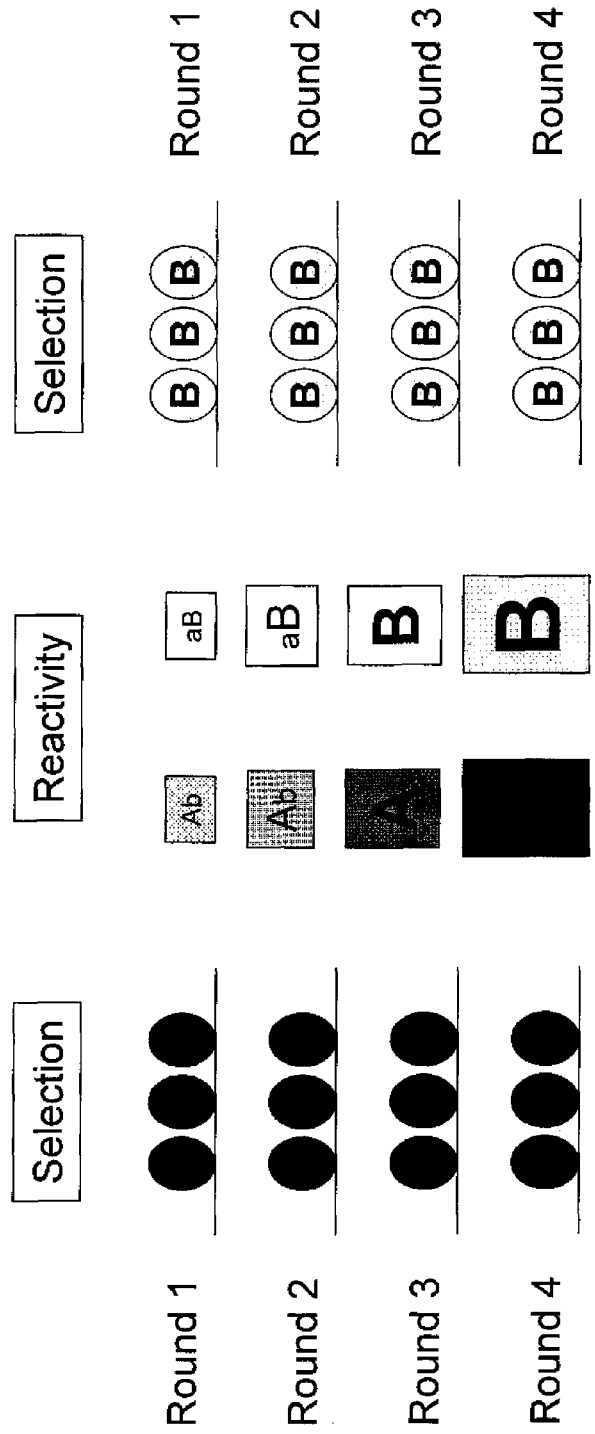
FIG. 2 illustrates a typical panning enrichment scheme for increasing the reactive strength towards two different targets, A and B. Each round of enrichment increases the reactive strength of the pool towards the individual target(s).
Figure 3:
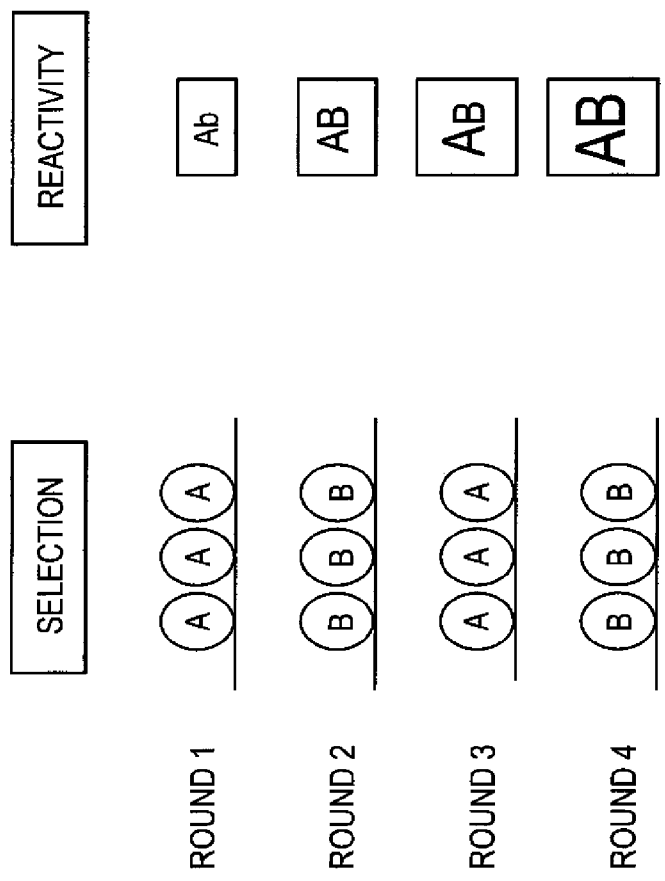
FIG. 3 illustrates a strategy for the selection of clones cross-reactive with targets A and B, in which each successive round reinforces the reactive strength of the resulting pool towards both targets.
Figure 4:
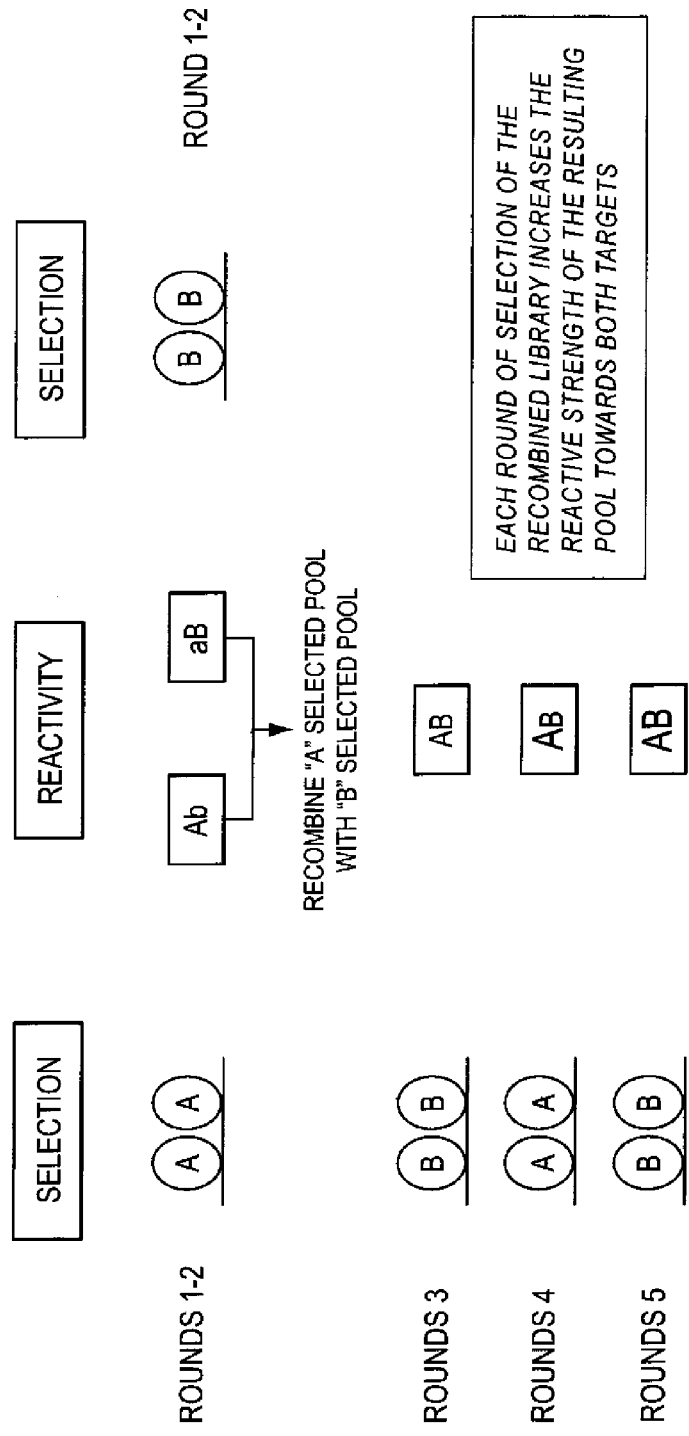
FIG. 4 illustrates a strategy for increasing the reactive strengths towards two different targets (targets A and B), by recombining parallel discovery pools to generate/increase cross-reactivity. Each round of selection of the recombined antibody library increases the reactive strength of the resulting pool towards both targets.
Figure 5:
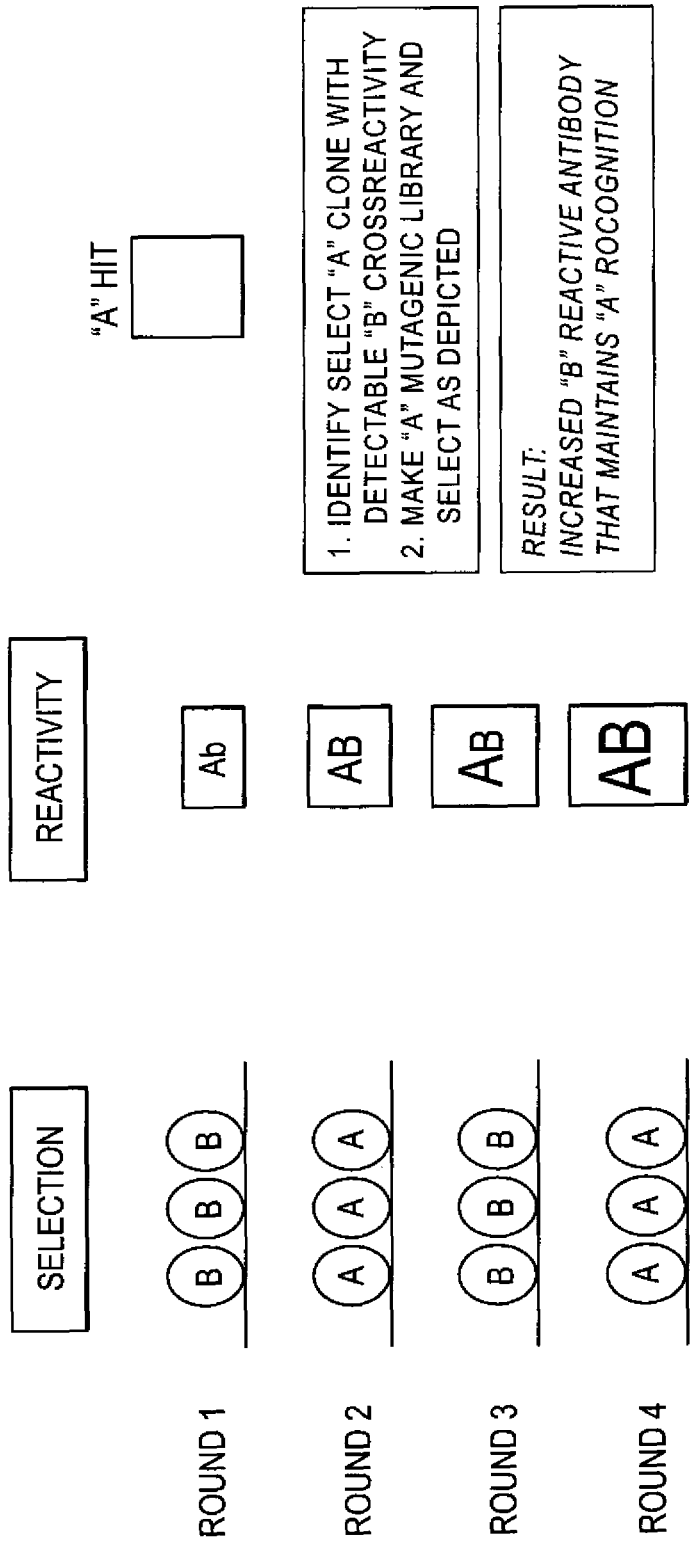
FIG. 5 illustrates a strategy for increasing cross-reactivity to a target B while maintaining reactivity to a target A. First, a clone reactive with target A is selected, then a mutagenic library of the clones reactive with target A is prepared, and selection is performed as shown, yielding one or more antibody clones that show strong reactivity with both target A and target B.

In a typical enrichment scheme, illustrated in FIG. 2, a library including antibodies showing cross-reactivity to two targets, designated as targets A and B, are subjected to multiple rounds of enrichment. If enrichment is based on reactivity with target A, each round of enrichment will increase the reactive strength of the pool towards target A. Similarly, if enrichment is based on reactivity with target B, each round of enrichment will increase the reactive strength of the pool towards target B. Although FIG. 2 refers to panning, which is the selection method used when screening phage display libraries (see below), the approach is equally applicable to any type of library discussed above, or otherwise known in the art, and to any type of display technique. Targets A and B include any targets to which antibodies bind, including but not limited to various isolates, types and sub-types of influenza viruses.

If the goal is to identify neutralizing antibodies with multiple specificities, a cross-reactive discovery selection scheme can be used. In the interest of simplicity, this scheme is illustrated in FIG. 3 showing the selection of antibodies with dual specificities. In this case, an antibody library including antibodies showing reactivity with two targets, targets A and B, is first selected for reactivity with one of the targets, e.g., target A, followed by selection for reactivity with the other target, e.g., target B. Each successive selection round reinforces the reactive strength of the resulting pool towards both targets. Accordingly, this method is particularly useful for identifying antibodies with dual specificity. Of course, the method can be extended to identifying antibodies showing reactivity towards further targets, by including additional rounds of enrichment towards the additional target(s). Again, if the library screened is a phage display library, selection is performed by cross-reactive panning, but other libraries and other selection methods can also be used.

A combination of the two methods discussed above includes two separate enrichment rounds for reactivity towards target A and target B, respectively, recombining the two pools obtained, and subsequent cross-reactive selection rounds, as described above. This approach is illustrated in FIG. 4. Just as in the pure cross-reactive selection, each round of selection of the recombined library increases the reactive strength of the resulting pool towards both targets.

In a further embodiment, illustrated in FIG. 5, first a clone showing strong reactivity with a target A, and having detectable cross-reactivity with target B is identified. Based on this clone, a mutagenic library is prepared, which is then selected, in alternating rounds, for reactivity with target B and target A respectively. This scheme will result in antibodies that maintain strong reactivity with target A, and have increased reactivity with target B. Just as before, selection is performed by panning, if the libraries screened are phage display libraries, but other libraries, other display techniques, and other selection methods can also be used, following the same strategy.

As discussed above, targets A and B can, for example, be two different subtypes of the influenza A virus, two different strains (isolates) of the same influenza A virus, subtypes or isolates from two different species, where one species is preferably human. Thus, for example, target A may be an isolate of the 2004 Vietnam isolate of the H5N1 virus, and target B may be a 1997 Hong Kong isolate of the H5N1 virus.

It is emphasized that these examples are merely illustrative, and antibodies with dual and multiple specificities to any two or multiple targets can be identified, selected and optimized in an analogous manner.

Once neutralizing antibodies with the desired properties have been identified, it might be desirable to identify the dominant epitope or epitopes recognized by the majority of such antibodies. Methods for epitope mapping are well known in the art and are disclosed, for example, in Morris, Glenn E., *Epitope Mapping Protocols*, Totowa, N.J. ed., Humana Press, 1996; and *Epitope Mapping: A Practical Approach*, Westwood and Hay, eds., Oxford University Press, 2001.

II. Identifying Donor-Specific Antibody Library with Unique Barcoding

According to the present invention, following amplification of the antibody heavy and light chain repertoires from cDNA, such as bone marrow cDNA, prepared as described above, preferably antibody heavy and light chain libraries are cloned separately for each patient donor, where the individual libraries can be distinguished using unique barcodes.

The barcodes preferably are selected such that they are capable of propagating along with the clone(s) labeled, without interfering with the expression of the desired antibody chain or fragment thereof. In an exemplary embodiment of the present invention, the barcode is inserted into the sequence of the expression vector, preferably, the 3' untranslated region following the terminal pIII stop codon when a phagemid vector is used. Upon clonal isolation, a vector's unique sequence is determined and subsequently dedicated to a single defined library. This defined library can be derived not only from a single donor, but also from discrete pools of donors, or a synthetic repertoire or a semi-synthetic collection. In another embodiment, the barcode is inserted into the coding sequence of the antibody heavy and/or light chain or fragment thereof, at a position or in a form that does not interfere with the expression of the respective chains.

Thus the barcodes can be non-coding DNA sequences of about 1-24 contiguous non-coding nucleotides in length that can be deconvoluted by sequencing or specific PCR primers. This way, a collection of nucleic acids, such as an antibody repertoire, can be linked at the cloning step. In a exemplary embodiment of the present invention, the barcode is 3 or 5 bases of randomly generated sequence.

In another example, the barcodes are coding sequences of silent mutations. If the libraries utilize restriction enzymes that recognize interrupted palidromes (e.g. Sfi GGCC GGCC (SEQ ID NO: 2)), distinct nucleotides can be incorporated in place of the "N's" to distinguish various collections of clones, such as antibody libraries. This barcoding approach has the advantage that the repertoire is linked at the amplification step.

In a further embodiment, the barcodes are non-contiguous nucleotide sequences, which may be present in the vector sequence and/or the coding sequence of the desired antibody chain. Thus, a barcode with a non-contiguous sequence provides a great degree of flexibility in identifying the origins of the various individual sequences, and monitoring their subsequent handling.

In a different example, the barcodes are coding sequences that encode immunologically distinct peptide or protein sequences fused to phage particles. Examples include, for example, epitope (e.g. Myc, HA, FLAG) fusions to pIII, pVIII, pVII, or pIX phages. The epitopes can be used singly or in various combinations, and can be provided in cis (on the library-encoding plasmid) or in trans (specifically modified helper phage) configuration.

Other examples of possible barcodes include, without limitation, chemical and enzymatic phage modifications (for phage libraries) with haptens or fluorescent chromophores. Such tags are preferred for a single round of selection.

The individual heavy and light chain libraries obtained from individual donors, or other barcoded clone or collections, can be pooled, without losing the ability to distinguish the source of individual sequences.

III. Optimizing Neutralizing Antibodies From the Donor-Specific Antibody Libraries If desired, cross-reactivity of the neutralizing antibodies with dual or multiple specificity can be further improved by methods known in the art, such as, for example, by Look Through Mutagenesis (LTM), as described in US. Patent Application Publication No. 20050136428, published Jun. 23, 2005, the entire disclosure of which is hereby expressly incorporated by reference.

Look-through mutagenesis (LTM) is a multidimensional mutagenesis method that simultaneously assesses and optimizes combinatorial mutations of selected amino acids. The process focuses on a precise distribution within one or more complementarity determining region (CDR) domains and explores the synergistic contribution of amino acid side-chain chemistry. LTM generates a positional series of single mutations within a CDR where each wild type residue is systematically substituted by one of a number of selected amino acids. Mutated CDRs are combined to generate combinatorial single-chain variable fragment (scFv) libraries of increasing complexity and size without becoming prohibitive to the quantitative display of all variants. After positive selection, clones with improved properties are sequenced, and those beneficial mutations are mapped. To identify synergistic mutations for improved binding properties, combinatorial libraries (combinatorial beneficial mutations, CBMs) expressing all beneficial permutations can be produced by mixed DNA probes, positively selected, and analyzed to identify a panel of optimized scFv candidates. The procedure can be performed in a similar manner with Fv and other antibody libraries.

Mutagenesis can also be performed by walk-through mutagenesis (WTM), as described above.

Another useful mutagenic method to intentionally design cross-reactivity of the antibodies herein with more than one influenza A subtype and/or more than one isolate of the same subtype, is referred herein as "destinational" mutagenesis. Destinational mutagenesis can be used to rationally engineer a collection of antibodies based upon one or more antibody clones, preferably of differing reactivities. In the context of the present invention, destinational mutagenesis is used to encode single or multiple residues defined by analogous positions on like sequences such as those in the individual CDRs of antibodies. In this case, these collections are generated using oligo degeneracy to capture the range of residues found in the comparable positions. It is expected that within this collection a continuum of specificities will exist between or even beyond those of the parental clones. The objective of destinational mutagenesis is to generate diverse multifunctional antibody collections, or libraries, between two or more discrete entities or collections. To create a destinational mutagenesis library, the CDR sequences for both antibodies are first attained and aligned. Next all positions of conserved identity are fixed with a single codon to the matched residue. At non-conserved positions a degenerate codon is incorporated to encode both residues. In some instances the degenerate codon will only encode the two parental residues at this position. However, in some instances additional co-products are produced. The level of co-product production can be dialed in to force co-product production or eliminate this production dependent upon size limits or goals.

Thus, for example, if the first position of the two antibodies respectively are threonine and alanine, the degenerate codon with A/G-C- in the first two positions would only encode threonine or alanine, irrespective of the base in the third position. If, for example, the next position residues are lysine and arginine the degenerate codon A-A/G-A/G will only encode lysine or arginine. However, if the degenerate codon A/C-A/G-A/G/C/T were used then asparagine, histidine, glutamine, and serine coproducts will be generated as well.

As a convenience it is simpler to use only antibodies with matched CDR lengths. One way to force this is to screen a size restricted library for the second antigen, based on the CDR length and potentially even framework restrictions imparted by the initially discovered antibody. It is noted, however, that using CDRs of equal length is only a convenience and not a requirement. It is easy to see that, while this method will be useful to create large functionally diverse libraries of influenza A virus neutralizing antibodies, its applicability is much broader. This mutagenesis technique can be used to produce functionally diverse libraries or collections of any antibody. Thus, FIG. 6 is included herein to illustrate the use of the destinational mutagenesis method using CDRs of a TNF-α antibody and a CD11a antibody as the parental sequences mutagenized.

Other exemplary mutagenesis methods include saturation mutagenesis and error prone PCR.

Saturation mutagenesis (Hayashi et al., *Biotechniques* 17:310-315 (1994)) is a technique in which all 20 amino acids are substituted in a particular position in a protein and clones corresponding to each variant are assayed for a particular phenotype. (See, also U.S. Pat. Nos. 6,171,820; 6,358,709 and 6,361,974.)

Error prone PCR (Leung et al., *Technique* 1:11-15 (1989); Cadwell and Joyce, *PCR Method Applic.* 2:28-33 (1992)) is a modified polymerase chain reaction (PCR) technique introducing random point mutations into cloned genes. The resulting PCR products can be cloned to produce random mutant libraries or transcribed directly if a T7 promoter is incorporated within the appropriate PCR primer.

Other mutagenesis techniques are also well known and described, for example, in *In Vitro Mutagenesis Protocols*, J. Braman, Ed., Humana Press, 2001.

Optimization can be based on any of the libraries discussed above, or any other types of libraries known in the art, alone or in any combination.

IV. Production of Neutralizing Antibodies

Once antibodies with the desired neutralizing properties are identified, such antibodies, including antibody fragments can be produced by methods well known in the art, including, for example, hybridoma techniques or recombinant DNA technology.

In the hybridoma method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Recombinant monoclonal antibodies can, for example, be produced by isolating the DNA encoding the required antibody chains and co-transfecting a recombinant host cell with the coding sequences for co-expression, using well known recombinant expression vectors. Recombinant host cells can be prokaryotic and eukaryotic cells, such as those described above.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.* 151:2296 (1993); Chothia et al., *J. Mol. Biol.* 196:901 (1987)). It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences.

In addition, human antibodies can be generated following methods known in the art. For example, transgenic animals (e.g., mice) can be made that are capable, upon immunization, of producing a full repertoire of human antibodies in the absence of endogenous immunoglobulin production. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669, 5,589,369 and 5,545,807.

V. Use of Neutralizing Antibodies

The neutralizing antibodies of the present invention can be used for the prevention and/or treatment of the targeted diseases. For therapeutic applications, the antibodies or other molecules, the delivery of which is facilitated by using the antibodies or antibody-based transport sequences, are usually used in the form of pharmaceutical compositions. Techniques and formulations generally may be found in *Remington's Pharmaceutical Sciences,* 18th Edition, Mack Publishing Co. (Easton, Pa. 1990). See also, Wang and Hanson "Parenteral Formulations of Proteins and Peptides: Stability and Stabilizers," *Journal of Parenteral Science and Technology,* Technical Report No. 10, Supp. 42-2S (1988).

Antibodies are typically formulated in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, supra.

The neutralizing antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

For the prevention or treatment of disease, the appropriate dosage of antibody will depend on the type of infection to be treated, the severity and course of the disease, and whether the antibody is administered for preventive or therapeutic purposes. The antibody is suitably administered to the patient at one time or over a series of treatments. Depending on the type and severity of the disease, about 1 µg/kg to about 15 mg/kg of antibody is a typical initial candidate dosage for administration to the patient, whether, for example, by one or more separate administrations, or by continuous infusion.

Further details of the invention are illustrated by the following non-limiting Examples.

EXAMPLE 1

Antibody Libraries from Survivors of Prior Bird Flu Outbreaks and Preparation of Neutralizing Antibodies Materials and Methods Bone Marrow Protocol and Sera Preparation Blood was obtained by standard venopuncture, allowed to clot, and processed to recover serum. The serum was stored at −20° C. for 3-4 days until they were shipped on dry ice. Donors were anaesthetized with an injection of a local anesthetic and 5 ml of bone marrow was removed from the pelvic bone of each H5N1 survivor. Next the 5 ml of bone marrow was placed into a sterile 50-ml tube containing 45 ml RNAlater (Ambion). The mixture was gently inverted approximately 8-20 times, until there were no visible clumps and the marrow and RNAlater were mixed well. Next the specimen was refrigerated the between 2-10° C. overnight. Following the overnight refrigeration, the specimens were stored at −20° C. for 3-4 days until they were shipped on dry ice. Upon receipt the RNAlater/marrow and sera containing tubes were stored at −80° C. until processed.

Serology: HA ELISA

ELISA plates (Thermo, Immulon 4HBX 96W) were coated with 100 μl of 100 ng/mL H5 hemagglutinin (Protein Sciences, A/Vietnam/1203/2004) in 1× ELISA Plate Coating Solution (BioFX) by overnight incubation at room temperature. The next day plates were washed three times with 300 μPBS/0.05% Tween-20 (PBST). Following the wash, 300 μl of a blocking solution (4% Non-Fat dry Milk in PBS/0.05% Tween-20) was added and incubated for 1 hour at RT. Following the blocking step, the plates were washed three times with 300 μl PBS/0.05% Tween-20. Next, 100 μl serum samples diluted 1:20,000 in PBS/0.05% Tween were incubated for 1-2 hours at RT and then washed three times with 300 μl PBS/0.05% Tween-20. 100 μl of an anti-human Fc-HRP conjugate diluted 1:5,000 in PBS/0.05% Tween was incubated for 1-2 hours at RT and then washed three times with 300 μl PBS/0.05% Tween-20. Following this final wash, 100 μl of chromogenic substrate solution was added (TMB1 Substrate, BioFx) and after sufficient amount of time terminated by the addition of 100 μl of STOP Solution (BioFx). Absorbances at 450 nm were read on a plate reader (Molecular Devices Thermomax microplate reader with Softmax Pro software), data recorded, and subsequently plotted using Excel (Microsoft).

Bone Marrow: RNA Extraction and mRNA Purification

Bone marrow (~2.5 ml in 20 ml RNA later), previously stored at −80° C., was recovered by centrifugation to remove RNA later and then resuspended in 11.25 ml TRI BD reagent (Sigma) containing 300 μl Acetic Acid. The pellet was then vortexed vigorously. Next 1.5 ml BCP (1-bromo-3-chloropropane, Sigma) was added, mixed by vortexing, incubated at RT for 5 min, and then centrifuged at 12000×g for 15 min at 4° C. The aqueous phase was carefully removed to not disturb the interface. Total RNA from the aqueous phase was next precipitated by addition of 25 ml isopropanol, incubation at RT for 10 minutes, and centrifugation at 12000×g for 10 min at 4° C. Following the addition of isopropanol, two phases were formed due to residual RNAlater, resulting in the precipitated RNA settling at the interface. To eliminate the residual RNAlater and allow maximal recovery of RNA, 5 ml aliquots of 50% isopropanol in $H_2O$ were added and mixed until no phase separation was noticeable, at which point the RNA was pelleted by centrifugation at 12000×g for 10 min at 4° C. The RNA pellet was washed with 75% EtOH, transferred to an RNAse-free 1.6 ml microcentrifuge tube, and again recovered by centrifugation. Finally the RNA pellet was resuspended in 100 μl 1 mM Na-phosphate, pH 8.2 and the $A_{260}$ and $A_{280}$ were read to assess RNA purity.

Prior to reverse transcription mRNA was purified from total RNA according to Qiagen Oligotex mRNA purification kit. Briefly, 50-200 μg bone marrow RNA was brought to 250 μA with RNase-free water and mixed with 250 μA of OBB buffer and Oligotex suspension followed by incubation for 3 min at 70° C. Hybridization between the oligo $dT_{30}$ (SEQ ID NO: 3) of the Oligotex particle and the mRNA poly-A-tail was carried out at room temperature for 10 min. The hybridized suspensions were then transferred to a spin column and centrifuged for 1 min. The spin column was washed twice with 400 μl Buffer OW2. Purified mRNA was then eluted twice by centrifugation with 20 W hot (70° C.) Buffer OEB. Typical yields were 500 ng to 1.5 μg total RNA.

Reverse Transcription Using N9 and Oligo dT on Bone Marrow mRNA

Reverse transcription (RT) reactions were accomplished by mixing together 75-100 ng mRNA with 2 μl 10× AccuScript RT Buffer (Stratagene), 0.8 μl 100 mM dNTPs, and either N9 (300 ng) or oligo dT primer (100 ng) and then brought to a final volume of 17 μl with water. The mixtures were heated at 65° C. for 5 min, and then allowed to cool to room temperature. Next 2 μl DTT, 0.5 μl RNase Block (Stratagene), 0.5 μl AccuScript RT (Stratagene) were added to each reaction. Next, the N9 primed reactions were incubated for 10 minutes at room temperature and the oligo-dT primed reactions were incubated on ice for 10 minutes. Finally, both reactions were incubated at 42° C. for 60 minutes followed by 70° C. for 15 minutes to kill the enzyme.

PCR from Bone Marrow-Derived cDNA

Antibody heavy and light chain repertoires were amplified from bone marrow cDNA essentially using previously described methods and degenerate primers (O'Brien, P. M., Aitken R. *Standard protocols for the construction of scFv Libraries. Antibody Phage Display—Methods and Protocols*, vol. 178, 59-71, 2001, Humana Press) based upon human germline V and J regions.

Briefly, PCR reactions using Oligo dT primed cDNA (from 75 ng mRNA) for lambda light chains and N9 primed cDNA (from 75 ng mRNA for kappa light chains, from 100 ng mRNA for heavy chains) were mixed together with 5 μl 10× amplification buffer (Invitrogen), 1.5 μl dNTPs (10 mM), 1 μl MgSO4 (50 mM), 2.5 μl $V_{region}$ primers (10 uM) and 2.5 μl $J_{region}$ primers (10 uM)-10 uM for $V_H$, 0.5 μl Platinum Pfx Polymerase (Invitrogen), and sterile $dH_2O$ to final volume of 50 μl. PCR parameters were as follows: step 1-95° C. 5 minutes, step 2-95° C. 30 seconds, step 3-58° C. 30 seconds, step 4-68° C. 1 minute, step 5-cycle step 2-4 40 times, step 6-68° C. 5 minutes. Light chain PCR products were cleaned up using Qiagen PCR Cleanup kit. Heavy chains PCR products were gel purified from 1.5% agarose gel using Qiagen Gel Extraction Kit and then reamplified. Heavy chain reamplification was carried out as follows: Mixed 10 μl 10× amplification buffer (Invitrogen), 3 μl dNTPs (10 mM), 2 μl MgSO4 (50 mM), 5 μl each $V_H$ primers (10 uM) and $J_H$ primers (10 uM), 5 μl Heavy chain Primary PCR product, 1 μl Platinum Pfx, volume adjusted to 100 μl with water. Cycling parameters were as follows: step 1-95° C. 5 minutes, step 2-95° C. 30 seconds, step 3-58° C. 30 seconds, step 4-68° C. 1 minute, step 5-cycle step 2-4 20 times, step 6-68° C. 5 minutes. Re-amplified heavy chain PCR products were cleaned up from a 1.5% agarose-TAE gel using Qiagen Extraction Kit.

Antibody Phase Library Construction

Separate antibody libraries for each individual bird flu survivor were constructed using unique identifying 3-nucleotide barcodes inserted in the untranslated region following the stop codon of the pIII gene of filamentous phage.

Light Chain Cloning:

1 μg each of pooled kappa light chain and pooled lambda light chain per donor were digested with NotI and BamHI and gel purified from a 1.5% agarose-TAE gel using Qiagen Gel Extraction Kit. 5 μg of each vector (pAMPFab) was digested with NotI and BamHI and gel purified from a 1% agarose-TAE gel using Qiagen Gel Extraction Kit. Library ligations were performed with 200 ng of gel purified Kappa or Lambda inserts and 1 μg of gel purified vector in 60 μl for 1 hour at RT or overnight at 14° C. Ligations were desalted using Edge BioSystem Perfroma spin columns. The library was transformed in five electroporations in 80 μl TG-1 or XL-1 Blue aliquots, each recovered in 1 ml SOC, pooled and outgrown for one hour at 37° C. Total number of transformants was determined following this outgrowth by plating an aliquot from each of the transformations. The remaining electroporation was amplified by growing overnight at 37° C. in 200 ml 2YT+50 μg/ml Ampicillin+2% glucose. The subsequent light chain library was recovered by plasmid purification from these overnight cultures using a Qiagen High Speed Maxiprep Kit.

Heavy Chain Cloning:

1.5-2 μg each of the donor-specific heavy chains ($V_H1$, $V_H$ 2, 5, 6 pool, $V_H$ 3, and $V_H$ 4) were digested with a 40 Unit excess/μg DNA with SfiI and XhoI and gel purified from a 1.5% agarose-TAE gel using Qiagen Gel Extraction Kit. 15 μg of each light chain library vector was digested with 40 Unit/μg DNA with SfiI and XhoI and gel purified from a 1% agarose-TAE gel using Qiagen Gel Extraction Kit. Library ligations were set up by combining 1.2 μg SfiI/XhoI digested, gel purified heavy chain donor collections and 5 μg of each light chain library (kappa and lambda) overnight at 14° C. The library ligations were then desalted with Edge BioSystem Pefroma spin columns and then transformed through 20 electroporations per library in 80 μl TG-1 aliquots, each recovered in 1 ml SOC, pooled and outgrown for one hour at 37° C. Again following this outgrowth an aliquot of each was used to determine the total number of transformants with the remainder transferred to 1 L 2YT+50 μg/ml Ampicillin+2% glucose and grown at 37 C with vigorous aeration to an $OD_{600}$ of ~0.3. Next M13K07 helper phage was then added at a multiplicity of infection (MOI) of 5:1 and incubated for 1 hour at 37° C., with no agitation. Next the cells were harvested by centrifugation and resuspended in 1 L 2YT+50 μg/ml Ampicillin, 70 μg/ml Kanamycin and grown overnight at 37° C. with vigorous aeration to allow for scFv phagemid production. The next morning the cells were collected by centrifugation and supernatant containing phagemid was collected. The phagemids were precipitated from the supernatant by the addition of 0.2 volumes 20% PEG/5 M NaCl solution and incubation for 1 hour on ice. The phagemid library stocks were then harvested by centrifugation and resuspended in 20 ml sterile PBS. Residual bacteria were removed by an additional centrifugation and the final phagemid libraries were stored at −20° C. in PBS+50% glycerol.

Phagemid Panning and Amplification

ELISA plates (Immulon 4HBX flat bottom, Nunc) were coated with 100 μl of 100 ng/mL H5 hemagglutinin protein (Protein Sciences, A/Vietnam/1203/2004) in ELISA Coating Solution (BioFX) by overnight incubation at room temperature. The next day plates were washed three times with 300 μl PBST. Following the wash, 300 μl of a blocking solution (4% Non-Fat dry Milk in PBS/0.05% Tween-20) was added and incubated for 30 mins on ice. Following the blocking step, the plates were washed three times with 300 μl PBST. Just prior to phage panning, the glycerol was removed from the frozen phagemid stocks using Millipore Amicon Ultra columns and then blocked in 4% nonfat dry milk for 15 minutes. Next, 100 μl aliquots of phagemid were distributed into 8 wells (total phage ~$1\times10^{12}$ CFU) and incubated for 2 hours at 4° C. followed by washing 6-8 times with 300 μl PBST. Phagemid were collected following a 10 min at room temperature in 100 μl/well Elution buffer (0.2M glycine-HCl, pH 2.2, 1 mg/ml BSA). The eluate was then neutralized by the addition of 56.25 μl 2M Tris base per ml eluate. Following neutralization, 5 ml TG1 cells ($OD_{600}$~0.3) were infected with 0.5 ml neutralized phage at 37° C. for 30 minutes in 2-YT with no shaking. Following this step some cells were plated onto LB AMP Glucose plates to determine total phagemid recovery. The remaining inoculum was placed into 10 ml 2-YTAG (final concentration 2% glucose and 50 ug/ml ampicillin) and grown at 37° C. with vigorous aeration to $OD_{600}$~0.3. Next the cultures were infected with M13K07 helper phage at an MOI of 5:1 and incubated at 37° C. for 30-60 minutes with no shaking. The cells were collected by centrifugation and resuspended in 25 ml 2-YTAK (Ampicillin 50 μg/ml, Kanamycin 70 μg/ml), transferred to a fresh culture flask, and grown ON at 37° C. with shaking. Subsequent rounds were similarly recovered and amplified.

scFv ELISA

Individual colonies of *E. coli* HB2151 transformed cells from biopanned phage were grown overnight at 37° C. in 1 ml of 2YT+100 μg/ml AMP. The following morning the cells were harvested by centrifugation and resuspended in 1.5 ml periplasmic lysis buffer (1 ml BBS (Teknova)+0.5 ml 10 mg/ml lysozyme+EDTA to 10 mM final concentration). The cells were again pelleted by centrifugation and the scFv containing periplasmic lysates were collected. The scFv lysates were combined 1:1 with dilution buffer (PBS/0.05% BSA) and 100 μl was added to wells that had been previously antigen coated with and blocked with dilution buffer. The samples were incubated for 2 hours at room temperature and then washed three times with PBS/0.05% Tween. Next 100 μl of 1:5000 diluted Biotin Anti-Histidine mouse (Serotec) in dilution buffer was added to each well and incubated for 1 hr at room temperature. Following this incubation the wells were washed three times with PBS/0.05% Tween and then to each well 100 μl of 1:2500 Streptavidin:HRP (Serotec) was added and incubated for 1 hr at room temperature and then washed three times with PBS/0.05% Tween. Following this final wash, 100 μl of chromogenic substrate solution was added (TMB1 Substrate, BioFx) and after sufficient amount of time terminated by the addition of 100 μl of STOP Solution (BioFx). Absorbances at 450 nm were read on a plate reader (Molecular Devices Thermomax microplate reader with Softmax Pro software), data recorded, and subsequently plotted using Excel (Microsoft).

Sequencing

To deduce the heavy and light chain sequences, individual clones were grown and plasmid DNA extracted (Qiagen). The plasmid DNA was subjected to standard DNA sequencing.

Hemagglutinin Inhibition (HAI) Assays

Hemagglutination Inhibition was performed essentially following the method of Rogers et al., *Virology* 131:394-408 (1983), in round bottom microtiter plates (Corning) using 4 HAU (hemagglutinating units) of virus or protein/well. For HAI determinations 25 µl samples of purified single chain variable fragments (scFv) were mixed with 25 µl of PBS containing 4 HAU of the test virus in each microtiter well. Following a preincubation of 15 minutes at room temperature, 25 µl of 0.75% human erythrocytes were added, and mixed. HAI antibody activity was determined by visual inspection following a 60 min incubation at room temperature.

Results

Figure 8:
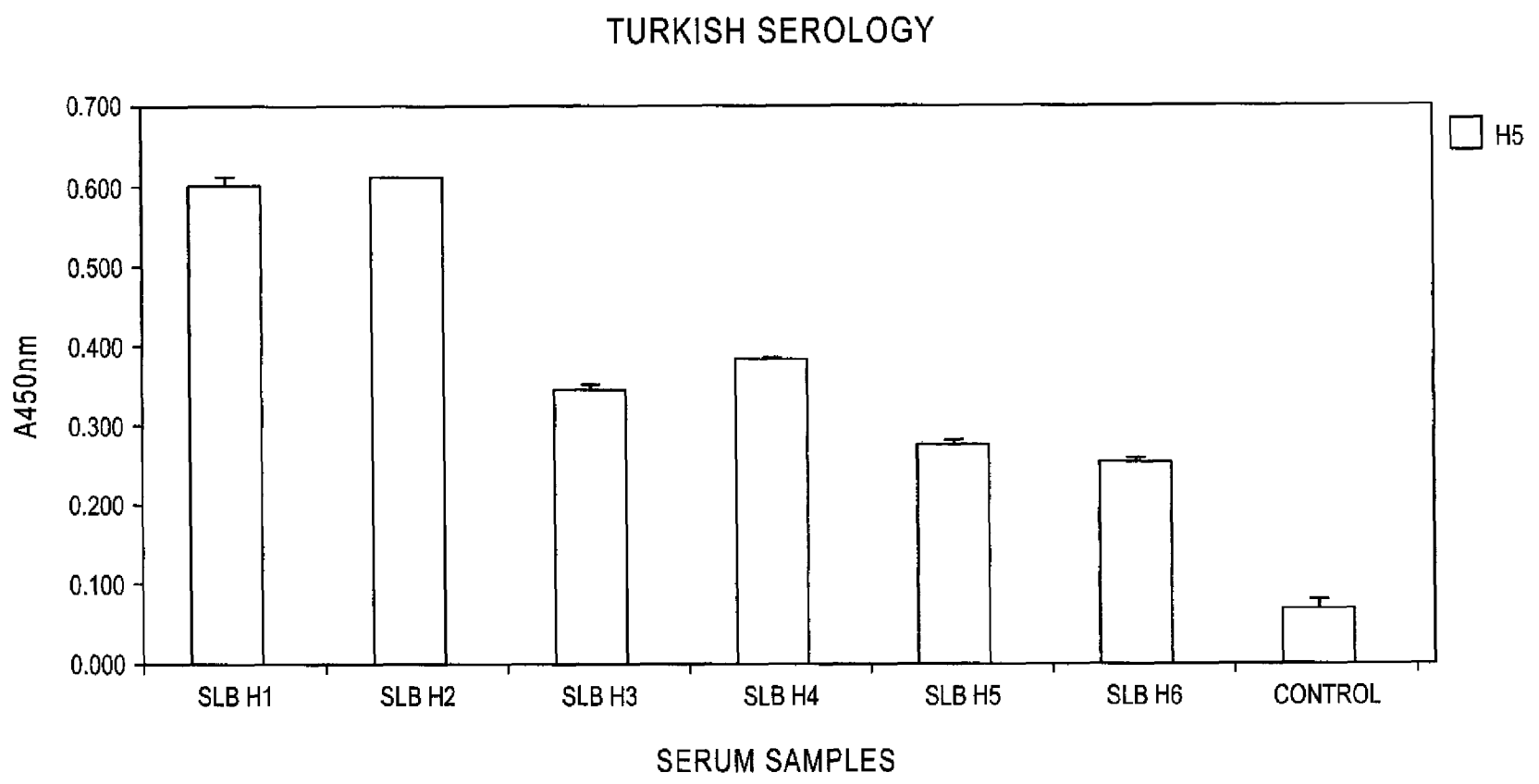

Bone marrow and blood samples were collected from six survivors of the H5N1 bird flu outbreak that had taken place in Turkey in January 2006, approximately four months after the outbreak. For all six survivors the initial diagnosis of bird flu was made following by physical examination, clinical laboratory testing, and molecular diagnostic determination, sanctioned by the Turkish Ministry of Health. Four of these survivors were additionally confirmed by the World Health Organization (WHO). Serum samples were analyzed to confirm the presence of antibodies to H5 hemagglutinin (A/Vietnam/1203/2004) using the serology protocol described above. As shown in FIG. 8, the blood samples of all six patients (designated SLB H1-H6, respectively) demonstrated the presence of antibodies to the H5 antigen. Following this confirmation, RNA was extracted from the bone marrow samples of these individuals, and bone marrow mRNA was purified and reverse transcribed using the protocols described above. The antibody heavy and light chain repertoires were then amplified from the bone marrow cDNA as described above, and individual antibody heavy and light chain phage libraries were cloned separately for each survivor, using the above-described three-nucleotide bar coding to distinguish the individual libraries.

Figure 9:
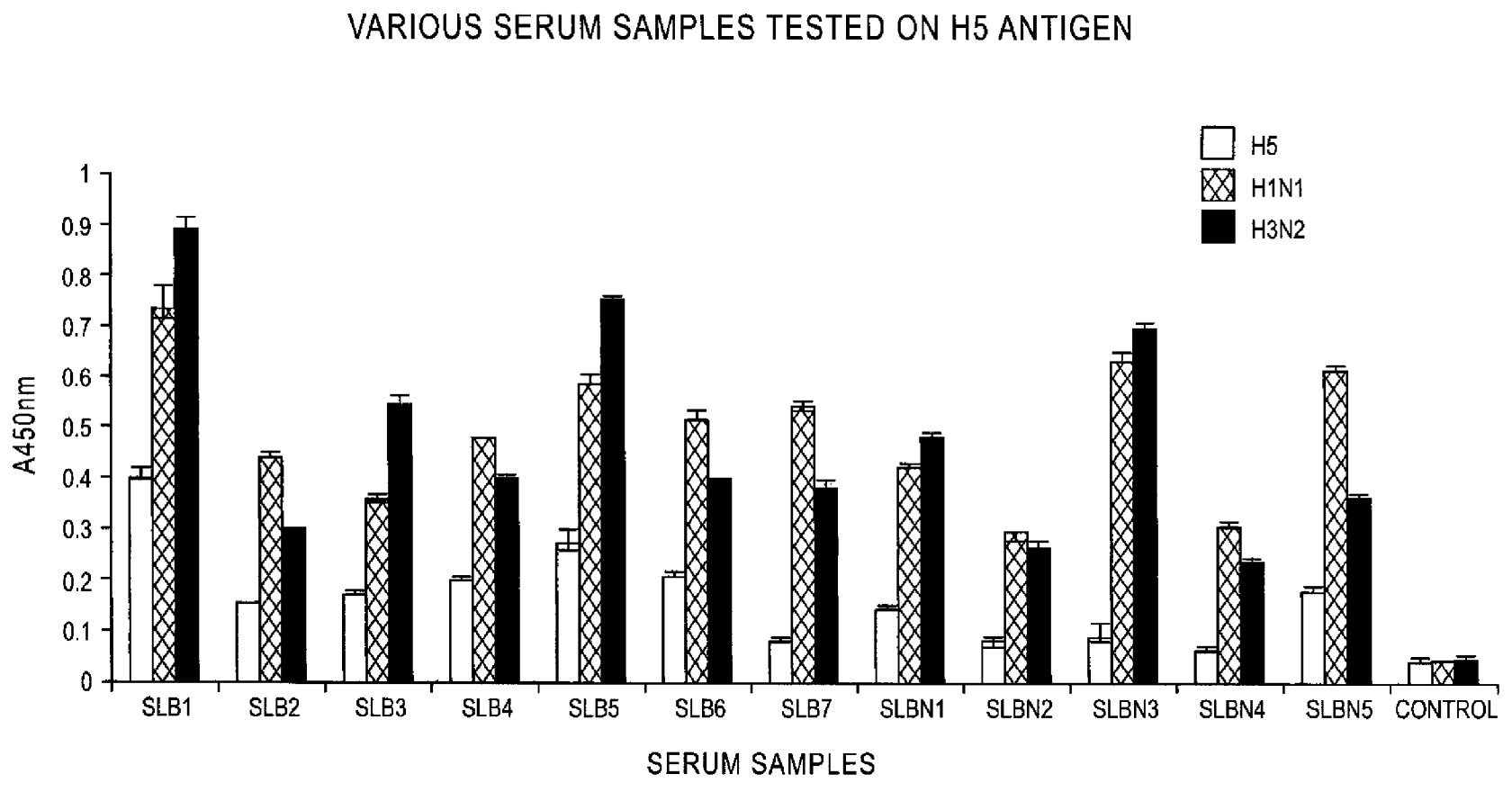

Bone marrow and blood samples were also collected from twelve local donors who were treated for flu symptoms in the year of 2006. Serology was performed as described above to confirm the presence of antibodies to H1, H3 and H5 hemagglutinin, respectively. As shown in FIG. 8, all serum samples tested positive for antibodies to H1 and/or H3 hemagglutinins, where the dominance of a certain subtype depended on the influenza A virus subtype to which the particular donor was exposed most throughout his or her lifetime. Interestingly, there were donors whose serum contained a significant level of antibodies of H5 hemagglutinin as well (donors SLB1 and SLB5 in FIG. 9). Following this confirmation, RNA was extracted from the bone marrow samples of the donors, and bone marrow mRNA was purified and reverse transcribed using the protocols described above. The antibody heavy and light chain repertoires were then amplified from the bone marrow cDNA as described above, and individual antibody heavy and light chain phage libraries were cloned separately for each donor, using the above-described three-nucleotide bar coding to distinguish the individual libraries.

Figure 10:
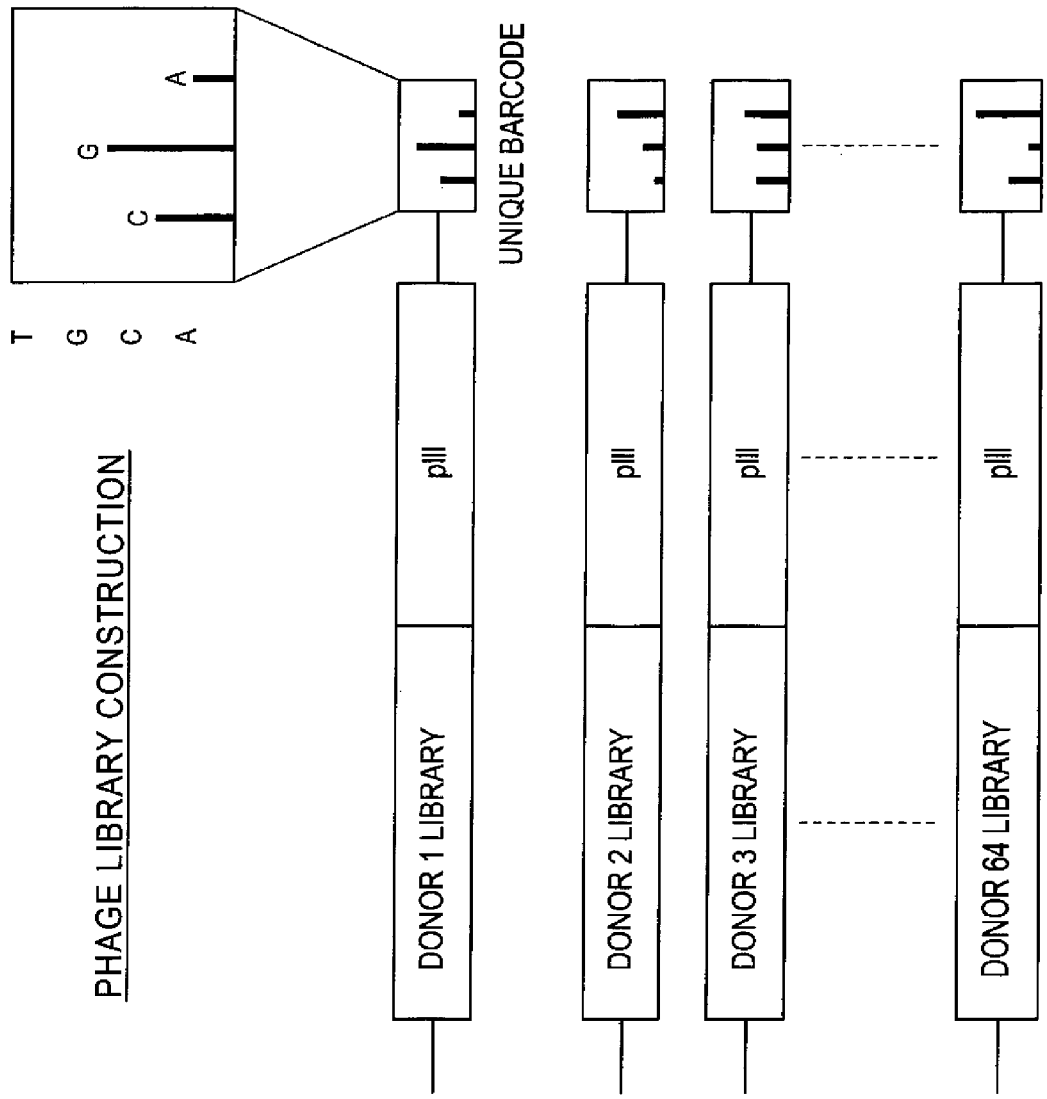
FIG. 10 illustrates the unique barcoding approach used in the construction of antibody phage libraries.

As illustrated in FIG. 10, using three of the available four nucleotides allows the creation of 64 unique barcodes.

Figure 11:
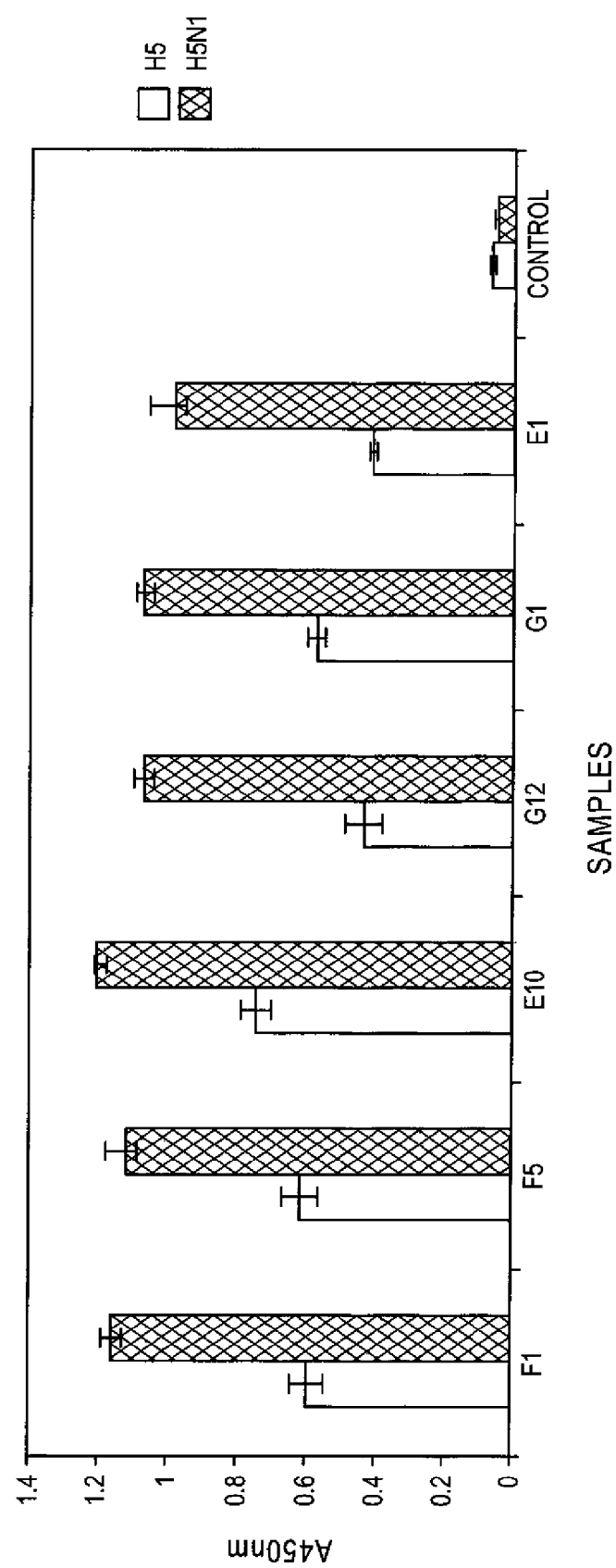
FIG. 11 shows the results of a scFv ELISA test of five distinct clones obtained from pooled libraries of Turkish bird flu survivors on H5 protein and H5N1 virus.

Out of 48 random clones obtained after three rounds of panning of pooled antibody libraries prepared from the bone marrow samples of Turkish bird flu survivors, 40 were tested by ELISA for binding to the H5 hemagglutinin protein (Protein Sciences, A/Vietnam/1203/2004), and to inactivated Vietnamese H5N1 virus (CBER, A/Vietnam/1203/2004). The clones were sequenced. Of the 40 clones, five were found to be different. As shown in FIG. 11, all five distinct clones (clones F5 and G1 have the same sequences) were binding both to the H5 protein and the Vietnamese H5N1 virus. FIG. 12 shows sequence alignments comparing the sequences of H5 hemagglutinin proteins from Turkish donors to the H5 hemagglutinin sequence of the Vietnamese isolate used in the above experiments. The results of these experiments show that, despite differences in the sequences, the antibodies tested bound both the Turkish and the Vietnamese H5 proteins and viruses, and thus showed cross-reactivity with more than one isolate of the H5N1 virus.

Four additional unique clones were identified from among 13 clones produced by the second round of panning.

Figure 13:

The heavy chain variable region sequences of the unique clones identified in the pooled antibody libraries of Turkish donors, along with the corresponding light chain and germline origin sequences, are shown in FIGS. 13 and 14. In particular, the sequences shown in FIG. 13 (3-23 heavy chain clones) originate from a pooled library of all heavy and light chains of all Turkish donors after three rounds of panning. The sequences shown in FIG. 14 (3-30 heavy chain clones) originate from a pooled library of all heavy and light chains of all Turkish donors after two rounds of panning.

Additional unique H5N1 specific antibody heavy chain variable region sequences were identified from antibody libraries of individual Turkish donors, using the ELISA protocol described above, after four rounds of panning. The sequences of these H5N1 ELISA positive clones are shown in FIGS. 15A-D.

FIGS. 16 and 17 illustrate the use of destinational mutagenesis to create diverse antibody heavy and light chain libraries using the antibody heavy (FIG. 16) and light chain (FIG. 17) sequences identified by analysis of sera and bone marrow of Turkish bird flu survivors as described above.

Figure 18:
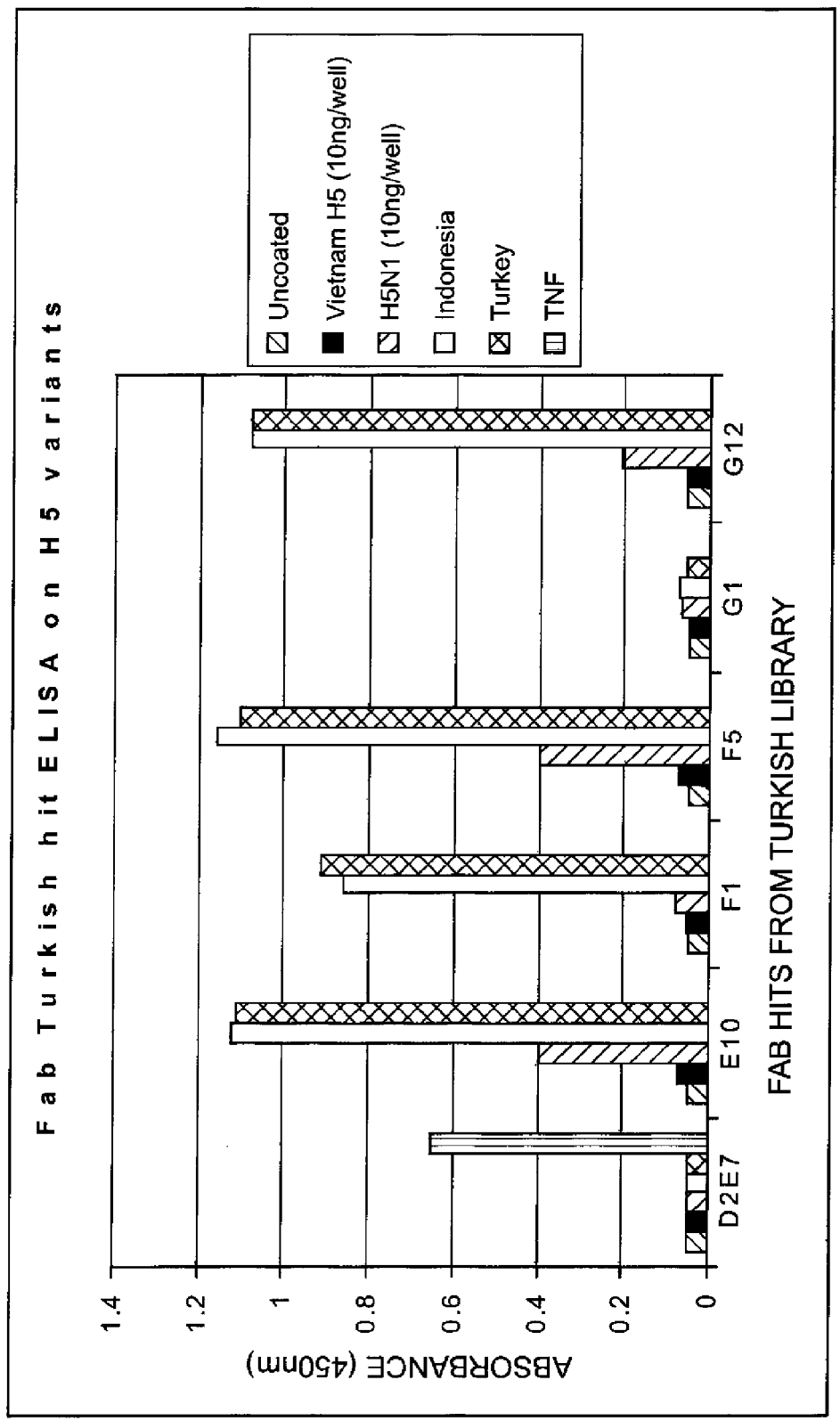
FIGS. 18 and 19 show ELISA results confirming cross-reactivity of certain Fab fragments obtained from an H5N1 Vietnam virus scFv antibody with Turkish and Indonesian variants of the HA protein.
Figure 19:
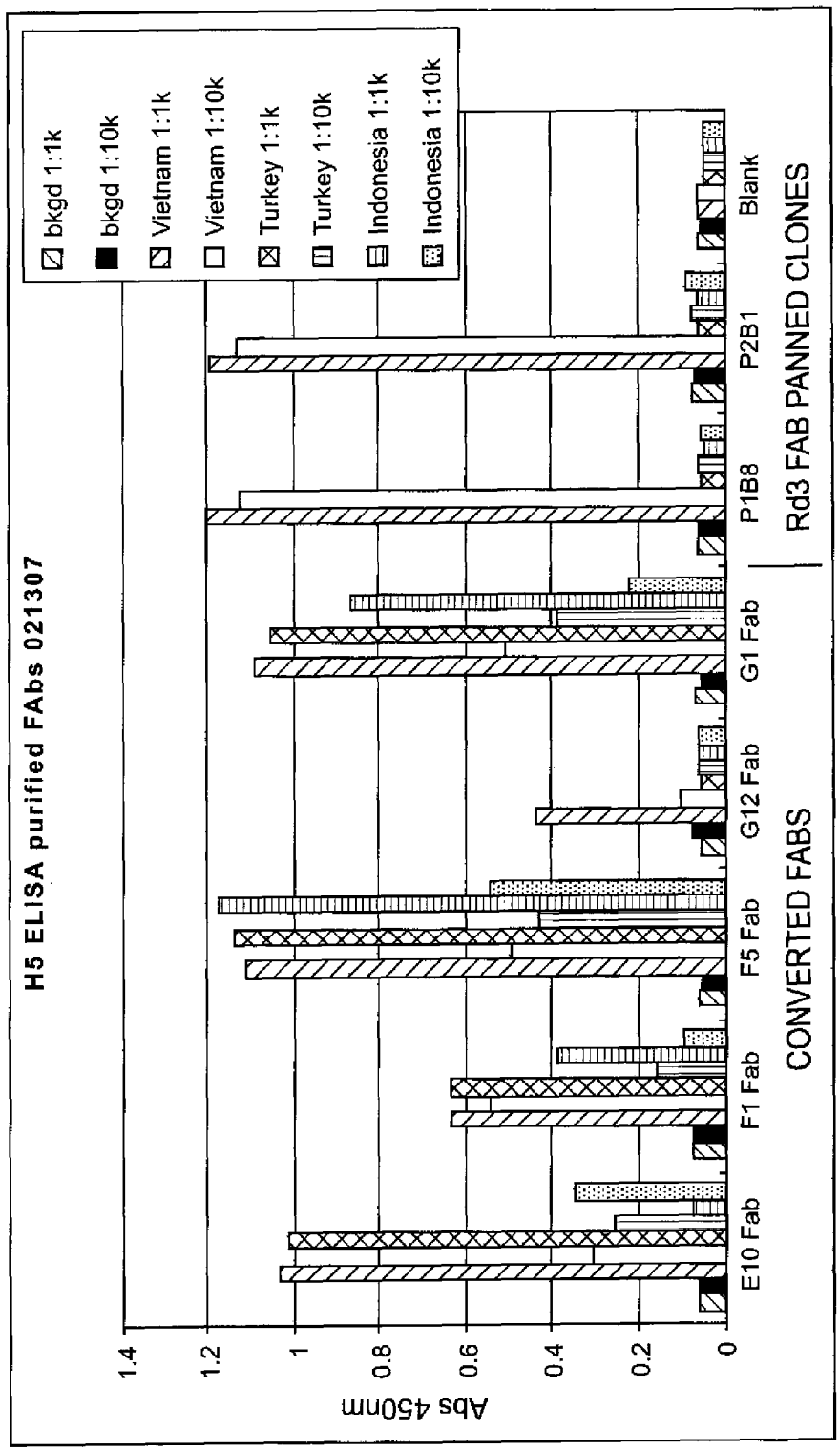

FIGS. 18 and 19 show ELISA results confirming cross-reactivity of certain Fab fragments obtained from an H5N1 Vietnam virus scFv antibody with Turkish and Indonesian variants of the HA protein.

EXAMPLE 2

Constructing Donor-Specific Antibody Library for Patients Infected with HIV

Bone Marrow Protocol and Sera Preparation

Blood is obtained by standard venopuncture, allowed to clot, and processed to recover serum. The serum is stored at −20° C. for 3-4 days until they are shipped on dry ice. Donors are anaesthetized with an injection of a local anesthetic and 5 ml of bone marrow is removed from the pelvic bone of each patient donor. Next the 5 ml of bone marrow is placed into a sterile 50-ml tube containing 45 ml RNAlater (Ambion). The mixture is gently inverted approximately 8-20 times, until there are no visible clumps and the marrow and RNAlater are mixed well. Next the specimen is refrigerated the between 2-10° C. overnight. Following the overnight refrigeration, the specimens are stored at −20° C. for 3-4 days until they are shipped on dry ice. Upon receipt the RNAlater/marrow and sera containing tubes are stored at −80° C. until processed. Candidate patient should be tested HIV positive prior to be selected as donors.

Bone marrow extraction and mRNA purification, reverse transcription, PCR, antibody light and heavy chain construction, phagemid panning and amplification, ELISA and sequencing are performed essentially as described in Example 1.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All references cited throughout the specification are hereby expressly incorporated by reference.

What is claimed:

1. A method of making a donor-specific library expressing a collection of antibodies or antibody fragments to a target antigen, comprising the steps of:
   a) obtaining mRNA from lymphocytes of a human patient donor who has suffered from, or who is suffering from a disease evoking antibody production to said antigen;
   b) generating in a vector a collection of nucleic acids comprising sequences encoding an immunoglobulin repertoire of said patient by reverse transcription of said obtained mRNA; and
   c) identifying said donor-specific library with a unique nucleotide sequence barcode that is linked to and labels said nucleic acids in the vector.

2. The method of claim 1, further comprising steps of generating a serological profile of said patient and/or examining medical history of said patient prior or subsequent to step a).

3. The method of claim 2, further comprises steps of: d) expressing said immunoglobulin repertoire; and e) displaying said immunoglobulin repertoire in a display system.

4. The method of claim 3, wherein the display system is a phagemid.

5. The method of claim 4 further comprising the step of selecting members of the library based on their ability to neutralize the antigen.

6. The method of claim 5 that yields at least one neutralizing antibody.

7. The method of claim 5 that yields more than one neutralizing antibody.

8. The method of claim 7 further comprising the step of creating one or more sub-libraries comprising library members that were found to neutralize the antigen.

9. The method of claim 5 comprising the step of sequencing at least one library member identified.

10. The method of claim 1 wherein the nucleotide sequence barcode is linked to and labels said nucleic acids such that it does not interfere with the expression of said nucleic acid molecules.

11. The method of claim 1 wherein said nucleotide sequence barcode is a contiguous non-coding sequence of one to about 24 nucleotides.

12. The method of claim 11 wherein said nucleotide sequence barcode is linked to the 3' or 5' non-coding region of said nucleic acid molecules.

13. The method of claim 1 wherein said nucleotide sequence barcode is a coding sequence or one or more silent mutations incorporated into the nucleic acid molecules encoding the antibody light or heavy chains or fragments thereof.

14. The method of claim 1 wherein said nucleotide sequence barcode is non-contiguous.

15. The method of claim 14 wherein at least part of said non-contiguous sequence is linked to or incorporated in the vectors present in the library.

16. The method of claim 14 wherein at least part of said non-contiguous sequence is incorporated into the nucleic acid molecules encoding the antibody light or heavy chains or fragments thereof such that it does not interfere with the expression of said nucleic acid molecules.

17. The method of claim 1 wherein the barcode encodes a peptide or polypeptide sequence.

18. The method of claim 1, wherein the mRNA is obtained from bone marrow of the donor.

* * * * *

SEQUENCE LISTING

<160> NUMBER OF SEQ ID NOS: 106

<210> SEQ ID NO 1
<211> LENGTH: 18
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 1
tttttttttt tttttttt                                                 18

<210> SEQ ID NO 2
<211> LENGTH: 13
<212> TYPE: DNA
<213> ORGANISM: Artificial sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 2
ggccnnnnng gcc                                                      13

<210> SEQ ID NO 3
<211> LENGTH: 30
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 3
tttttttttt tttttttttt tttttttttt                                    30

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base

```
<222> LOCATION: (36)..(36)
<223> OTHER INFORMATION: a, c, t, g, unknown or other

<400> SEQUENCE: 4 acn aar gcn tcn tay ctn agy acn agy agy agy ctn gay         39
Thr Lys Ala Ser Tyr Leu Ser Thr Ser Ser Ser Leu Asp
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Lys Ala Ser Tyr Leu Ser Thr Ser Ser Ser Leu Asp
1               5                   10

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other

<400> SEQUENCE: 6 gcn cgn ggn ath tay tty tay ggn acn acn tay tty gay         39
Ala Arg Gly Ile Tyr Phe Tyr Gly Thr Thr Tyr Phe Asp
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Arg Gly Ile Tyr Phe Tyr Gly Thr Thr Tyr Phe Asp
1               5                   10
```

```
<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other

<400> SEQUENCE: 8 rcn mrn gsn wyn tay ytn wry rsn asn asn wry ytn gay        39
Xaa Xaa Xaa Xaa Tyr Leu Xaa Xaa Xaa Xaa Xaa Leu Asp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Thr
<220> FEATURE:
<221> NAME/KEY: MOD_RES
<222> LOCATION: (2)..(2)
<223> OTHER INFORMATION: Arg, Ser, Lys, Asn, Gln or His
<220> FEATURE:
<221> NAME/KEY: MOD_RES
<222> LOCATION: (3)..(3)
<223> OTHER INFORMATION: Gly or Ala
<220> FEATURE:
<221> NAME/KEY: MOD_RES
<222> LOCATION: (4)..(4)
<223> OTHER INFORMATION: Thr, Ile, Met, Ser, Leu or Phe
<220> FEATURE:
<221> NAME/KEY: MOD_RES
<222> LOCATION: (6)..(6)
```

```
-continued

<223> OTHER INFORMATION: Leu or Phe
<220> FEATURE:
<221> NAME/KEY: MOD_RES
<222> LOCATION: (7)..(7)
<223> OTHER INFORMATION: Ser, Asn, Cys or Tyr
<220> FEATURE:
<221> NAME/KEY: MOD_RES
<222> LOCATION: (8)..(8)
<223> OTHER INFORMATION: Gly, Ala, Arg, Ser or Thr
<220> FEATURE:
<221> NAME/KEY: MOD_RES
<222> LOCATION: (9)..(10)
<223> OTHER INFORMATION: Arg, Ser or Thr
<220> FEATURE:
<221> NAME/KEY: MOD_RES
<222> LOCATION: (11)..(11)
<223> OTHER INFORMATION: Ser, Asn, Cys or Tyr
<220> FEATURE:
<221> NAME/KEY: MOD_RES
<222> LOCATION: (12)..(12)
<223> OTHER INFORMATION: Leu or Phe

<400> SEQUENCE: 9

Xaa Xaa Xaa Xaa Tyr Xaa Xaa Xaa Xaa Xaa Xaa Asp
 1               5                   10

<210> SEQ ID NO 10
<211> LENGTH: 595
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Lys Ile Ile Ile Ile Leu Leu Leu Leu Ala Leu Ala Ala Cys
 1               5                   10                  15

Ser Gly Ala Leu Pro Gly Asn Asp Asn Ser Thr Asp Lys Ile Cys Ile
            20                  25                  30

Gly Tyr His Ala Asn Asn Ser Thr Glu Thr Val Asp Thr Leu Thr Glu
        35                  40                  45

Lys Asn Val Glu Val Thr His Ala Thr Glu Leu Val Glu Thr Thr His
    50                  55                  60

Asn Gly Lys Leu Cys Ser Leu Asn Gly Lys Ser Pro Leu Asp Leu Gly
65                  70                  75                  80

Asp Cys Ser Ile Glu Gly Trp Ile Leu Gly Asn Pro Gln Cys Asp Leu
                85                  90                  95

Leu Leu Gly Gly Arg Glu Trp Ser Tyr Ile Val Glu Arg Pro Asn Ala
            100                 105                 110

Pro Asn Gly Leu Cys Tyr Pro Gly Asp Phe Glu Asn Tyr Glu Glu Leu
        115                 120                 125

Arg His Leu Phe Ser Ser Ser Gly Ser Phe Glu Lys Ile Glu Ile Phe
    130                 135                 140

Pro Lys Thr Phe Thr Trp Gly Asn Val Val Thr Thr Asn Gly Thr Thr
145                 150                 155                 160

Lys Ala Cys Lys Asp Arg Ser Gly Gly Ser Ser Phe Tyr Arg Asn Leu
                165                 170                 175

Val Trp Leu Thr Ser Lys Lys Gly Ser Ala Tyr Pro Val Ile Lys
            180                 185                 190

Gly Thr Tyr Asn Asn Thr Arg Gly Glu Asp Ile Leu Ile Ile Trp Gly
        195                 200                 205

Ile His His Pro Pro Thr Thr Thr Glu Gln Thr Lys Leu Tyr Gly Asn
    210                 215                 220
```

Ala Asp Thr Tyr Val Ser Val Gly Thr Ser Thr Tyr Asn Arg Arg Phe
225                 230                 235                 240

Val Pro Glu Ile Gly Ala Arg Pro Lys Val Asn Gly Gln Ser Gly Arg
            245                 250                 255

Met Asp Phe Tyr Trp Thr Leu Leu Lys Pro Gly Asp Thr Ile Thr Phe
        260                 265                 270

Glu Ser Asn Gly Asn Leu Ile Ala Pro Arg Tyr Ala Tyr Lys Leu Ile
    275                 280                 285

Lys Gly Gly Pro Ser Gly Ile Glu Tyr Asn Gly Lys Gly Arg Ile Ile
290                 295                 300

Gln Ser Glu Asp Leu Pro Ile Gly Ala Asn Cys Asn Thr Lys Cys Gln
305                 310                 315                 320

Thr Pro Gly Gly Ala Ile Asn Thr Ser Lys Pro Phe Gln Asn Ile Ser
            325                 330                 335

Pro Leu Thr Ile Gly Glu Cys Pro Lys Tyr Val Lys Ser Gly Ser Leu
        340                 345                 350

Lys Leu Ala Thr Gly Leu Arg Asn Val Pro Glu Ile Glu Arg Arg
    355                 360                 365

Arg Lys Ser Arg Gly Leu Phe Gly Ala Ile Ala Gly Phe Ile Glu Gly
370                 375                 380

Gly Trp Pro Gly Leu Ile Asp Gly Trp Tyr Gly Phe His His Gln Asn
385                 390                 395                 400

Ala Gln Gly Thr Gly Ile Ala Ala Asp Lys Lys Ser Thr Gln Lys Ala
            405                 410                 415

Ile Asp Gln Ile Thr Asn Lys Val Asn Asn Ile Ile Glu Lys Met Asn
        420                 425                 430

Thr Gln Phe Glu Ala Ile Asp His Glu Phe Ser Glu Val Glu Lys Arg
    435                 440                 445

Ile Asn Asn Leu Asn Lys Lys Val Asp Asp Gly Phe Thr Asp Ile Trp
450                 455                 460

Ser Tyr Asn Ala Glu Leu Leu Val Leu Leu Glu Asn Gln His Thr Leu
465                 470                 475                 480

Asp Leu His Asp Ser Asn Val Lys Asn Leu Tyr Glu Lys Val Arg Arg
            485                 490                 495

Gln Leu Arg Asp Asn Ala Glu Asp Asp Gly Asn Gly Cys Phe Glu Ile
        500                 505                 510

Tyr His Lys Cys Asp Asp Glu Cys Met Glu Ser Ile Arg Asn Gly Thr
    515                 520                 525

Tyr Asp His Pro Glu Tyr Arg Glu Glu Ser Lys Leu Asn Arg Gln Glu
530                 535                 540

Ile Asp Gly Val Lys Leu Glu Ser Gly Gly Asn Val Tyr Lys Ile Leu
545                 550                 555                 560

Ser Ile Tyr Ser Thr Val Ala Ser Ser Leu Val Leu Ala Ala Leu Ile
            565                 570                 575

Ala Gly Phe Ile Phe Trp Ala Cys Ser Asn Gly Asn Cys Arg Cys Thr
        580                 585                 590

Ile Cys Ile
        595

<210> SEQ ID NO 11
<211> LENGTH: 561
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Lys Thr His Asn Gly Lys Leu Cys Lys Leu Asn Gly Ile Pro Pro Leu
 50                  55                  60

Glu Leu Gly Asp Cys Ser Ile Ala Gly Trp Leu Leu Gly Asn Pro Glu
65                  70                  75                  80

Cys Asp Arg Leu Leu Ser Val Pro Glu Trp Ser Tyr Ile Met Glu Lys
                85                  90                  95

Glu Asn Pro Arg Asp Gly Leu Cys Tyr Pro Gly Ser Phe Asn Asp Tyr
            100                 105                 110

Glu Glu Leu Lys His Leu Leu Ser Ser Val Lys His Phe Glu Lys Val
        115                 120                 125

Lys Ile Leu Pro Lys Asp Arg Trp Thr Gln His Thr Thr Thr Gly Gly
130                 135                 140

Ser Arg Ala Cys Ala Val Ser Gly Asn Pro Ser Phe Phe Arg Asn Met
145                 150                 155                 160

Val Trp Leu Thr Glu Lys Gly Ser Asn Tyr Pro Val Ala Lys Gly Ser
                165                 170                 175

Tyr Asn Asn Thr Ser Gly Glu Gln Met Leu Ile Ile Trp Gly Val His
            180                 185                 190

His Pro Asn Asp Glu Lys Glu Gln Arg Thr Leu Tyr Gln Asn Val Gly
        195                 200                 205

Thr Tyr Val Ser Val Gly Thr Ser Thr Leu Asn Lys Arg Ser Thr Pro
210                 215                 220

Asp Ile Ala Thr Arg Pro Lys Val Asn Gly Leu Gly Ser Arg Met Glu
225                 230                 235                 240

Phe Ser Trp Thr Leu Leu Asp Met Trp Asp Thr Ile Asn Phe Glu Ser
                245                 250                 255

Thr Gly Asn Leu Ile Ala Pro Glu Tyr Gly Phe Lys Ile Ser Lys Arg
            260                 265                 270

Gly Ser Ser Gly Ile Met Lys Thr Glu Gly Thr Leu Glu Asn Cys Glu
        275                 280                 285

Thr Lys Cys Gln Thr Pro Leu Gly Ala Ile Asn Thr Thr Leu Pro Phe
290                 295                 300

His Asn Val His Pro Leu Thr Ile Gly Glu Cys Pro Lys Tyr Val Lys
305                 310                 315                 320

Ser Glu Lys Leu Val Leu Ala Thr Gly Leu Arg Asn Val Pro Gln Ile
                325                 330                 335

Glu Ser Arg Gly Leu Phe Gly Ala Ile Ala Gly Phe Ile Glu Gly Gly
            340                 345                 350

Trp Gln Gly Met Ile Asp Gly Trp Tyr Gly Tyr His His Ser Asn Asp
        355                 360                 365

Gln Gly Ser Gly Tyr Ala Ala Asp Lys Glu Ser Thr Gln Lys Ala Phe
370                 375                 380

Asp Gly Ile Thr Asn Lys Val Asn Ser Val Ile Glu Lys Met Asn Thr
385                 390                 395                 400

Gln Phe Glu Ala Val Gly Lys Glu Phe Ser Asn Leu Glu Arg Arg Leu
                405                 410                 415
```

-continued

```
Glu Asn Leu Asn Lys Lys Met Glu Asp Gly Phe Leu Asp Val Trp Thr
            420                 425                 430
Tyr Asn Ala Glu Leu Leu Val Leu Met Glu Asn Glu Arg Thr Leu Asp
        435                 440                 445
Phe His Asp Ser Asn Val Lys Asn Leu Tyr Asp Lys Val Arg Met Gln
    450                 455                 460
Leu Arg Asp Asn Val Lys Glu Leu Gly Asn Gly Cys Phe Glu Phe Tyr
465                 470                 475                 480
His Lys Cys Asp Asp Glu Cys Met Asn Ser Val Lys Asn Gly Thr Tyr
            485                 490                 495
Asp Tyr Pro Lys Tyr Glu Glu Glu Ser Lys Leu Asn Arg Asn Glu Ile
        500                 505                 510
Lys Gly Val Lys Leu Ser Ser Met Gly Val Tyr Gln Ile Leu Ala Ile
    515                 520                 525
Tyr Ala Thr Val Ala Gly Ser Leu Ser Leu Ala Ile Met Met Ala Gly
530                 535                 540
Ile Ser Phe Trp Met Cys Ser Asn Gly Ser Leu Gln Cys Arg Ile Cys
545                 550                 555                 560
Ile
```

<210> SEQ ID NO 12
<211> LENGTH: 561
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Tyr Lys Val Val Val Ile Ile Ala Leu Leu Gly Ala Val Lys Gly
1               5                   10                  15
Leu Asp Arg Ile Cys Leu Gly His His Ala Val Ala Asn Gly Thr Ile
            20                  25                  30
Val Lys Thr Leu Thr Asn Glu Gln Glu Glu Val Thr Asn Ala Thr Glu
        35                  40                  45
Thr Val Glu Ser Thr Asn Leu Asn Lys Leu Cys Met Lys Gly Arg Ser
    50                  55                  60
Tyr Lys Asp Leu Gly Asn Cys His Pro Val Gly Met Leu Ile Gly Thr
65                  70                  75                  80
Pro Val Cys Asp Pro His Leu Thr Gly Thr Trp Asp Thr Leu Ile Glu
            85                  90                  95
Arg Glu Asn Ala Ile Ala His Cys Tyr Pro Gly Ala Thr Ile Asn Glu
        100                 105                 110
Glu Ala Leu Arg Gln Lys Ile Met Glu Ser Gly Gly Ile Ser Lys Met
    115                 120                 125
Ser Thr Gly Phe Thr Tyr Gly Ser Ser Ile Thr Ser Ala Gly Thr Thr
130                 135                 140
Lys Ala Cys Met Arg Asn Gly Gly Asp Ser Phe Tyr Ala Glu Leu Lys
145                 150                 155                 160
Trp Leu Val Ser Lys Thr Lys Gly Gln Asn Phe Pro Gln Thr Thr Asn
            165                 170                 175
Thr Tyr Arg Asn Thr Asp Thr Ala Glu His Leu Ile Ile Trp Gly Ile
        180                 185                 190
His His Pro Ser Ser Thr Gln Glu Lys Asn Asp Leu Tyr Gly Thr Gln
    195                 200                 205
```

```
Ser Leu Ser Ile Ser Val Glu Ser Thr Tyr Gln Asn Asn Phe Val
    210                 215                 220

Pro Val Val Gly Ala Arg Pro Gln Val Asn Gln Ser Gly Arg Ile
225                 230                 235                 240

Asp Phe His Trp Thr Leu Val Gln Pro Gly Asp Asn Ile Thr Phe Ser
                245                 250                 255

Asp Asn Gly Gly Leu Ile Ala Pro Ser Arg Val Ser Lys Leu Thr Gly
                260                 265                 270

Arg Asp Leu Gly Ile Gln Ser Glu Ala Leu Ile Asp Asn Ser Cys Glu
            275                 280                 285

Ser Lys Cys Phe Trp Arg Gly Gly Ser Ile Asn Thr Lys Leu Pro Phe
290                 295                 300

Gln Asn Leu Ser Pro Arg Thr Val Gly Gln Cys Pro Lys Tyr Val Asn
305                 310                 315                 320

Gln Arg Ser Leu Leu Leu Ala Thr Gly Met Arg Asn Val Pro Glu Val
                325                 330                 335

Val Gln Gly Arg Gly Leu Phe Gly Ala Ile Ala Gly Phe Ile Glu Asn
                340                 345                 350

Gly Trp Glu Gly Met Val Asp Gly Trp Tyr Gly Phe Arg His Gln Asn
            355                 360                 365

Ala Gln Gly Thr Gly Gln Ala Ala Asp Tyr Lys Ser Thr Gln Ala Ala
370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Thr Glu His Gln
                405                 410                 415

Ile Gly Asn Val Ile Asn Trp Thr Lys Asp Ser Ile Thr Asp Ile Trp
                420                 425                 430

Thr Tyr Asn Ala Glu Leu Leu Val Ala Met Glu Asn Gln His Thr Ile
            435                 440                 445

Asp Met Ala Asp Ser Glu Met Leu Asn Leu Tyr Glu Arg Val Arg Lys
450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
                485                 490                 495

Tyr Asp His Ser Gln Tyr Arg Glu Glu Ala Leu Leu Asn Arg Leu Asn
                500                 505                 510

Ile Asn Pro Val Lys Leu Ser Ser Gly Tyr Lys Asp Ile Ile Leu Trp
            515                 520                 525

Phe Ser Phe Gly Glu Ser Cys Phe Val Leu Leu Ala Val Val Met Gly
530                 535                 540

Leu Val Phe Phe Cys Leu Lys Asn Gly Asn Met Arg Cys Thr Ile Cys
545                 550                 555                 560

Ile

<210> SEQ ID NO 13
<211> LENGTH: 570
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asn Thr Gln Ile Ile Val Ile Leu Val Leu Gly Leu Ser Met Val
```

```
             1               5                  10                 15
Lys Ser Asp Lys Ile Cys Leu Gly His His Ala Val Ala Asn Gly Thr
                20                 25                 30

Lys Val Asn Thr Leu Thr Glu Arg Gly Val Glu Val Asn Ala Thr
                35                 40                 45

Glu Thr Val Glu Ile Thr Gly Ile Asp Lys Val Cys Thr Lys Gly Lys
 50                 55                 60

Lys Ala Val Asp Leu Gly Ser Cys Gly Ile Leu Gly Thr Ile Ile Gly
65                  70                 75                      80

Pro Pro Gln Cys Asp Leu His Leu Glu Phe Lys Ala Asp Leu Ile Ile
                85                 90                 95

Glu Arg Arg Asn Ser Ser Asp Ile Cys Tyr Pro Gly Arg Phe Thr Asn
                100                105                110

Glu Glu Ala Leu Arg Gln Ile Ile Arg Glu Ser Gly Ile Asp Lys
                115                120                125

Glu Ser Met Gly Phe Arg Tyr Ser Gly Ile Arg Thr Asp Gly Ala Thr
                130                135                140

Ser Ala Cys Lys Arg Thr Val Ser Ser Phe Tyr Ser Glu Met Lys Trp
145                 150                155                     160

Leu Ser Ser Met Asn Asn Gln Val Phe Pro Gln Leu Asn Gln Thr
                165                170                175

Tyr Arg Asn Thr Arg Lys Glu Pro Ala Leu Ile Val Trp Gly Val His
                180                185                190

His Ser Ser Ser Leu Asp Glu Gln Asn Lys Leu Tyr Gly Thr Gly Asn
                195                200                205

Lys Leu Ile Thr Val Gly Ser Ser Lys Tyr Gln Gln Ser Phe Ser Pro
210                 215                220

Ser Pro Gly Ala Arg Pro Lys Val Asn Gly Gln Ala Gly Arg Ile Asp
225                 230                235                     240

Phe His Trp Met Leu Leu Asp Pro Gly Asp Thr Val Thr Phe Thr Phe
                245                250                255

Asn Gly Ala Phe Ile Ala Pro Asp Arg Ala Thr Phe Leu Arg Ser Asn
                260                265                270

Ala Pro Ser Gly Ile Glu Tyr Asn Gly Lys Ser Leu Gly Ile Gln Ser
                275                280                285

Asp Ala Gln Ile Asp Glu Ser Cys Glu Gly Glu Cys Phe Tyr Ser Gly
                290                295                300

Gly Thr Ile Asn Ser Pro Leu Pro Phe Gln Asn Ile Asp Ser Arg Ala
305                 310                315                     320

Val Gly Lys Cys Pro Arg Tyr Val Lys Gln Ser Ser Leu Pro Leu Ala
                325                330                335

Leu Gly Met Lys Asn Val Pro Glu Lys Ile Arg Thr Arg Gly Leu Phe
                340                345                350

Gly Ala Ile Ala Gly Phe Ile Glu Asn Gly Trp Glu Gly Leu Ile Asp
                355                360                365

Gly Trp Tyr Gly Phe Arg His Gln Asn Ala Gln Gly Gln Gly Thr Ala
                370                375                380

Ala Asp Tyr Lys Ser Thr Gln Ala Ala Ile Asp Gln Ile Thr Gly Lys
385                 390                395                     400

Leu Asn Arg Leu Ile Glu Lys Thr Asn Lys Gln Phe Glu Leu Ile Asp
                405                410                415

Asn Glu Phe Thr Glu Val Glu Gln Gln Ile Gly Asn Val Ile Asn Trp
                420                425                430
```

```
Thr Arg Asp Ser Leu Thr Glu Ile Trp Ser Tyr Asn Ala Glu Leu Leu
        435                 440                 445

Val Ala Met Glu Asn Gln His Thr Ile Asp Leu Ala Asp Ser Glu Met
450                 455                 460

Asn Lys Leu Tyr Glu Arg Val Arg Arg Gln Leu Arg Glu Asn Ala Glu
465                 470                 475                 480

Glu Asp Gly Thr Gly Cys Phe Glu Ile Phe His Arg Cys Asp Asp Gln
                485                 490                 495

Cys Met Glu Ser Ile Arg Asn Asn Thr Tyr Asn His Thr Glu Tyr Arg
            500                 505                 510

Gln Glu Ala Leu Gln Asn Arg Ile Met Ile Asn Pro Val Lys Leu Ser
        515                 520                 525

Ser Gly Tyr Lys Asp Val Ile Leu Trp Phe Ser Phe Gly Ala Ser Cys
    530                 535                 540

Val Met Leu Leu Ala Ile Ala Met Gly Leu Ile Phe Met Cys Val Lys
545                 550                 555                 560

Asn Gly Asn Leu Arg Cys Thr Ile Cys Ile
                565                 570

<210> SEQ ID NO 14
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Asn Thr Gln Ile Leu Ile Leu Ala Leu Val Ala Ile Ile Pro Thr
1               5                   10                  15

Asn Ala Asp Lys Ile Cys Leu Gly His His Ala Val Ser Asn Gly Ala
                20                  25                  30

Lys Val Asn Thr Leu Thr Glu Arg Gly Val Glu Val Val Asn Ala Thr
            35                  40                  45

Glu Thr Val Glu Arg Thr Asn Val Pro Arg Ile Cys Ser Lys Gly Lys
50                  55                  60

Arg Thr Val Asp Leu Gly Gln Cys Gly Leu Leu Gly Thr Ile Thr Gly
65                  70                  75                  80

Phe Pro Gln Cys Asp Gln Phe Leu Glu Phe Ser Ala Asp Leu Ile Ile
                85                  90                  95

Glu Arg Arg Glu Gly Asn Asp Val Cys Tyr Pro Gly Lys Phe Val Asn
            100                 105                 110

Glu Glu Ala Leu Arg Gln Ile Leu Arg Lys Ser Gly Gly Ile Asp Lys
        115                 120                 125

Glu Thr Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Ile Arg Lys Asp Pro Ala Leu Ile Ile Trp Gly Ile His
            180                 185                 190

His Ser Gly Ser Thr Ala Glu Gln Thr Lys Leu Tyr Gly Ser Gly Asn
        195                 200                 205

Lys Leu Ile Thr Val Gly Ser Ser Asn Tyr Gln Gln Ser Phe Val Pro
    210                 215                 220
```

Ser Pro Gly Ala Arg Pro Gln Val Asn Gly Gln Ser Gly Arg Ile Asp
225                 230                 235                 240

Phe His Trp Leu Met Leu Asn Pro Asn Asp Thr Val Thr Phe Ser Phe
            245                 250                 255

Asn Gly Ala Phe Ile Ala Pro Asp Arg Ala Ser Phe Leu Arg Gly Lys
        260                 265                 270

Ser Met Gly Ile Gln Ser Glu Val Gln Val Asp Ala Asn Cys Glu Gly
    275                 280                 285

Asp Cys Tyr His Asp Gly Gly Thr Ile Leu Ser Ser Leu Pro Phe Gln
290                 295                 300

Asn Ile Asn Ser Arg Thr Val Gly Glu Cys Pro Arg Tyr Val Lys Gln
305                 310                 315                 320

Glu Ser Leu Leu Leu Ala Thr Gly Met Lys Asn Val Pro Glu Ile Pro
            325                 330                 335

Lys Gly Arg Gly Leu Phe Gly Ala Ile Ala Gly Phe Ile Glu Asn Gly
        340                 345                 350

Trp Glu Gly Leu Val Asp Gly Trp Tyr Gly Phe Arg His Gln Asn Ala
    355                 360                 365

Gln Gly Glu Gly Thr Ala Ala Asp Tyr Lys Ser Thr Gln Ser Ala Ile
370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
            405                 410                 415

Gly Asn Val Ile Asn Trp Thr Arg Asp Ser Leu Thr Glu Met Trp Ser
        420                 425                 430

Tyr Asn Ala Glu Leu Leu Val Ala Met Glu Asn Gln His Thr Ile Asp
    435                 440                 445

Leu Ala Asp Ser Glu Met Asn Lys Leu Tyr Glu Arg Val Arg Arg Gln
450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
            485                 490                 495

Asp His Ser Lys Tyr Arg Glu Glu Ala Ile Gln Asn Arg Ile Gln Ile
        500                 505                 510

Asp Pro Val Lys Leu Ser Ser Gly Tyr Lys Asp Val Ile Leu Trp Phe
    515                 520                 525

Ser Phe Gly Ala Ser Cys Phe Ile Leu Leu Ala Ile Ala Met Gly Leu
530                 535                 540

Val Phe Ile Cys Val Lys Asn Gly Asn Met Arg Cys Thr Ile Cys Ile
545                 550                 555                 560

<210> SEQ ID NO 15
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

-continued

```
Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
 50                  55                  60

Ala Pro Leu Gln Leu Gly Lys Cys Asn Ile Ala Gly Trp Leu Leu Gly
 65                  70                  75                  80

Asn Pro Glu Cys Asp Leu Leu Leu Thr Ala Ser Ser Trp Ser Tyr Ile
                 85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
450                 455                 460
```

-continued

```
Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
            485                 490                 495

Arg Asn Gly Thr Tyr Asp Tyr Pro Lys Tyr Ser Glu Ser Lys Leu
        500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 16
<211> LENGTH: 552
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Ser Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asn His Asp Ala Ser
        115                 120                 125

Ser Gly Val Ser Ser Ala Cys Pro Tyr Leu Gly Arg Ser Ser Phe Phe
    130                 135                 140

Arg Asn Val Val Trp Leu Ile Lys Lys Asn Ser Ser Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Glu Ile Ala Thr Arg Pro Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255
```

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
        290                 295                 300

Tyr Val Lys Ser Asn Arg Leu Val Leu Ala Thr Gly Leu Arg Asn Thr
305                 310                 315                 320

Pro Gln Arg Glu Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Gln
            355                 360                 365

Glu Ser Thr Gln Lys Ala Ile Asp Gly Val Thr Asn Lys Val Asn Ser
        370                 375                 380

Ile Ile Asn Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Val Lys Asn Gly Thr Tyr Asp Tyr Pro Gln Tyr Ser Glu Glu Ala
                485                 490                 495

Arg Leu Asn Arg Glu Glu Ile Ser Gly Val Lys Leu Glu Ser Met Gly
            500                 505                 510

Thr Tyr Gln Ile Leu Ser Ile Tyr Ser Thr Val Ala Ser Ser Leu Ala
        515                 520                 525

Leu Ala Ile Met Val Ala Gly Leu Ser Leu Trp Met Cys Ser Asn Gly
    530                 535                 540

Ser Leu Gln Cys Arg Ile Cys Ile
545                 550

<210> SEQ ID NO 17
<211> LENGTH: 564
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Leu Ser Ile Val Ile Leu Phe Leu Leu Ile Ala Glu Asn Ser Ser
1               5                   10                  15

Gln Asn Thr Tyr Gly Asn Pro Val Ile Cys Met Gly His His Ala Val
            20                  25                  30

Ala Asn Gly Thr Met Val Lys Thr Leu Ala Asp Asp Gln Val Glu Val
        35                  40                  45

Val Thr Ala Gln Glu Leu Val Glu Ser Gln Asn Leu Pro Glu Leu Cys
    50                  55                  60

```
Pro Ser Pro Leu Arg Leu Val Asp Gly Gln Thr Cys Asp Ile Ile Asn
 65                  70                  75                  80

Gly Ala Leu Gly Ser Pro Gly Cys Asp His Leu Asn Gly Ala Glu Trp
                 85                  90                  95

Asp Val Phe Ile Glu Arg Pro Asn Ala Val Asp Thr Cys Tyr Pro Phe
            100                 105                 110

Asp Val Pro Glu Tyr Gln Ser Leu Arg Ser Ile Leu Ala Asn Asn Gly
        115                 120                 125

Lys Phe Glu Phe Ile Ala Glu Glu Phe Gln Trp Asn Thr Val Lys Gln
130                 135                 140

Asn Gly Lys Ser Gly Ala Cys Lys Arg Ala Asn Val Asp Asp Phe Phe
145                 150                 155                 160

Asn Arg Leu Asn Trp Leu Val Lys Ser Asp Gly Asn Ala Tyr Pro Phe
                165                 170                 175

Gln Asn Leu Thr Lys Ile Asn Asn Gly Asp Tyr Ala Arg Leu Tyr Ile
            180                 185                 190

Trp Gly Val His His Pro Ser Thr Ser Thr Glu Gln Ile Asn Leu Tyr
        195                 200                 205

Lys Asn Asn Pro Gly Arg Val Thr Val Ser Thr Lys Thr Ser Gln Thr
210                 215                 220

Ser Val Val Pro Asp Ile Gly Ser Arg Pro Leu Val Arg Gly Gln Ser
225                 230                 235                 240

Gly Arg Val Ser Phe Tyr Trp Thr Ile Val Glu Pro Gly Asp Leu Ile
                245                 250                 255

Val Phe Asn Thr Ile Gly Asn Leu Ile Ala Pro Arg Gly His Tyr Lys
            260                 265                 270

Leu Asn Asn Gln Lys Lys Ser Thr Ile Leu Asn Thr Ala Ile Pro Ile
        275                 280                 285

Gly Ser Cys Val Ser Lys Cys His Thr Asp Lys Gly Ser Leu Ser Thr
290                 295                 300

Thr Lys Pro Phe Gln Asn Ile Ser Arg Ile Ala Val Gly Asp Cys Pro
305                 310                 315                 320

Arg Tyr Val Lys Gln Gly Ser Leu Lys Leu Ala Thr Gly Met Arg Asn
                325                 330                 335

Ile Pro Glu Lys Ala Ser Arg Gly Leu Phe Gly Ala Ile Ala Gly Phe
            340                 345                 350

Ile Glu Asn Gly Trp Gln Gly Leu Ile Asp Gly Trp Tyr Gly Phe Arg
        355                 360                 365

His Gln Asn Ala Glu Gly Thr Gly Thr Ala Ala Asp Leu Lys Ser Thr
370                 375                 380

Gln Ala Ala Ile Asn Gln Ile Asn Gly Lys Leu Asn Arg Leu Ile Glu
385                 390                 395                 400

Lys Thr Asn Asp Lys Tyr His Gln Ile Glu Lys Glu Phe Glu Gln Val
                405                 410                 415

Glu Gly Arg Ile Gln Asp Leu Glu Asn Tyr Val Glu Asp Thr Lys Ile
            420                 425                 430

Asp Leu Trp Ser Tyr Asn Ala Glu Leu Leu Val Ala Leu Glu Asn Gln
        435                 440                 445

His Thr Ile Asp Val Thr Asp Ser Glu Met Asn Lys Leu Phe Glu Arg
450                 455                 460

Val Arg Arg Gln Leu Arg Glu Asn Ala Glu Asp Lys Gly Asn Gly Cys
465                 470                 475                 480

Phe Glu Ile Phe His Lys Cys Asp Asn Asn Cys Ile Glu Ser Ile Arg
```

```
                    485                 490                 495
Asn Gly Thr Tyr Asp His Asp Ile Tyr Arg Asp Glu Ala Ile Asp Asn
                500                 505                 510

Arg Phe Gln Ile Gln Gly Val Lys Leu Thr Gln Gly Tyr Lys Asp Ile
            515                 520                 525

Ile Leu Trp Ile Ser Phe Ser Ile Ser Cys Phe Leu Leu Val Ala Leu
        530                 535                 540

Leu Leu Ala Phe Ile Leu Trp Ala Cys Gln Asn Gly Asn Ile Arg Cys
545                 550                 555                 560

Gln Ile Cys Ile

<210> SEQ ID NO 18
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285
```

```
Pro Ile Asp Thr Cys Ile Ser Glu Cys Ile Thr Pro Asn Gly Ser Ile
        290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 19
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ile Ala Ile Ile Leu Ala Ile Val Ala Ser Thr Ser Lys Ser
1               5                   10                  15

Lys Ile Cys Ile Gly Tyr His Ala Asn Asn Ser Thr Glu Thr Gln Asp
                20                  25                  30

Thr Leu Ile Leu Lys Asn Val Thr Val Thr His Ser Val Glu Leu Leu
            35                  40                  45

Glu Ser Gln Lys Glu Glu Arg Phe Cys Arg Val Leu Asn Lys Ala Pro
        50                  55                  60

Leu Asp Leu Lys Gly Cys Thr Ile Glu Gly Trp Ile Leu Gly Asn Pro
65                  70                  75                  80
```

-continued

```
Gln Cys Asp Ile Leu Leu Gly Asp Gln Arg Trp Ser Tyr Ile Val Glu
            85                  90                  95
Arg Pro Gly Ala Gln Asn Gly Ile Cys Tyr Pro Gly Ile Leu Asn Glu
            100                 105                 110
Leu Glu Glu Leu Lys Ala Leu Ile Gly Ser Gly Glu Arg Val Gln Arg
            115                 120                 125
Phe Glu Met Phe Pro Lys Ser Thr Trp Ala Gly Val Asp Thr Ser Arg
130                 135                 140
Gly Val Thr Lys Ala Cys Pro Tyr Ile Ser Gly Ser Ser Phe Tyr Gly
145                 150                 155                 160
Asn Leu Leu Trp Ile Ile Lys Thr Glu Ser Ala Ala Tyr Pro Val Ile
                165                 170                 175
Lys Gly Thr Tyr Asn Asn Thr Gly Ser Gln Pro Ile Leu Tyr Phe Trp
            180                 185                 190
Gly Val His His Pro Pro Asp Thr Asn Glu Gln Asn Thr Leu Tyr Gly
            195                 200                 205
Ser Gly Asp Arg Tyr Val Arg Met Gly Thr Glu Ser Met Arg Phe Ala
210                 215                 220
Lys Ser Pro Glu Ile Ala Ala Arg Pro Ala Val Asn Gly Gln Arg Gly
225                 230                 235                 240
Arg Ile Asp Tyr Tyr Trp Ser Val Leu Lys Pro Gly Glu Thr Leu Asn
                245                 250                 255
Val Glu Ser Asn Gly Asn Leu Ile Ala Pro Trp Tyr Ala Tyr Lys Phe
            260                 265                 270
Thr Ser Ser Asn Asn Lys Gly Ala Val Phe Lys Ser Asn Leu Pro Ile
            275                 280                 285
Glu Asn Cys Asp Ala Val Cys Gln Thr Val Ala Gly Ala Leu Arg Thr
290                 295                 300
Asn Lys Thr Phe Gln Asn Val Ser Pro Leu Trp Ile Gly Glu Cys Pro
305                 310                 315                 320
Lys Tyr Val Lys Ser Asp Ser Leu Arg Leu Ala Thr Gly Leu Arg Asn
                325                 330                 335
Val Pro Gln Ala Glu Thr Arg Gly Leu Phe Gly Ala Ile Ala Gly Phe
            340                 345                 350
Ile Glu Gly Gly Trp Thr Gly Met Ile Asp Gly Trp Tyr Gly Tyr His
            355                 360                 365
His Glu Asn Ser Gln Gly Ser Gly Tyr Ala Ala Asp Lys Glu Ser Thr
370                 375                 380
Gln Lys Ala Ile Asp Gly Ile Thr Asn Lys Val Asn Ser Ile Ile Asp
385                 390                 395                 400
Lys Met Asn Thr Gln Phe Glu Ala Val Asp His Glu Phe Ser Asn Leu
                405                 410                 415
Glu Arg Arg Val Asp Asn Leu Asn Lys Arg Met Glu Asp Gly Phe Leu
            420                 425                 430
Asp Val Trp Thr Tyr Asn Ala Glu Leu Leu Val Leu Leu Glu Asn Glu
            435                 440                 445
Arg Thr Leu Asp Leu His Asp Ala Asn Val Lys Asn Leu Tyr Glu Lys
450                 455                 460
Val Lys Ser Gln Leu Arg Asp Asn Ala Lys Asp Leu Gly Asn Gly Cys
465                 470                 475                 480
Phe Glu Phe Trp His Lys Cys Asp Asp Glu Cys Ile Asn Ser Val Lys
                485                 490                 495
Asn Gly Thr Tyr Asp Tyr Pro Lys Tyr Gln Asp Glu Ser Lys Leu Asn
```

```
                    500                 505                 510
Arg Gln Glu Ile Asp Ser Val Lys Leu Glu Asn Leu Gly Val Tyr Gln
                515                 520                 525

Ile Leu Ala Ile Tyr Ser Thr Val Ser Ser Gly Leu Val Leu Val Gly
            530                 535                 540

Leu Ile Ile Ala Met Gly Leu Trp Met Cys Ser Asn Gly Ser Met Pro
545                 550                 555                 560

Cys Lys Ile Cys Ile
                565

<210> SEQ ID NO 20
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Val Lys Val Leu His Leu Leu Ile Ile Val Leu Gly Arg Tyr
1               5                   10                  15

Ser Ile Ala Asp Lys Ile Cys Ile Gly Tyr Leu Ser Asn Asn Ser Ser
            20                  25                  30

Asp Thr Val Asp Thr Leu Thr Glu Asn Gly Val Pro Val Thr Ser Ser
        35                  40                  45

Ile Asp Leu Val Glu Thr Asn His Thr Gly Thr Tyr Cys Ser Leu Asn
    50                  55                  60

Gly Ile Ser Pro Ile His Leu Gly Asp Cys Ser Phe Glu Gly Trp Ile
65                  70                  75                  80

Val Gly Asn Pro Ser Cys Ala Thr Asn Ile Asn Ile Arg Glu Trp Ser
                85                  90                  95

Tyr Leu Ile Glu Asp Pro Asn Ala Pro Asn Lys Leu Cys Phe Pro Gly
            100                 105                 110

Glu Leu Asp Asn Asn Gly Glu Leu Arg His Leu Phe Ser Gly Val Asn
        115                 120                 125

Ser Phe Ser Arg Thr Glu Leu Ile Ser Pro Ser Lys Trp Gly Asp Val
    130                 135                 140

Leu Asp Gly Val Thr Ala Ser Cys Leu Asp Lys Gly Ala Ser Ser Phe
145                 150                 155                 160

Tyr Arg Asn Leu Val Trp Leu Val Lys Gln Asn Asp Arg Tyr Pro Val
                165                 170                 175

Val Arg Gly Asp Tyr Asn Asn Thr Thr Gly Arg Asp Val Leu Val Leu
            180                 185                 190

Trp Gly Ile His His Pro Asp Thr Glu Thr Thr Ala Thr Lys Leu Tyr
        195                 200                 205

Val Asn Lys Asn Pro Tyr Thr Leu Val Ser Thr Lys Glu Trp Ser Lys
    210                 215                 220

Arg Tyr Glu Leu Glu Ile Gly Thr Arg Ile Gly Asp Gly Gln Arg Ser
225                 230                 235                 240

Trp Met Lys Ile Tyr Trp His Leu Met His Pro Gly Glu Arg Ile Met
                245                 250                 255

Phe Glu Ser Asn Gly Gly Leu Leu Ala Pro Arg Tyr Gly Tyr Ile Ile
            260                 265                 270

Glu Lys Tyr Gly Thr Gly Arg Ile Phe Gln Ser Gly Ile Arg Met Ala
        275                 280                 285

Lys Cys Asn Thr Lys Cys Gln Thr Ser Met Gly Gly Val Asn Thr Asn
```

```
                    290                 295                 300
Lys Thr Phe Gln Asn Ile Glu Arg Asn Ala Leu Gly Asp Cys Pro Lys
305                 310                 315                 320

Tyr Ile Lys Ser Gly Gln Leu Lys Leu Ala Thr Gly Leu Arg Asn Val
                325                 330                 335

Pro Ser Ile Gly Glu Arg Gly Leu Phe Gly Ala Ile Ala Gly Phe Ile
                340                 345                 350

Glu Gly Gly Trp Pro Gly Leu Ile Asn Gly Trp Tyr Gly Phe Gln His
                355                 360                 365

Gln Asn Glu Gln Gly Thr Gly Ile Ala Ala Asp Lys Ala Ser Thr Gln
                370                 375                 380

Lys Ala Ile Asn Glu Ile Thr Thr Lys Ile Asn Asn Ile Ile Glu Lys
385                 390                 395                 400

Met Asn Gly Asn Thr Asp Ser Ile Arg Gly Glu Phe Asn Gln Val Glu
                405                 410                 415

Lys Arg Ile Asn Met Leu Ala Asp Arg Val Asp Asp Ala Val Thr Asp
                420                 425                 430

Ile Trp Ser Tyr Asn Ala Lys Leu Leu Val Leu Ile Glu Asn Asp Arg
                435                 440                 445

Thr Leu Asp Leu His Asp Ala Asn Val Lys Asn Leu His Glu Gln Val
450                 455                 460

Lys Arg Ala Leu Lys Asn Asn Ala Ile Asp Glu Gly Asp Gly Cys Phe
465                 470                 475                 480

Asn Leu Leu His Lys Cys Asn Asp Ser Cys Met Glu Thr Ile Arg Asn
                485                 490                 495

Gly Thr Tyr Asn His Glu Asp Tyr Arg Glu Glu Ser Gln Leu Lys Arg
                500                 505                 510

Gln Glu Ile Glu Gly Ile Lys Leu Lys Thr Glu Asp Asn Val Tyr Lys
                515                 520                 525

Val Leu Ser Ile Tyr Ser Cys Ile Ala Ser Ser Ile Val Met Val Gly
                530                 535                 540

Leu Ile Leu Ala Phe Ile Met Trp Ala Cys Ser Ser Gly Asn Cys Arg
545                 550                 555                 560

Phe Asn Val Cys Ile
                565

<210> SEQ ID NO 21
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Glu Lys Phe Ile Ala Ile Ala Thr Leu Ala Ser Thr Asn Ala Tyr
1               5                   10                  15

Asp Arg Ile Cys Ile Gly Tyr Gln Ser Asn Asn Ser Thr Asp Thr Val
                20                  25                  30

Asn Thr Leu Ile Glu Gln Asn Val Pro Val Thr Gln Thr Met Glu Leu
            35                  40                  45

Val Glu Thr Glu Lys His Pro Ala Tyr Cys Asn Thr Asp Leu Gly Ala
        50                  55                  60

Pro Leu Glu Leu Arg Asp Cys Lys Ile Glu Ala Val Ile Tyr Gly Asn
65                  70                  75                  80

Pro Lys Cys Asp Ile His Leu Lys Asp Gln Gly Trp Ser Tyr Ile Val
```

-continued

```
                85                  90                  95
Glu Arg Pro Ser Ala Pro Glu Gly Met Cys Tyr Pro Gly Ser Val Glu
               100                 105                 110

Asn Leu Glu Glu Leu Arg Phe Val Phe Ser Ala Ala Ser Tyr Lys
               115                 120                 125

Arg Ile Arg Leu Phe Asp Tyr Ser Arg Trp Asn Val Thr Arg Ser Gly
               130                 135                 140

Thr Ser Lys Ala Cys Asn Ala Ser Thr Gly Gly Gln Ser Phe Tyr Arg
145                            150                 155                 160

Ser Ile Asn Trp Leu Thr Lys Lys Glu Pro Asp Thr Tyr Asp Phe Asn
                   165                 170                 175

Glu Gly Ala Tyr Val Asn Asn Glu Asp Gly Asp Ile Ile Phe Leu Trp
                   180                 185                 190

Gly Ile His His Pro Asp Thr Lys Glu Gln Thr Thr Leu Tyr Lys
                   195                 200                 205

Asn Ala Asn Thr Leu Ser Ser Val Thr Thr Asn Thr Ile Asn Arg Ser
210                            215                 220

Phe Gln Pro Asn Ile Gly Pro Arg Pro Leu Val Arg Gly Gln Gln Gly
225                            230                 235                 240

Arg Met Asp Tyr Tyr Trp Gly Ile Leu Lys Arg Gly Glu Thr Leu Lys
                   245                 250                 255

Ile Arg Thr Asn Gly Asn Leu Ile Ala Pro Glu Phe Gly Tyr Leu Leu
                   260                 265                 270

Lys Gly Glu Ser Tyr Gly Arg Ile Ile Gln Asn Glu Asp Ile Pro Ile
                   275                 280                 285

Gly Asn Cys Asn Thr Lys Cys Gln Thr Tyr Ala Gly Ala Ile Asn Ser
                   290                 295                 300

Ser Lys Pro Phe Gln Asn Ala Ser Arg His Tyr Met Gly Glu Cys Pro
305                            310                 315                 320

Lys Tyr Val Lys Lys Ala Ser Leu Arg Leu Ala Val Gly Leu Arg Asn
                   325                 330                 335

Thr Pro Ser Val Glu Pro Arg Gly Leu Phe Gly Ala Ile Ala Gly Phe
                   340                 345                 350

Ile Glu Gly Gly Trp Ser Gly Met Ile Asp Gly Trp Tyr Gly Phe His
                   355                 360                 365

His Ser Asn Ser Glu Gly Thr Gly Met Ala Ala Asp Gln Lys Ser Thr
                   370                 375                 380

Gln Glu Ala Ile Asp Lys Ile Thr Asn Lys Val Asn Asn Ile Val Asp
385                            390                 395                 400

Lys Met Asn Arg Glu Phe Glu Val Val Asn His Glu Phe Ser Glu Val
                   405                 410                 415

Glu Lys Arg Ile Asn Met Ile Asn Asp Lys Ile Asp Asp Gln Ile Glu
                   420                 425                 430

Asp Leu Trp Ala Tyr Asn Ala Glu Leu Leu Val Leu Leu Glu Asn Gln
                   435                 440                 445

Lys Thr Leu Asp Glu His Asp Ser Asn Val Lys Asn Leu Phe Asp Glu
                   450                 455                 460

Val Lys Arg Arg Leu Ser Ala Asn Ala Ile Asp Ala Gly Asn Gly Cys
465                            470                 475                 480

Phe Asp Ile Leu His Lys Cys Asp Asn Glu Cys Met Glu Thr Ile Lys
                   485                 490                 495

Asn Gly Thr Tyr Asp His Lys Tyr Glu Glu Glu Ala Lys Leu Glu
                   500                 505                 510
```

```
Arg Ser Lys Ile Asn Gly Val Lys Leu Glu Glu Asn Thr Thr Tyr Lys
        515                 520                 525

Ile Leu Ser Ile Tyr Ser Thr Val Ala Ala Ser Leu Cys Leu Ala Ile
    530                 535                 540

Leu Ile Ala Gly Gly Leu Ile Leu Gly Met Gln Asn Gly Ser Cys Arg
545                 550                 555                 560

Cys Met Phe Cys Ile
                565

<210> SEQ ID NO 22
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Glu Lys Thr Leu Leu Phe Ala Ala Ile Phe Leu Cys Val Lys Ala
1               5                   10                  15

Asp Glu Ile Cys Ile Gly Tyr Leu Ser Asn Asn Ser Thr Asp Lys Val
            20                  25                  30

Asp Thr Ile Ile Glu Asn Asn Val Thr Val Thr Ser Ser Val Glu Leu
        35                  40                  45

Val Glu Thr Glu His Thr Gly Ser Phe Cys Ser Ile Asn Gly Lys Gln
    50                  55                  60

Pro Ile Ser Leu Gly Asp Cys Ser Phe Ala Gly Trp Ile Leu Gly Asn
65                  70                  75                  80

Pro Met Cys Asp Glu Leu Ile Gly Lys Thr Ser Trp Ser Tyr Ile Val
                85                  90                  95

Glu Lys Pro Asn Pro Thr Asn Gly Ile Cys Tyr Pro Gly Thr Leu Glu
            100                 105                 110

Ser Glu Glu Glu Leu Arg Leu Lys Phe Ser Gly Val Leu Glu Phe Asn
        115                 120                 125

Lys Phe Glu Val Phe Thr Ser Asn Gly Trp Gly Ala Val Asn Ser Gly
130                 135                 140

Val Gly Val Thr Ala Ala Cys Lys Phe Gly Gly Ser Asn Ser Phe Phe
145                 150                 155                 160

Arg Asn Met Val Trp Leu Ile His Gln Ser Gln Thr Tyr Pro Val Ile
                165                 170                 175

Lys Arg Thr Phe Asn Asn Thr Lys Gly Arg Asp Val Leu Ile Val Trp
            180                 185                 190

Gly Ile His His Pro Ala Thr Leu Thr Glu His Gln Asp Leu Tyr Lys
        195                 200                 205

Lys Asp Ser Ser Tyr Val Ala Val Gly Ser Glu Thr Tyr Asn Arg Arg
210                 215                 220

Phe Thr Pro Glu Ile Asn Thr Arg Pro Arg Val Asn Gly Gln Ala Gly
225                 230                 235                 240

Arg Met Thr Phe Tyr Trp Lys Ile Val Lys Pro Gly Glu Ser Ile Thr
                245                 250                 255

Phe Glu Ser Asn Gly Ala Phe Leu Ala Pro Arg Tyr Ala Phe Glu Ile
            260                 265                 270

Val Ser Val Gly Asn Gly Lys Leu Phe Arg Ser Glu Leu Asn Ile Glu
        275                 280                 285

Ser Cys Ser Thr Lys Cys Gln Thr Glu Ile Gly Gly Ile Asn Thr Asn
290                 295                 300
```

Lys Ser Phe His Asn Val His Arg Asn Thr Ile Gly Asp Cys Pro Lys
305                 310                 315                 320

Tyr Val Asn Val Lys Ser Leu Lys Leu Ala Thr Gly Pro Arg Asn Val
            325                 330                 335

Pro Ala Ile Ala Ser Arg Gly Leu Phe Gly Ile Ala Gly Phe Ile
        340                 345                 350

Glu Gly Gly Trp Pro Gly Leu Ile Asn Gly Trp Tyr Gly Phe Gln His
            355                 360                 365

Arg Asp Glu Glu Gly Thr Gly Ile Ala Ala Asp Lys Glu Ser Thr Gln
        370                 375                 380

Lys Ala Ile Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
                405                 410                 415

Glu Arg Ile Asn Gln Leu Ser Lys His Val Asp Asp Ser Val Val Asp
            420                 425                 430

Ile Trp Ser Tyr Asn Ala Gln Leu Leu Val Leu Leu Glu Asn Glu Lys
        435                 440                 445

Thr Leu Asp Leu His Asp Ser Asn Val Arg Asn Leu His Glu Lys Val
450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Lys Cys Ile Glu Arg Val Arg Asn
                485                 490                 495

Gly Thr Tyr Asp His Lys Glu Phe Glu Glu Ser Lys Ile Asn Arg
            500                 505                 510

Gln Glu Ile Glu Gly Val Lys Leu Asp Ser Ser Gly Asn Val Tyr Lys
        515                 520                 525

Ile Leu Ser Ile Tyr Ser Cys Ile Ala Ser Ser Leu Val Leu Ala Ala
530                 535                 540

Leu Ile Met Gly Phe Met Phe Trp Ala Cys Ser Asn Gly Ser Cys Arg
545                 550                 555                 560

Cys Thr Ile Cys Ile
            565

<210> SEQ ID NO 23
<211> LENGTH: 564
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Glu Lys Phe Ile Ile Leu Ser Thr Val Leu Ala Ala Ser Phe Ala
1               5                   10                  15

Tyr Asp Lys Ile Cys Ile Gly Tyr Gln Thr Asn Asn Ser Thr Glu Thr
            20                  25                  30

Val Asn Thr Leu Ser Glu Gln Asn Val Pro Val Thr Gln Val Glu Glu
        35                  40                  45

Leu Val His Arg Gly Ile Asp Pro Ile Leu Cys Gly Thr Glu Leu Gly
    50                  55                  60

Ser Pro Leu Val Leu Asp Asp Cys Ser Leu Glu Gly Leu Ile Leu Gly
65                  70                  75                  80

Asn Pro Lys Cys Asp Leu Tyr Leu Asn Gly Arg Glu Trp Ser Tyr Ile
                85                  90                  95

-continued

```
Val Glu Arg Pro Lys Glu Met Glu Gly Val Cys Tyr Pro Gly Ser Ile
            100                 105                 110

Glu Asn Gln Glu Glu Leu Arg Ser Leu Phe Ser Ser Ile Lys Lys Tyr
            115                 120                 125

Glu Arg Val Lys Met Phe Asp Phe Thr Lys Trp Asn Val Thr Tyr Thr
            130                 135                 140

Gly Thr Ser Lys Ala Cys Asn Asn Thr Ser Asn Gln Gly Ser Phe Tyr
145                 150                 155                 160

Arg Ser Met Arg Trp Leu Thr Leu Lys Ser Gly Gln Phe Pro Val Gln
                165                 170                 175

Thr Asp Glu Tyr Lys Asn Thr Arg Asp Ser Asp Ile Val Phe Thr Trp
            180                 185                 190

Ala Ile His His Pro Pro Thr Ser Asp Glu Gln Val Lys Leu Tyr Lys
            195                 200                 205

Asn Pro Asp Thr Leu Ser Ser Val Thr Thr Val Glu Ile Asn Arg Ser
            210                 215                 220

Phe Lys Pro Asn Ile Gly Pro Arg Pro Leu Val Arg Gly Gln Gln Gly
225                 230                 235                 240

Arg Met Asp Tyr Tyr Trp Ala Val Leu Lys Pro Gly Gln Thr Val Lys
                245                 250                 255

Ile Gln Thr Asn Gly Asn Leu Ile Ala Pro Glu Tyr Gly His Leu Ile
            260                 265                 270

Thr Gly Lys Ser His Gly Arg Ile Leu Lys Asn Asn Leu Pro Met Gly
            275                 280                 285

Gln Cys Val Thr Glu Cys Gln Leu Asn Glu Gly Val Met Asn Thr Ser
            290                 295                 300

Lys Pro Phe Gln Asn Thr Ser Lys His Tyr Ile Gly Lys Cys Pro Lys
305                 310                 315                 320

Tyr Ile Pro Ser Gly Ser Leu Lys Leu Ala Ile Gly Leu Arg Asn Val
                325                 330                 335

Pro Gln Val Gln Asp Arg Gly Leu Phe Gly Ala Ile Ala Gly Phe Ile
            340                 345                 350

Glu Gly Gly Trp Pro Gly Leu Val Ala Gly Trp Tyr Gly Phe Gln His
            355                 360                 365

Gln Asn Ala Glu Gly Thr Gly Ile Ala Ala Asp Arg Asp Ser Thr Gln
            370                 375                 380

Arg Ala Ile Asp Asn Met Gln Asn Lys Leu Asn Asn Val Ile Asp Lys
385                 390                 395                 400

Met Asn Lys Gln Phe Glu Val Val Asn His Glu Phe Ser Glu Val Glu
                405                 410                 415

Ser Arg Ile Asn Met Ile Asn Ser Lys Ile Asp Asp Gln Ile Thr Asp
            420                 425                 430

Ile Trp Ala Tyr Asn Ala Glu Leu Leu Val Leu Leu Glu Asn Gln Lys
            435                 440                 445

Thr Leu Asp Glu His Asp Ala Asn Val Arg Asn Leu His Asp Arg Val
            450                 455                 460

Arg Arg Val Leu Arg Glu Asn Ala Ile Asp Thr Gly Asp Gly Cys Phe
465                 470                 475                 480

Glu Ile Leu His Lys Cys Asp Asn Asn Cys Met Asp Thr Ile Arg Asn
                485                 490                 495

Gly Thr Tyr Asn His Lys Glu Tyr Glu Glu Glu Ser Lys Ile Glu Arg
            500                 505                 510

Gln Lys Val Asn Gly Val Lys Leu Glu Glu Asn Ser Thr Tyr Lys Ile
            515                 520                 525
```

-continued

```
Leu Ser Ile Tyr Ser Ser Val Ala Ser Ser Leu Val Leu Leu Leu Met
    530                 535                 540
Ile Ile Gly Gly Phe Ile Phe Gly Cys Gln Asn Gly Asn Val Arg Cys
545                 550                 555                 560
Thr Phe Cys Ile

<210> SEQ ID NO 24
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ala Leu Asn Val Ile Ala Thr Leu Thr Leu Ile Ser Val Cys Val
1               5                   10                  15
His Ala Asp Arg Ile Cys Val Gly Tyr Leu Ser Thr Asn Ser Ser Glu
                20                  25                  30
Arg Val Asp Thr Leu Leu Glu Asn Gly Val Pro Val Thr Ser Ser Ile
            35                  40                  45
Asp Leu Ile Glu Thr Asn His Thr Gly Thr Tyr Cys Ser Leu Asn Gly
        50                  55                  60
Val Ser Pro Val His Leu Gly Asp Cys Ser Phe Glu Gly Trp Ile Val
65                  70                  75                  80
Gly Asn Pro Ala Cys Thr Ser Asn Phe Gly Ile Arg Glu Trp Ser Tyr
                85                  90                  95
Leu Ile Glu Asp Pro Ala Ala Pro His Gly Leu Cys Tyr Pro Gly Glu
                100                 105                 110
Leu Asn Asn Asn Gly Glu Leu Arg His Leu Phe Ser Gly Ile Arg Ser
            115                 120                 125
Phe Ser Arg Thr Glu Leu Ile Pro Pro Thr Ser Trp Gly Glu Val Leu
        130                 135                 140
Asp Gly Thr Thr Ser Ala Cys Arg Asp Asn Thr Gly Thr Asn Ser Phe
145                 150                 155                 160
Tyr Arg Asn Leu Val Trp Phe Ile Lys Lys Asn Thr Arg Tyr Pro Val
                165                 170                 175
Ile Ser Lys Thr Tyr Asn Asn Thr Thr Gly Arg Asp Val Leu Val Leu
                180                 185                 190
Trp Gly Ile His His Pro Val Ser Val Asp Glu Thr Lys Thr Leu Tyr
            195                 200                 205
Val Asn Ser Asp Pro Tyr Thr Leu Val Ser Thr Lys Ser Trp Ser Glu
        210                 215                 220
Lys Tyr Lys Leu Glu Thr Gly Val Arg Pro Gly Tyr Asn Gly Gln Arg
225                 230                 235                 240
Ser Trp Met Lys Ile Tyr Trp Ser Leu Ile His Pro Gly Glu Met Ile
                245                 250                 255
Thr Phe Glu Ser Asn Gly Gly Phe Leu Ala Pro Arg Tyr Gly Tyr Ile
                260                 265                 270
Ile Glu Glu Tyr Gly Lys Gly Arg Ile Phe Gln Ser Arg Ile Arg Met
            275                 280                 285
Ser Arg Cys Asn Thr Lys Cys Gln Thr Ser Val Gly Gly Ile Asn Thr
        290                 295                 300
Asn Arg Thr Phe Gln Asn Ile Asp Lys Asn Ala Leu Gly Asp Cys Pro
305                 310                 315                 320
```

```
Lys Tyr Ile Lys Ser Gly Gln Leu Lys Leu Ala Thr Gly Leu Arg Asn
                325                 330                 335

Val Pro Ala Ile Ser Asn Arg Gly Leu Phe Gly Ala Ile Ala Gly Phe
            340                 345                 350

Ile Glu Gly Gly Trp Pro Gly Leu Ile Asn Gly Trp Tyr Gly Phe Gln
        355                 360                 365

His Gln Asn Glu Gln Gly Thr Gly Ile Ala Asp Lys Glu Ser Thr
    370                 375                 380

Gln Lys Ala Ile Asp Gln Ile Thr Thr Lys Ile Asn Asn Ile Ile Asp
385                 390                 395                 400

Lys Met Asn Gly Asn Tyr Asp Ser Ile Arg Gly Glu Phe Asn Gln Val
                405                 410                 415

Glu Lys Arg Ile Asn Met Leu Ala Asp Arg Ile Asp Asp Ala Val Thr
            420                 425                 430

Asp Ile Trp Ser Tyr Asn Ala Lys Leu Leu Val Leu Leu Glu Asn Asp
        435                 440                 445

Lys Thr Leu Asp Met His Asp Ala Asn Val Lys Asn Leu His Glu Gln
    450                 455                 460

Val Arg Arg Glu Leu Lys Asp Asn Ala Ile Asp Glu Gly Asn Gly Cys
465                 470                 475                 480

Phe Glu Leu Leu His Lys Cys Asn Asp Ser Cys Met Glu Thr Ile Arg
                485                 490                 495

Asn Gly Thr Tyr Asp His Thr Glu Tyr Ala Glu Glu Ser Lys Leu Lys
            500                 505                 510

Arg Gln Glu Ile Asp Gly Ile Lys Leu Lys Ser Glu Asp Asn Val Tyr
        515                 520                 525

Lys Ala Leu Ser Ile Tyr Ser Cys Ile Ala Ser Val Val Leu Val
    530                 535                 540

Gly Leu Ile Leu Ser Phe Ile Met Trp Ala Cys Ser Ser Gly Asn Cys
545                 550                 555                 560

Arg Phe Asn Val Cys Ile
                565

<210> SEQ ID NO 25
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Glu Thr Ile Ser Leu Ile Thr Ile Leu Leu Val Val Thr Ala Ser
1               5                   10                  15

Asn Ala Asp Lys Ile Cys Ile Gly His Gln Ser Thr Asn Ser Thr Glu
                20                  25                  30

Thr Val Asp Thr Leu Thr Glu Thr Asn Val Pro Val Thr His Ala Lys
            35                  40                  45

Glu Leu Leu His Thr Glu His Asn Gly Met Leu Cys Ala Thr Ser Leu
    50                  55                  60

Gly His Pro Leu Ile Leu Asp Thr Cys Thr Ile Glu Gly Leu Val Tyr
65                  70                  75                  80

Gly Asn Pro Ser Cys Asp Leu Leu Leu Gly Arg Glu Trp Ser Tyr
                85                  90                  95

Ile Val Glu Arg Ser Ser Ala Val Asn Gly Thr Cys Tyr Pro Gly Asn
            100                 105                 110
```

```
Val Glu Asn Leu Glu Glu Leu Arg Thr Leu Phe Ser Ser Ala Ser Ser
            115                 120                 125

Tyr Gln Arg Ile Gln Ile Phe Pro Asp Thr Thr Asn Val Val Tyr Thr
        130                 135                 140

Asn Gly Ser Arg Ala Cys Ser Gly Ser Phe Tyr Arg Ser Met Arg Trp
145                 150                 155                 160

Leu Ile Gln Lys Ser Gly Phe Tyr Pro Val Gln Asp Ala Gln Tyr Thr
                165                 170                 175

Asn Asn Arg Gly Lys Ser Ile Leu Phe Val Trp Gly Ile His His Pro
            180                 185                 190

Pro Thr Tyr Thr Glu Gln Thr Asn Leu Tyr Ile Arg Asn Asp Thr Thr
        195                 200                 205

Thr Ser Val Thr Thr Glu Asp Leu Asn Arg Thr Phe Lys Pro Val Ile
210                 215                 220

Gly Pro Arg Pro Leu Val Asn Gly Leu Gln Gly Arg Ile Asp Tyr Tyr
225                 230                 235                 240

Trp Ser Val Leu Lys Pro Gly Gln Thr Leu Arg Val Arg Ser Asn Gly
                245                 250                 255

Asn Leu Ile Ala Pro Trp Tyr Gly His Val Leu Ser Gly Gly Ser His
            260                 265                 270

Gly Arg Ile Leu Lys Tyr Asp Leu Lys Gly Gly Asn Cys Val Val Gln
        275                 280                 285

Cys Gln Thr Glu Lys Gly Gly Leu Asn Ser Thr Leu Pro Phe His Asn
290                 295                 300

Ile Ser Lys Tyr Ala Phe Gly Thr Cys Pro Lys Tyr Val Arg Val Asn
305                 310                 315                 320

Ser Leu Lys Leu Ala Val Gly Leu Arg Asn Val Pro Ala Arg Ser Ser
                325                 330                 335

Arg Gly Leu Phe Gly Ala Ile Ala Gly Phe Ile Glu Gly Gly Trp Pro
            340                 345                 350

Gly Leu Val Ala Gly Trp Tyr Gly Phe Gln His Ser Asn Asp Gln Gly
        355                 360                 365

Val Gly Met Ala Ala Asp Arg Asp Ser Thr Gln Lys Ala Ile Asp Lys
370                 375                 380

Ile Thr Ser Lys Val Asn Asn Ile Val Asp Lys Met Asn Lys Gln Tyr
385                 390                 395                 400

Glu Ile Ile Asp His Glu Phe Ser Glu Val Glu Thr Arg Leu Asn Met
                405                 410                 415

Ile Asn Asn Lys Ile Asp Asp Gln Ile Gln Asp Val Trp Ala Tyr Asn
            420                 425                 430

Ala Glu Leu Leu Val Leu Leu Glu Asn Gln Lys Thr Leu Asp Glu His
        435                 440                 445

Asp Ala Asn Val Asn Asn Leu Tyr Asn Lys Val Lys Arg Ala Leu Gly
450                 455                 460

Ser Asn Ala Met Glu Asp Gly Lys Gly Cys Phe Glu Leu Tyr His Lys
465                 470                 475                 480

Cys Asp Asp Gln Cys Met Glu Thr Ile Arg Asn Gly Thr Tyr Asn Arg
                485                 490                 495

Arg Lys Tyr Arg Glu Glu Ser Arg Leu Glu Arg Gln Lys Ile Glu Gly
            500                 505                 510

Val Lys Leu Glu Ser Glu Gly Thr Tyr Lys Ile Leu Thr Ile Tyr Ser
        515                 520                 525

Thr Val Ala Ser Ser Leu Val Leu Ala Met Gly Phe Ala Ala Phe Leu
530                 535                 540
```

```
Phe Trp Ala Asn Ser Asn Gly Ser Cys Arg Cys Asn Ile Cys Ile
545                 550                 555
```

<210> SEQ ID NO 26
<211> LENGTH: 533
<212> TYPE: PRT
<213> ORGANISM: Influenza A virus

<400> SEQUENCE: 26

```
Met Glu Lys Asn Val Thr Val Thr His Ala Gln Asp Ile Leu Glu Lys
1               5                   10                  15

Thr His Asn Gly Lys Leu Cys Asp Leu Asp Gly Val Lys Pro Leu Ile
            20                  25                  30

Leu Arg Asp Cys Ser Val Ala Gly Trp Leu Leu Gly Asn Pro Met Cys
        35                  40                  45

Asp Glu Phe Leu Asn Val Pro Glu Trp Ser Tyr Ile Val Glu Lys Ile
    50                  55                  60

Asn Pro Ala Asn Asp Leu Cys Tyr Pro Gly Asn Phe Asn Asp Tyr Glu
65                  70                  75                  80

Glu Leu Lys His Leu Leu Ser Arg Ile Asn His Phe Glu Lys Ile Gln
                85                  90                  95

Ile Ile Pro Lys Ser Ser Trp Ser Asp His Glu Ala Ser Ser Gly Val
            100                 105                 110

Ser Ser Ala Cys Pro Tyr Gln Gly Arg Ser Ser Phe Phe Arg Asn Val
        115                 120                 125

Val Trp Leu Ile Lys Lys Asn Asn Ala Tyr Pro Thr Ile Lys Arg Ser
    130                 135                 140

Tyr Asn Asn Thr Asn Gln Glu Asp Leu Leu Val Leu Trp Gly Ile His
145                 150                 155                 160

His Pro Asn Asp Ala Ala Glu Gln Thr Arg Leu Tyr Gln Asn Pro Thr
                165                 170                 175

Thr Tyr Ile Ser Val Gly Thr Ser Thr Leu Asn Gln Arg Leu Val Pro
            180                 185                 190

Lys Ile Ala Thr Arg Ser Lys Val Asn Gly Gln Asn Gly Arg Met Glu
        195                 200                 205

Phe Phe Trp Thr Ile Leu Lys Pro Asn Asp Ala Ile Asn Phe Glu Ser
    210                 215                 220

Asn Gly Asn Phe Ile Ala Pro Glu Asn Ala Tyr Lys Ile Val Lys Lys
225                 230                 235                 240

Gly Asp Ser Thr Ile Met Lys Ser Glu Leu Glu Tyr Gly Asn Cys Asn
                245                 250                 255

Thr Lys Cys Gln Thr Pro Ile Gly Ala Ile Asn Ser Ser Met Pro Phe
            260                 265                 270

His Asn Ile His Pro Leu Thr Ile Gly Glu Cys Pro Lys Tyr Val Lys
        275                 280                 285

Ser Asn Arg Leu Val Leu Ala Thr Gly Leu Arg Asn Ser Pro Gln Gly
    290                 295                 300

Glu Arg Arg Arg Lys Lys Arg Gly Leu Phe Gly Ala Ile Ala Gly Phe
305                 310                 315                 320

Ile Glu Gly Gly Trp Gln Gly Met Val Asp Gly Trp Tyr Gly Tyr His
                325                 330                 335

His Ser Asn Glu Gln Gly Ser Gly Tyr Ala Ala Asp Lys Glu Ser Thr
            340                 345                 350

Gln Lys Ala Ile Asp Gly Val Thr Asn Lys Val Asn Ser Ile Ile Asp
        355                 360                 365
```

```
Lys Met Asn Thr Gln Phe Glu Ala Val Gly Arg Glu Phe Asn Asn Leu
    370                 375                 380

Glu Arg Arg Ile Glu Asn Leu Asn Lys Lys Met Glu Asp Gly Phe Leu
385                 390                 395                 400

Asp Val Trp Thr Tyr Asn Ala Glu Leu Leu Val Leu Met Glu Asn Glu
                405                 410                 415

Arg Thr Leu Asp Phe His Asp Ser Asn Val Lys Asn Leu Tyr Asp Lys
            420                 425                 430

Val Arg Leu Gln Leu Arg Asp Asn Ala Lys Glu Leu Gly Asn Gly Cys
        435                 440                 445

Phe Glu Phe Tyr His Arg Cys Asp Asn Glu Cys Met Glu Ser Val Arg
    450                 455                 460

Asn Gly Thr Tyr Asp Tyr Pro Gln Tyr Ser Glu Glu Ala Arg Leu Lys
465                 470                 475                 480

Arg Glu Glu Ile Ser Gly Val Lys Leu Glu Ser Ile Gly Thr Tyr Gln
                485                 490                 495

Ile Leu Ser Ile Tyr Ser Thr Val Ala Ser Ser Leu Ala Leu Ala Ile
            500                 505                 510

Met Val Ala Gly Leu Ser Leu Trp Met Cys Ser Asn Gly Ser Leu Gln
        515                 520                 525

Cys Arg Ile Cys Ile
    530

<210> SEQ ID NO 27
<211> LENGTH: 533
<212> TYPE: PRT
<213> ORGANISM: Influenza A virus

<400> SEQUENCE: 27

Met Glu Lys Asn Val Thr Val Thr His Ala Gln Asp Ile Leu Glu Lys
1               5                   10                  15

Thr His Asn Gly Lys Leu Cys Asp Leu Asp Gly Val Lys Pro Leu Ile
                20                  25                  30

Leu Arg Asp Cys Ser Val Ala Gly Trp Leu Leu Gly Asn Pro Met Cys
            35                  40                  45

Asp Glu Phe Leu Asn Val Pro Glu Trp Ser Tyr Ile Val Glu Lys Ile
50                  55                  60

Asn Pro Ala Asn Asp Leu Cys Tyr Pro Gly Asn Phe Asn Asp Tyr Glu
65                  70                  75                  80

Glu Leu Lys His Leu Leu Ser Arg Ile Asn His Phe Glu Lys Ile Gln
                85                  90                  95

Ile Ile Pro Lys Ser Ser Trp Ser Asp His Glu Ala Ser Ser Gly Val
            100                 105                 110

Ser Ser Ala Cys Pro Tyr Gln Gly Arg Ser Ser Phe Phe Arg Asn Val
        115                 120                 125

Val Trp Leu Ile Lys Lys Asp Asn Ala Tyr Pro Thr Ile Lys Arg Ser
    130                 135                 140

Tyr Asn Asn Thr Asn Gln Glu Asp Leu Leu Val Leu Trp Gly Ile His
145                 150                 155                 160

His Pro Asn Asp Ala Ala Glu Gln Thr Arg Leu Tyr Gln Asn Pro Thr
                165                 170                 175

Thr Tyr Ile Ser Val Gly Thr Ser Thr Leu Asn Gln Arg Leu Val Pro
            180                 185                 190

Lys Ile Ala Thr Arg Ser Lys Val Asn Gly Gln Asn Gly Arg Met Glu
        195                 200                 205
```

Phe Phe Trp Thr Ile Leu Lys Pro Asn Asp Ala Ile Asn Phe Glu Ser
                210                 215                 220

Asn Gly Asn Phe Ile Ala Pro Glu Asn Ala Tyr Lys Ile Val Lys Lys
225                 230                 235                 240

Gly Asp Ser Thr Ile Met Lys Ser Glu Leu Glu Tyr Gly Asn Cys Asn
                245                 250                 255

Thr Lys Cys Gln Thr Pro Ile Gly Ala Ile Asn Ser Ser Met Pro Phe
                260                 265                 270

His Asn Ile His Pro Leu Thr Ile Gly Glu Cys Pro Lys Tyr Val Lys
                275                 280                 285

Ser Asn Arg Leu Val Leu Ala Thr Gly Leu Arg Asn Ser Pro Gln Gly
                290                 295                 300

Glu Arg Arg Arg Lys Lys Arg Gly Leu Phe Gly Ala Ile Ala Gly Phe
305                 310                 315                 320

Ile Glu Gly Gly Trp Gln Gly Met Val Asp Gly Trp Tyr Gly Tyr His
                325                 330                 335

His Ser Asn Glu Gln Gly Ser Gly Tyr Ala Ala Asp Lys Glu Ser Thr
                340                 345                 350

Gln Lys Ala Ile Asp Gly Val Thr Asn Lys Val Asn Ser Ile Ile Asp
                355                 360                 365

Lys Met Asn Thr Gln Phe Glu Ala Val Gly Arg Glu Phe Asn Asn Leu
                370                 375                 380

Glu Arg Arg Ile Glu Asn Leu Asn Lys Lys Met Glu Asp Gly Phe Leu
385                 390                 395                 400

Asp Val Trp Thr Tyr Asn Ala Glu Leu Leu Val Leu Met Glu Asn Glu
                405                 410                 415

Arg Thr Leu Asp Phe His Asp Ser Asn Val Lys Asn Leu Tyr Asp Lys
                420                 425                 430

Val Arg Leu Gln Leu Arg Asp Asn Ala Lys Glu Leu Gly Asn Gly Cys
                435                 440                 445

Phe Glu Phe Tyr His Arg Cys Asp Asn Glu Cys Met Glu Ser Val Arg
                450                 455                 460

Asn Gly Thr Tyr Asp Tyr Pro Gln Tyr Ser Glu Glu Ala Arg Leu Lys
465                 470                 475                 480

Arg Glu Glu Ile Ser Gly Val Lys Leu Glu Ser Ile Gly Thr Tyr Gln
                485                 490                 495

Ile Leu Ser Ile Tyr Ser Thr Val Ala Ser Ser Leu Ala Leu Ala Ile
                500                 505                 510

Met Val Ala Gly Leu Ser Leu Trp Met Cys Ser Asn Gly Ser Leu Gln
                515                 520                 525

Cys Arg Ile Cys Ile
            530

<210> SEQ ID NO 28
<211> LENGTH: 533
<212> TYPE: PRT
<213> ORGANISM: Influenza A virus

<400> SEQUENCE: 28

Met Glu Lys Asn Val Thr Val Thr His Ala Gln Asp Ile Leu Glu Lys
1               5                   10                  15

Thr His Asn Gly Lys Leu Cys Asp Leu Asp Gly Val Lys Pro Leu Ile
                20                  25                  30

Leu Arg Asp Cys Ser Val Ala Gly Trp Leu Leu Gly Asn Pro Met Cys
                35                  40                  45

-continued

Asp Glu Phe Leu Asn Val Pro Glu Trp Ser Tyr Ile Val Glu Lys Ile
     50                  55                  60
Asn Pro Ala Asn Asp Leu Cys Tyr Pro Gly Asn Phe Asn Asp Tyr Glu
 65                  70                  75                  80
Glu Leu Lys His Leu Leu Ser Arg Ile Asn His Phe Glu Lys Ile Gln
                 85                  90                  95
Ile Ile Pro Lys Ser Ser Trp Ser Asp His Glu Ala Ser Ser Gly Val
            100                 105                 110
Ser Ser Ala Cys Pro Tyr Gln Gly Arg Ser Ser Phe Phe Arg Asn Val
            115                 120                 125
Val Trp Leu Ile Lys Lys Asp Asn Ala Tyr Pro Thr Ile Lys Arg Ser
    130                 135                 140
Tyr Asn Asn Thr Asn Gln Glu Asp Leu Leu Val Leu Trp Gly Ile His
145                 150                 155                 160
His Pro Asn Asp Ala Ala Glu Gln Thr Arg Leu Tyr Gln Asn Pro Thr
                165                 170                 175
Thr Tyr Ile Ser Val Gly Thr Ser Thr Leu Asn Gln Arg Leu Val Pro
            180                 185                 190
Lys Ile Ala Thr Arg Ser Lys Val Asn Gly Gln Ser Gly Arg Met Glu
            195                 200                 205
Phe Phe Trp Thr Ile Leu Lys Pro Asn Asp Ala Ile Asn Phe Glu Ser
    210                 215                 220
Asn Gly Asn Phe Ile Ala Pro Glu Asn Ala Tyr Lys Ile Val Lys Lys
225                 230                 235                 240
Gly Asp Ser Thr Ile Met Lys Ser Glu Leu Glu Tyr Gly Asn Cys Asn
                245                 250                 255
Thr Lys Cys Gln Thr Pro Ile Gly Ala Ile Asn Ser Ser Met Pro Phe
            260                 265                 270
His Asn Ile His Pro Leu Thr Ile Gly Glu Cys Pro Lys Tyr Val Lys
            275                 280                 285
Ser Asn Arg Leu Val Leu Ala Thr Gly Leu Arg Asn Ser Pro Gln Gly
    290                 295                 300
Glu Arg Arg Arg Lys Lys Arg Gly Leu Phe Gly Ala Ile Ala Gly Phe
305                 310                 315                 320
Ile Glu Gly Gly Trp Gln Gly Met Val Asp Gly Trp Tyr Gly Tyr His
                325                 330                 335
His Ser Asn Glu Gln Gly Ser Gly Tyr Ala Ala Asp Lys Glu Ser Thr
            340                 345                 350
Gln Lys Ala Ile Asp Gly Val Thr Asn Lys Val Asn Ser Ile Ile Asp
            355                 360                 365
Lys Met Asn Thr Gln Phe Glu Ala Val Gly Arg Glu Phe Asn Asn Leu
    370                 375                 380
Glu Arg Arg Ile Glu Asn Leu Asn Lys Lys Met Glu Asp Gly Phe Leu
385                 390                 395                 400
Asp Val Trp Thr Tyr Asn Ala Glu Leu Leu Val Leu Met Glu Asn Glu
                405                 410                 415
Arg Thr Leu Asp Phe His Asp Ser Asn Val Lys Asn Leu Tyr Asp Lys
            420                 425                 430
Val Arg Leu Gln Leu Arg Asp Asn Ala Lys Glu Leu Gly Asn Gly Cys
            435                 440                 445
Phe Glu Phe Tyr His Arg Cys Asp Asn Glu Cys Met Glu Ser Val Arg
    450                 455                 460
Asn Gly Thr Tyr Asp Tyr Pro Gln Tyr Ser Glu Glu Ala Arg Leu Lys

```
                465                 470                 475                 480
Arg Glu Glu Ile Ser Gly Val Lys Leu Glu Ser Ile Gly Thr Tyr Gln
                    485                 490                 495

Ile Leu Ser Ile Tyr Ser Thr Val Ala Ser Ser Leu Ala Leu Ala Ile
            500                 505                 510

Met Val Ala Gly Leu Ser Leu Trp Met Cys Ser Asn Gly Ser Leu Gln
        515                 520                 525

Cys Arg Ile Cys Ile
    530

<210> SEQ ID NO 29
<211> LENGTH: 533
<212> TYPE: PRT
<213> ORGANISM: Influenza A virus

<400> SEQUENCE: 29

Met Glu Lys Asn Val Thr Val Thr His Ala Gln Asp Ile Leu Glu Lys
1               5                   10                  15

Thr His Asn Gly Lys Leu Cys Asp Leu Asp Gly Val Lys Pro Leu Ile
            20                  25                  30

Leu Arg Asp Cys Ser Val Ala Gly Trp Leu Leu Gly Asn Pro Met Cys
        35                  40                  45

Asp Glu Phe Leu Asn Val Pro Glu Trp Ser Tyr Ile Val Glu Lys Ile
50                  55                  60

Asn Pro Ala Asn Asp Leu Cys Tyr Pro Gly Asn Phe Asn Asp Tyr Glu
65                  70                  75                  80

Glu Leu Lys His Leu Leu Ser Arg Ile Asn His Phe Glu Lys Ile Gln
                85                  90                  95

Ile Ile Pro Lys Ser Ser Trp Ser Asp His Glu Ala Ser Ser Gly Val
            100                 105                 110

Ser Ser Ala Cys Pro Tyr Gln Gly Arg Ser Ser Phe Phe Arg Asn Val
        115                 120                 125

Val Trp Leu Ile Lys Lys Asp Asn Ala Tyr Pro Thr Ile Lys Arg Ser
130                 135                 140

Tyr Asn Asn Thr Asn Gln Glu Asp Leu Leu Val Leu Trp Gly Ile His
145                 150                 155                 160

His Pro Asn Asp Ala Ala Glu Gln Thr Arg Leu Tyr Gln Asn Pro Thr
                165                 170                 175

Thr Tyr Ile Ser Val Gly Thr Ser Thr Leu Asn Gln Arg Leu Val Pro
            180                 185                 190

Lys Ile Ala Thr Arg Ser Lys Val Asn Gly Gln Ser Gly Arg Met Glu
        195                 200                 205

Phe Phe Trp Thr Ile Leu Lys Pro Asn Asp Ala Ile Asn Phe Glu Ser
    210                 215                 220

Asn Gly Asn Phe Ile Ala Pro Glu Asn Ala Tyr Lys Ile Val Lys Lys
225                 230                 235                 240

Gly Asp Ser Thr Ile Met Lys Ser Glu Leu Glu Tyr Gly Asn Cys Asn
                245                 250                 255

Thr Lys Cys Gln Thr Pro Ile Gly Ala Ile Asn Ser Ser Met Pro Phe
            260                 265                 270

His Asn Ile His Pro Leu Thr Ile Gly Glu Cys Pro Lys Tyr Val Lys
        275                 280                 285

Ser Asn Arg Leu Val Leu Ala Thr Gly Leu Arg Asn Ser Pro Gln Gly
    290                 295                 300

Glu Arg Arg Arg Lys Lys Arg Gly Leu Phe Gly Ala Ile Ala Gly Phe
```

-continued

```
              305                 310                 315                 320

Ile Glu Gly Gly Trp Gln Gly Met Val Asp Gly Trp Tyr Gly Tyr His
                325                 330                 335

His Ser Asn Glu Gln Gly Ser Gly Tyr Ala Ala Asp Lys Glu Ser Thr
                340                 345                 350

Gln Lys Ala Ile Asp Gly Val Thr Asn Lys Val Asn Ser Ile Ile Asp
                355                 360                 365

Lys Met Asn Thr Gln Phe Glu Ala Val Gly Arg Glu Phe Asn Asn Leu
            370                 375                 380

Glu Arg Arg Ile Glu Asn Leu Asn Lys Lys Met Glu Asp Gly Phe Leu
385                 390                 395                 400

Asp Val Trp Thr Tyr Asn Ala Glu Leu Leu Val Leu Met Glu Asn Glu
                405                 410                 415

Arg Thr Leu Asp Phe His Asp Ser Asn Val Lys Asn Leu Tyr Asp Lys
                420                 425                 430

Val Arg Leu Gln Leu Arg Asp Asn Ala Lys Glu Leu Gly Asn Gly Cys
                435                 440                 445

Phe Glu Phe Tyr His Arg Cys Asp Asn Glu Cys Met Glu Ser Val Arg
            450                 455                 460

Asn Gly Thr Tyr Asp Tyr Pro Gln Tyr Ser Glu Glu Ala Arg Leu Lys
465                 470                 475                 480

Arg Glu Glu Ile Ser Gly Val Lys Leu Glu Ser Ile Gly Thr Tyr Gln
                485                 490                 495

Ile Leu Ser Ile Tyr Ser Thr Val Ala Ser Ser Leu Ala Leu Ala Ile
                500                 505                 510

Met Val Ala Gly Leu Ser Leu Trp Met Cys Ser Asn Gly Ser Leu Gln
                515                 520                 525

Cys Arg Ile Cys Ile
            530

<210> SEQ ID NO 30
<211> LENGTH: 565
<212> TYPE: PRT
<213> ORGANISM: Influenza A virus

<400> SEQUENCE: 30

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Lys His Asn Gly Lys Leu Cys Asp Leu Asp Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Ser His Glu Ala Ser
        130                 135                 140

Leu Gly Val Ser Ser Ala Cys Pro Tyr Gln Gly Lys Ser Ser Phe Phe
```

```
            145                 150                 155                 160
        Arg Asn Val Val Trp Leu Ile Lys Lys Asn Ser Thr Tyr Pro Thr Ile
                        165                 170                 175
        Lys Arg Ser Tyr Asn Asn Thr Asn Gln Glu Asp Leu Leu Val Leu Trp
                        180                 185                 190
        Gly Ile His His Pro Asn Asp Ala Ala Glu Gln Thr Lys Leu Tyr Gln
                        195                 200                 205
        Asn Pro Thr Thr Tyr Ile Ser Val Gly Thr Ser Thr Leu Asn Gln Arg
        210                 215                 220
        Leu Val Pro Arg Ile Ala Thr Arg Ser Lys Val Asn Gly Gln Ser Gly
        225                 230                 235                 240
        Arg Met Glu Phe Phe Trp Thr Ile Leu Lys Pro Asn Asp Ala Ile Asn
                        245                 250                 255
        Phe Glu Ser Asn Gly Asn Phe Ile Ala Pro Glu Tyr Ala Tyr Lys Ile
                        260                 265                 270
        Val Lys Lys Gly Asp Ser Thr Ile Met Lys Ser Glu Leu Glu Tyr Gly
                        275                 280                 285
        Asn Cys Asn Thr Lys Cys Gln Thr Pro Met Gly Ala Ile Asn Ser Ser
        290                 295                 300
        Met Pro Phe His Asn Ile His Pro Leu Thr Ile Gly Glu Cys Pro Lys
        305                 310                 315                 320
        Tyr Val Lys Ser Asn Arg Leu Val Leu Ala Thr Gly Leu Arg Asn Ser
                        325                 330                 335
        Pro Gln Arg Glu Arg Arg Arg Lys Lys Arg Gly Leu Phe Gly Ala Ile
                        340                 345                 350
        Ala Gly Phe Ile Glu Gly Gly Trp Gln Gly Met Val Asp Gly Trp Tyr
                        355                 360                 365
        Gly Tyr His His Ser Asn Glu Gln Gly Ser Gly Tyr Ala Ala Asp Lys
                        370                 375                 380
        Glu Ser Thr Gln Lys Ala Ile Asp Gly Val Thr Asn Lys Val Asn Ser
        385                 390                 395                 400
        Ile Ile Asp Lys Met Asn Thr Gln Phe Glu Ala Val Gly Arg Glu Phe
                        405                 410                 415
        Asn Asn Leu Glu Arg Arg Ile Glu Asn Leu Asn Lys Lys Met Glu Asp
                        420                 425                 430
        Gly Phe Leu Asp Val Trp Thr Tyr Asn Ala Glu Leu Leu Val Leu Met
                        435                 440                 445
        Glu Asn Glu Arg Thr Leu Asp Phe His Asp Ser Asn Val Lys Asn Leu
                        450                 455                 460
        Tyr Asp Lys Val Arg Leu Gln Leu Arg Asp Asn Ala Lys Glu Leu Gly
        465                 470                 475                 480
        Asn Gly Cys Phe Glu Phe Tyr His Lys Cys Asp Asn Glu Cys Met Glu
                        485                 490                 495
        Ser Val Arg Asn Gly Thr Tyr Asp Tyr Pro Gln Tyr Ser Glu Glu Ala
                        500                 505                 510
        Arg Leu Lys Arg Glu Glu Ile Ser Gly Val Lys Leu Glu Ser Ile Gly
                        515                 520                 525
        Ile Tyr Gln Ile Leu Ser Ile Tyr Ser Thr Val Ala Ser Ser Leu Ala
                        530                 535                 540
        Leu Ala Ile Met Val Ala Gly Leu Ser Leu Trp Met Cys Ser Asn Gly
        545                 550                 555                 560
        Ser Leu Gln Cys Arg
                        565
```

<210> SEQ ID NO 31
<211> LENGTH: 122
<212> TYPE: PRT
<213> ORGANISM: Homo sapiens

<400> SEQUENCE: 31

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Ile Trp Val Arg Gln Val Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Val Leu Ser Pro Lys Ser Tyr Tyr Asp Asn Ser Gly Ile Tyr Phe Asp
            100                 105                 110

Phe Trp Gly Lys Gly Thr Leu Val Arg Val
        115                 120

<210> SEQ ID NO 32
<211> LENGTH: 98
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 33
<211> LENGTH: 108
<212> TYPE: PRT
<213> ORGANISM: Homo sapiens

<400> SEQUENCE: 33

Leu Pro Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Tyr Trp Tyr Gln Gln Lys Pro Gly Gln Ala Pro Val Leu Val Val Tyr
        35                  40                  45

Glu Asp Ser Asp Arg Pro Ser Gly Leu Pro Glu Arg Phe Ser Gly Ser
    50                  55                  60

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Trp Val Phe Gly Gly Arg Thr Lys Leu Thr Val Leu
            100                 105
```

<210> SEQ ID NO 34
<211> LENGTH: 96
<212> TYPE: PRT
<213> ORGANISM: Homo sapiens

<400> SEQUENCE: 34

```
Ser Tyr Val Leu Thr Gln Pro Pro Ser Val Ser Val Ala Pro Gly Lys
  1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Ile Tyr
                 35                  40                  45

Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95
```

<210> SEQ ID NO 35
<211> LENGTH: 111
<212> TYPE: PRT
<213> ORGANISM: Homo sapiens

<400> SEQUENCE: 35

```
Gln Ala Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Tyr
                 20                  25                  30

Thr Val Asn Trp Tyr Gln Gln Leu Pro Gly Ser Ala Pro Lys Leu Leu
                 35                  40                  45

Ile Tyr Ser Asn Asn His Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Ala Asp Arg Gln
                 85                  90                  95

Asn Gly Trp Val Phe Gly Gly Gly Thr Lys Leu Thr Val Leu Gly
            100                 105                 110
```

<210> SEQ ID NO 36
<211> LENGTH: 98
<212> TYPE: PRT
<213> ORGANISM: Homo sapiens

<400> SEQUENCE: 36

```
Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
                 20                  25                  30

Thr Val Asn Trp Tyr Gln Gln Leu Pro Gly Thr Ala Pro Lys Leu Leu
                 35                  40                  45
```

```
Ile Tyr Ser Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Ser Leu
             85                  90                  95

Asn Gly
```

<210> SEQ ID NO 37
<211> LENGTH: 122
<212> TYPE: PRT
<213> ORGANISM: Homo sapiens

<400> SEQUENCE: 37

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Pro Phe Ser Ser Tyr
             20                  25                  30

Val Met Ile Trp Val Arg Gln Val Pro Gly Lys Gly Leu Glu Trp Val
         35                  40                  45

Ser Ala Ile Gly Gly Ser Gly Gly Ser Thr Tyr Tyr Ala Asp Ser Val
     50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Asp Asp Thr Ala Val Tyr Tyr Cys
             85                  90                  95

Val Leu Ser Pro Lys Ser Tyr Tyr Asp Asn Ser Gly Ile Tyr Phe Asp
            100                 105                 110

Phe Trp Gly Gln Gly Thr Leu Val Arg Val
            115                 120
```

<210> SEQ ID NO 38
<211> LENGTH: 112
<212> TYPE: PRT
<213> ORGANISM: Homo sapiens

<400> SEQUENCE: 38

```
Asn Phe Met Leu Thr Gln Pro His Ser Val Ser Glu Ser Pro Gly Lys
 1               5                  10                  15

Thr Ile Thr Ile Ser Cys Thr Ala Ser Ser Gly Ser Ile Ala Ser Asn
             20                  25                  30

Tyr Val Gln Trp Tyr Gln Gln Arg Pro Gly Ser Ala Pro Thr Ile Val
         35                  40                  45

Ile Tyr Glu Asp Asn Gln Arg Pro Ser Gly Val Pro Asp Arg Phe Ser
     50                  55                  60

Gly Ser Ile Asp Thr Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Asn
             85                  90                  95

Thr Asn His Trp Val Phe Gly Gly Gly Thr Lys Val Thr Val Leu Gly
            100                 105                 110
```

<210> SEQ ID NO 39
<211> LENGTH: 98
<212> TYPE: PRT
<213> ORGANISM: Homo sapiens

<400> SEQUENCE: 39

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Arg Pro Gly Ser Ser Pro Thr Thr Val
            35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn
```

<210> SEQ ID NO 40
<211> LENGTH: 122
<212> TYPE: PRT
<213> ORGANISM: Homo sapiens

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Ile Trp Val Arg Gln Val Pro Gly Lys Gly Leu Glu Trp Val
            35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Val Leu Ser Pro Lys Ser Tyr Tyr Asp Asn Ser Gly Ile Tyr Phe Asp
                100                 105                 110

Phe Trp Gly Arg Gly Thr Leu Val Arg Val
                115                 120
```

<210> SEQ ID NO 41
<211> LENGTH: 112
<212> TYPE: PRT
<213> ORGANISM: Homo sapiens

<400> SEQUENCE: 41

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Thr Gly Ala Gly
            20                  25                  30

Asn His Val His Trp Tyr Gln Gln Val Ala Gly Ala Ala Pro Lys Leu
            35                  40                  45

Leu Ile Ser Asn Asn Asn Asn Arg Pro Ser Gly Val Pro Asp Arg Phe
    50                  55                  60

Ser Ala Ser Lys Ser Gly Thr Ser Ala Ser Leu Asp Ile Thr Gly Leu
65                  70                  75                  80

Gln Ala Glu Asp Glu Ala Asp Tyr Tyr Cys Gln Ser Tyr Asp Asn Ser
                85                  90                  95

Leu Asn Asp Trp Val Phe Gly Gly Gly Thr Lys Leu Thr Val Leu Gly
```

```
                      100                 105                 110

<210> SEQ ID NO 42
<211> LENGTH: 99
<212> TYPE: PRT
<213> ORGANISM: Homo sapiens

<400> SEQUENCE: 42

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 43
<211> LENGTH: 121
<212> TYPE: PRT
<213> ORGANISM: Homo sapiens

<400> SEQUENCE: 43

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Leu Ser Thr Tyr
                20                  25                  30

Gly Met His Trp Val Arg Gln Ala Ala Gly Lys Gly Leu Glu Trp Val
            35                  40                  45

Ala Val Ser Ser Tyr Asp Gly Arg Asn Glu Tyr Tyr Ala Asp Ser Val
50                  55                  60

Lys Gly Arg Phe Thr Ile Ser Arg Asp Asn Phe Lys Asp Thr Leu Tyr
65                  70                  75                  80

Leu Gln Met Asn Asn Leu Arg Ala Glu Asp Thr Ala Val Tyr Tyr Cys
                85                  90                  95

Ala Lys Glu Val Gly Met Arg Ser Tyr Asp Ser Tyr Gly Met Asp Val
                100                 105                 110

Trp Gly Lys Gly Thr Leu Val Arg Val
            115                 120

<210> SEQ ID NO 44
<211> LENGTH: 98
<212> TYPE: PRT
<213> ORGANISM: Homo sapiens

<400> SEQUENCE: 44

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 45
<211> LENGTH: 108
<212> TYPE: PRT
<213> ORGANISM: Homo sapiens

<400> SEQUENCE: 45

Asp Ile Gln Leu Thr Gln Ser Pro Ser Thr Leu Ser Ala Ser Val Gly
 1               5                  10                  15

Gly Arg Val Thr Ile Thr Cys Arg Ala Ser Gln Ser Ile Gly Pro Trp
                20                  25                  30

Leu Ala Trp Tyr Gln Gln Lys Pro Gly Lys Ala Pro Glu Leu Leu Ile
             35                  40                  45

Tyr Glu Ala Ser Ser Leu Glu Ser Gly Val Pro Ser Arg Phe Ser Gly
         50                  55                  60

Gly Gly Ser Gly Thr Glu Phe Thr Leu Thr Ile Ser Arg Leu Gln Pro
 65                  70                  75                  80

Asp Asp Ile Ala Thr Tyr Tyr Cys Gln Gln Tyr Ser Ser Tyr Pro Trp
                 85                  90                  95

Thr Phe Gly Gln Gly Thr Lys Leu Glu Ile Lys Arg
                100                 105

<210> SEQ ID NO 46
<211> LENGTH: 95
<212> TYPE: PRT
<213> ORGANISM: Homo sapiens

<400> SEQUENCE: 46

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser
                 85                  90                  95

<210> SEQ ID NO 47
<211> LENGTH: 121
<212> TYPE: PRT
<213> ORGANISM: Homo sapiens

<400> SEQUENCE: 47

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
```

```
                35                  40                  45
Ala His Ile Ser Tyr Asp Gly Thr Glu Thr His Tyr Thr Asp Ser Val
 50                  55                  60

Lys Gly Arg Phe Thr Ile Ser Arg Asp Asn Ser Met Glu Thr Ala Tyr
 65                  70                  75                  80

Leu Gln Met Asp Ser Leu Arg Ala Glu Asp Thr Ala Val Tyr Tyr Cys
                 85                  90                  95

Ala Lys Asp Val Ser Leu Arg Ala Tyr Asp His Tyr Gly Met Asp Val
                100                 105                 110

Trp Gly Arg Gly Thr Leu Val Arg Val
                115                 120

<210> SEQ ID NO 48
<211> LENGTH: 109
<212> TYPE: PRT
<213> ORGANISM: Homo sapiens

<400> SEQUENCE: 48

Ser Ser Glu Leu Thr Gln Asp Pro Ala Val Ser Val Ala Leu Gly Gln
  1               5                  10                  15

Thr Val Arg Ile Thr Cys Gln Gly Glu Ser Leu Arg Asn Tyr Tyr Ala
                 20                  25                  30

Asn Trp Tyr Gln Gln Arg Pro Gly Gln Ala Pro Val Leu Val Ile Tyr
                 35                  40                  45

Gly Gly Asn Ser Arg Pro Ser Gly Ile Ala Asp Arg Phe Ser Gly Ser
             50                  55                  60

Ser Ser Gly Ile Thr Ala Ser Leu Thr Ile Thr Gly Ala Gln Ala Glu
 65                  70                  75                  80

Asp Glu Ala Asp Tyr Tyr Cys Asp Ser Arg Asp Ser Ser Asp Asn His
                 85                  90                  95

Arg Val Phe Gly Gly Arg Thr Gln Leu Thr Val Leu Ser
                100                 105

<210> SEQ ID NO 49
<211> LENGTH: 96
<212> TYPE: PRT
<213> ORGANISM: Homo sapiens

<400> SEQUENCE: 49

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
                 20                  25                  30

Ser Trp Tyr Gln Gln Lys Pro Gly Gln Ala Pro Val Leu Val Ile Tyr
                 35                  40                  45

Gly Lys Asn Asn Arg Pro Ser Gly Ile Pro Asp Arg Phe Ser Gly Ser
             50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

<210> SEQ ID NO 50
<211> LENGTH: 121
<212> TYPE: PRT
<213> ORGANISM: Homo sapiens

<400> SEQUENCE: 50
```

```
Gln Val Gln Leu Val Gln Ser Gly Gly Val Val Gln Pro Gly Arg
1               5                   10                  15

Ser Leu Arg Leu Ser Cys Gly Ala Ser Gly Phe Thr Leu Ser Thr Tyr
            20                  25                  30

Gly Met His Trp Val Arg Gln Ala Ala Gly Lys Gly Leu Glu Trp Val
        35                  40                  45

Ala Val Ser Ser Tyr Asp Gly Arg Asn Glu Tyr Tyr Ala Asp Ser Val
    50                  55                  60

Lys Gly Arg Phe Thr Ile Ser Arg Asp Asn Phe Lys Asp Thr Leu Tyr
65                  70                  75                  80

Leu Gln Met Asn Asn Leu Arg Ala Glu Asp Thr Ala Val Tyr Tyr Cys
                85                  90                  95

Ala Lys Glu Val Gly Met Arg Ser Tyr Asp Ser Tyr Gly Met Asp Val
            100                 105                 110

Trp Gly Arg Gly Thr Leu Val Arg Val
            115                 120
```

<210> SEQ ID NO 51
<211> LENGTH: 108
<212> TYPE: PRT
<213> ORGANISM: Homo sapiens

<400> SEQUENCE: 51

```
Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Glu Ala Pro Lys Val Leu Ile
        35                  40                  45

Phe Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Ala
65                  70                  75                  80

Glu Asp Phe Ala Thr Tyr Tyr Cys Gln Gln Ser Asn Asn Phe Pro Tyr
                85                  90                  95

Thr Phe Gly Gln Gly Thr Lys Leu Glu Ile Lys Arg
            100                 105
```

<210> SEQ ID NO 52
<211> LENGTH: 95
<212> TYPE: PRT
<213> ORGANISM: Homo sapiens

<400> SEQUENCE: 52

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95
```

```
<210> SEQ ID NO 53
<211> LENGTH: 121
<212> TYPE: PRT
<213> ORGANISM: Homo sapiens

<400> SEQUENCE: 53

Glu Val Gln Leu Val Glu Ser Gly Gly Val Val Gln Pro Gly Arg
1               5                   10                  15

Thr Leu Arg Leu Ser Cys Ala Ala Ser Gly Phe Thr Phe Thr Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Arg Lys Lys Tyr Tyr Leu Asp Ser Val
        50                  55                  60

Lys Gly Arg Phe Thr Ile Ser Arg Asp Asn Ser Met Glu Thr Ala Tyr
65                  70                  75                  80

Leu Gln Met Asp Ser Leu Arg Pro Glu Asp Thr Ala Val Tyr Tyr Cys
                85                  90                  95

Ala Lys Asp Val Ser Leu Arg Ala Tyr Asp His Tyr Gly Met Asp Val
            100                 105                 110

Trp Gly Gln Gly Thr Leu Val Arg Val
            115                 120

<210> SEQ ID NO 54
<211> LENGTH: 108
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Ser Tyr Ser Thr Pro Phe
                85                  90                  95

Thr Phe Gly Gly Gly Thr Lys Val Asp Ile Lys Arg
            100                 105

<210> SEQ ID NO 55
<211> LENGTH: 95
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60
```

-continued

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro
                 85                  90                  95
```

<210> SEQ ID NO 56
<211> LENGTH: 270
<212> TYPE: PRT
<213> ORGANISM: Homo sapiens

<400> SEQUENCE: 56

```
Met Ala Gln Val Gln Leu Gln Gln Ser Gly Pro Gly Leu Val Lys Pro
  1               5                  10                  15

Ser Glu Thr Leu Ser Leu Thr Cys Ser Val Ser Gly Asp Ser Ile Lys
                 20                  25                  30

Ser Arg Arg Tyr Tyr Trp Ala Trp Ile Arg Gln Pro Pro Gly Lys Gly
             35                  40                  45

Met Glu Phe Ile Gly Arg Leu Ser His Asp Gly Ser Thr Tyr Tyr Thr
 50                  55                  60

Pro Ser Leu Lys Ser Arg Leu Thr Ile Ser Pro Asp Thr Ser Lys Asn
 65                  70                  75                  80

Gln Phe Ser Leu Lys Leu Ser Ser Val Thr Ala Ala Asp Thr Ala Met
                 85                  90                  95

Tyr Tyr Cys Ala Arg Gly Val Tyr Asp Trp Gly Asn Ser Tyr Gln Leu
            100                 105                 110

Asp Val Trp Gly Gln Gly Thr Leu Val Thr Val Ser Ser Gly Gly Gly
            115                 120                 125

Gly Ser Gly Gly Gly Gly Ser Gly Gly Gly Gly Ser Ser Ala Leu Asp
            130                 135                 140

Ile Gln Met Thr Gln Ser Pro Ser Thr Leu Ser Thr Ser Val Gly Asp
145                 150                 155                 160

Arg Val Thr Ile Thr Cys Arg Ala Ser Gln Asn Ile Ser Asn Trp Leu
                165                 170                 175

Ala Trp Tyr Gln Gln Lys Pro Gly Lys Ala Pro Lys Leu Leu Ile Tyr
            180                 185                 190

Lys Ala Ser Ser Leu Glu Ser Gly Val Pro Ser Arg Phe Ser Gly Ser
            195                 200                 205

Gly Ser Gly Thr Glu Phe Thr Leu Thr Ile Ala Ser Leu Gln Pro Asp
            210                 215                 220

Asp Phe Ala Thr Tyr Tyr Cys Gln Gln Tyr Tyr Arg Ser Trp Thr Phe
225                 230                 235                 240

Gly Gln Gly Thr Lys Leu Glu Ile Lys Arg Ala Ala Ala His His His
                245                 250                 255

His His His Gly Glu Gln Lys Leu Ile Ser Glu Glu Asp Leu
            260                 265                 270
```

<210> SEQ ID NO 57
<211> LENGTH: 270
<212> TYPE: PRT
<213> ORGANISM: Homo sapiens
<220> FEATURE:
<221> NAME/KEY: MOD_RES
<222> LOCATION: (267)..(267)
<223> OTHER INFORMATION: Any amino acid

<400> SEQUENCE: 57

```
Met Ala Gln Val Gln Leu Val Gln Ser Gly Ala Glu Val Lys Lys Pro
  1               5                  10                  15
```

Gly Glu Ser Leu Lys Ile Ser Cys Lys Ser Ser Gly Tyr Lys Leu Ser
            20                  25                  30

Ser Tyr Trp Ile Ala Trp Val Arg Gln Val Pro Gly Lys Gly Leu Glu
        35                  40                  45

Trp Val Gly Ile Ile Asp Pro Arg Asp Ser Thr Arg Tyr Ser Pro
 50                  55                  60

Ser Phe Glu Gly Gln Val Thr Ile Ser Ala Asp Lys Ser Ile Asn Thr
 65                  70                  75                  80

Ala Tyr Leu Gln Trp Ser Ser Leu Lys Thr Ala Asp Thr Ala Met Tyr
                85                  90                  95

Phe Cys Ala Arg Gln Ala Asp Gly Tyr Arg Ser Phe Tyr Gly Met Asp
            100                 105                 110

Val Trp Gly Arg Gly Thr Leu Val Thr Val Ser Ser Gly Gly Gly
            115                 120                 125

Ser Gly Gly Gly Gly Ser Gly Gly Gly Gly Ser Ser Ala Leu Asp Ile
            130                 135                 140

Gln Leu Thr Gln Ser Pro Ser Ser Leu Ser Ala Ser Val Gly Asp Arg
145                 150                 155                 160

Val Thr Ile Thr Cys Arg Ala Ser Gln Thr Ile Asn Asn Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
            195                 200                 205

Ser Gly Thr Asp Phe Thr Leu Thr Ile Ser Ser Leu Gln Pro Glu Asp
 210                 215                 220

His Ala Ser Tyr Tyr Cys Gln Gln Ser Tyr Ser Thr Pro Val Thr Phe
225                 230                 235                 240

Gly Gln Gly Thr Arg Leu Glu Ile Lys Arg Ala Ala Ala His His His
                245                 250                 255

His His His Gly Glu Gln Lys Leu Ile Ser Xaa Glu Asp Leu
            260                 265                 270

<210> SEQ ID NO 58
<211> LENGTH: 273
<212> TYPE: PRT
<213> ORGANISM: Homo sapiens
<220> FEATURE:
<221> NAME/KEY: MOD_RES
<222> LOCATION: (273)..(273)
<223> OTHER INFORMATION: Any amino acid

<400> SEQUENCE: 58

Met Ala Gln Met Gln Leu Val Gln Ser Gly Ala Glu Val Lys Lys Pro
 1               5                  10                  15

Gly Ser Ser Val Lys Ile Ser Cys Lys Ala Ser Gly Gly Thr Phe Asn
            20                  25                  30

Lys Tyr Ile Ile Ser Trp Val Arg Gln Ala Pro Gly Gln Gly Leu Glu
        35                  40                  45

Trp Val Gly Arg Ile Val Pro Ile Thr Gly Ile Thr Asn Tyr Ala Gln
 50                  55                  60

Arg Leu Gln Gly Arg Val Thr Ile Ser Ala Asp Lys Ser Thr Asn Thr
 65                  70                  75                  80

Ala Tyr Met Glu Leu Arg Ser Leu Lys Ser Glu Asp Thr Ala Val Tyr
                85                  90                  95

Tyr Cys Ala Arg Asp Gln Gly Asp Leu Trp Pro His Gln Tyr Gln Gly
            100                 105                 110

```
Thr Asp Val Trp Gly Lys Gly Thr Thr Val Thr Val Ser Ser Gly Gly
            115                 120                 125

Gly Gly Ser Gly Gly Gly Ser Gly Gly Gly Ser Ser Ala Glu
        130                 135                 140

Ile Val Leu Thr Gln Ser Pro Leu Ser Leu Pro Val Thr Pro Gly Glu
145                 150                 155                 160

Pro Ala Ser Ile Ser Cys Arg Ser Ser Gln Ser Leu Leu Tyr Ser Asn
                165                 170                 175

Gly Tyr Asn Tyr Leu Asp Trp Tyr Leu Gln Lys Pro Gly Gln Ser Pro
            180                 185                 190

Gln Leu Leu Ile Tyr Leu Gly Ser Asn Arg Ala Ser Gly Val Pro Asp
        195                 200                 205

Arg Phe Ser Gly Ser Gly Ser Gly Thr Asp Phe Thr Leu Lys Ile Ser
    210                 215                 220

Arg Val Glu Ala Glu Asp Val Gly Val Tyr Tyr Cys Met Gln Ala Leu
225                 230                 235                 240

Gln Val Pro His Thr Phe Gly Gln Gly Thr Lys Val Glu Ile Lys Arg
                245                 250                 255

Ala Ala Ala His His His His His Gly Glu Gln Lys Ile Asp Leu
            260                 265                 270

Xaa

<210> SEQ ID NO 59
<211> LENGTH: 269
<212> TYPE: PRT
<213> ORGANISM: Homo sapiens

<400> SEQUENCE: 59

Met Ala Gln Val Gln Leu Gln Gln Ser Gly Gly Gly Val Val Gln Pro
1               5                   10                  15

Gly Arg Ser Leu Arg Leu Ser Cys Thr Thr Ser Gly Phe Ile Phe Lys
            20                  25                  30

Thr Tyr Asp Met His Trp Leu Arg Gln Ala Pro Gly Lys Gly Leu Glu
        35                  40                  45

Trp Val Ala Phe Ile Arg His Asp Gly Arg Asp Ile Lys Tyr Ala Asp
    50                  55                  60

Ser Val Lys Gly Arg Phe Thr Ile Ser Arg Asp Asp Ser Lys Asp Thr
65                  70                  75                  80

Leu Tyr Leu Gln Met Asp Ser Leu Arg Ala Glu Asp Thr Ala Val Tyr
                85                  90                  95

Phe Cys Ala Arg Asn Arg Phe Thr Gly Tyr Asn Tyr Phe Glu His Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Ser Ala Leu Glu Ile Val Met
    130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Arg Tyr Leu Ala Trp
                165                 170                 175

Tyr Gln Gln Lys Pro Gly Gln Ala Pro Arg Leu Leu Ile Tyr Gly Val
            180                 185                 190

Ser Ser Arg Ala Thr Gly Ile Pro Asp Arg Phe Ser Gly Ser Gly Ser
        195                 200                 205
```

```
Gly Thr Asp Phe Thr Leu Thr Ile Ser Arg Leu Glu Pro Glu Asp Phe
        210                 215                 220

Ala Val Tyr Tyr Cys Gln Gln Tyr Ala Ala Ser Pro Glu Thr Phe Gly
225                 230                 235                 240

Gln Gly Thr Lys Val Glu Ile Lys Arg Ala Ala Ala His His His His
                245                 250                 255

His His Gly Glu Gln Lys Leu Ile Ser Glu Glu Asp Leu
            260                 265

<210> SEQ ID NO 60
<211> LENGTH: 269
<212> TYPE: PRT
<213> ORGANISM: Homo sapiens
<220> FEATURE:
<221> NAME/KEY: MOD_RES
<222> LOCATION: (266)..(266)
<223> OTHER INFORMATION: Any amino acid

<400> SEQUENCE: 60

Met Ala Glu Val Gln Leu Val Glu Ser Gly Gly Leu Ala Gln Pro
1               5                   10                  15

Gly Gly Ser Leu Arg Leu Ser Cys Ser Ala Ser Gly Phe Ser Phe Lys
                20                  25                  30

Thr Tyr Asp Met His Trp Val Arg Gln Ala Pro Gly Lys Gly Pro Glu
            35                  40                  45

Trp Ile Ser Lys Ile Asp Tyr Gly Asn Arg Thr Thr Asp Tyr Ala Asp
50                  55                  60

Ser Val Lys Gly Arg Phe Thr Ile Ser Arg Asp Asn Ala Lys Asn Ser
65                  70                  75                  80

Leu Tyr Leu Gln Met Ser Ser Leu Arg Ala Glu Asp Thr Ala Val Tyr
                85                  90                  95

Tyr Cys Ala Arg Thr Arg Phe Ser Gly Tyr Asp Tyr Phe Glu Asp Trp
            100                 105                 110

Gly Lys Gly Thr Leu Val Thr Val Ser Ser Gly Gly Gly Ser Gly
            115                 120                 125

Gly Gly Gly Ser Gly Gly Gly Ser Ser Ala Leu Glu Ile Val Leu
        130                 135                 140

Thr Gln Ser Pro Gly Thr Leu Ser Leu Ser Pro Gly Glu Ser Ala Thr
145                 150                 155                 160

Leu Ser Cys Arg Pro Ser Gln Ser Val Ser Ser Arg Asp Leu Ala Trp
                165                 170                 175

Tyr Gln Gln Lys Pro Gly Gln Ala Pro Arg Leu Leu Ile Tyr Gly Ala
            180                 185                 190

Ser Ser Arg Ala Thr Gly Ile Pro Asp Arg Phe Ser Gly Ser Gly Ser
        195                 200                 205

Gly Thr Glu Phe Thr Leu Thr Ile Thr Arg Leu Glu Pro Glu Asp Phe
        210                 215                 220

Ala Val Tyr Tyr Cys Gln Gln Tyr Gly Arg Ser Pro Leu Thr Phe Gly
225                 230                 235                 240

Gly Gly Thr Lys Val Glu Ile Lys Arg Ala Ala Ala His His His His
                245                 250                 255

His His Gly Glu Gln Lys Leu Ile Ser Xaa Glu Asp Leu
            260                 265

<210> SEQ ID NO 61
<211> LENGTH: 266
<212> TYPE: PRT
<213> ORGANISM: Homo sapiens
```

```
<220> FEATURE:
<221> NAME/KEY: MOD_RES
<222> LOCATION: (263)..(263)
<223> OTHER INFORMATION: Any amino acid

<400> SEQUENCE: 61

Met Ala Glu Val Gln Leu Val Glu Ser Gly Gly Val Val Gln Pro
1               5                   10                  15

Gly Arg Ser Leu Arg Leu Ser Cys Ala Ala Ser Gly Phe Ser Phe
            20                  25                  30

Thr Tyr Asp Met His Trp Val Arg Arg Ala Pro Gly Lys Gly Leu Glu
        35                  40                  45

Trp Val Ala His Ile Arg Phe Asp Gly Ser Lys Thr Ser Tyr Ala Asp
    50                  55                  60

Ser Val Lys Gly Arg Phe Thr Ile Ser Arg Asp Asn Thr Lys Asn Thr
65                  70                  75                  80

Leu Phe Leu Gln Met Asn Ser Leu Arg Gly Glu Asp Thr Ala Ile Tyr
                85                  90                  95

Tyr Cys Ala Arg Val Arg Phe Ser Gly Tyr Asp Tyr Phe Glu Asn Trp
            100                 105                 110

Gly Lys Gly Thr Leu Val Thr Val Ser Ser Gly Gly Gly Ser Gly
        115                 120                 125

Gly Gly Gly Ser Gly Gly Gly Ser Val His Leu Lys Leu Thr Gln
    130                 135                 140

Ser Pro Ala Thr Leu Ser Val Ser Pro Gly Glu Ser Ala Thr Leu Ser
145                 150                 155                 160

Cys Arg Ala Ser Gln Ser Val Arg Ser Tyr Leu Ala Trp Tyr Gln Gln
                165                 170                 175

Lys Pro Gly Gln Ala Pro Arg Leu Leu Ile Tyr Gly Ala Ser Ser Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
    210                 215                 220

Tyr Cys Gln Gln Tyr Gly Ser Ser Pro Val Thr Phe Gly Gln Gly Thr
225                 230                 235                 240

Lys Leu Glu Ile Lys Arg Ala Ala Ala His His His His His His Gly
                245                 250                 255

Glu Gln Lys Leu Ile Ser Xaa Glu Asp Leu
            260                 265

<210> SEQ ID NO 62
<211> LENGTH: 269
<212> TYPE: PRT
<213> ORGANISM: Homo sapiens
<220> FEATURE:
<221> NAME/KEY: MOD_RES
<222> LOCATION: (266)..(267)
<223> OTHER INFORMATION: Any amino acid

<400> SEQUENCE: 62

Met Ala Glu Val Gln Leu Val Glu Ser Gly Gly Gly Val Val Gln Ser
1               5                   10                  15

Gly Gly Ser Leu Arg Leu Ser Cys Ala Ala Ser Gly Phe Thr Phe Ser
            20                  25                  30

Gly Tyr Asp Met His Trp Val Arg Gln Ala Pro Gly Lys Gly Leu Glu
        35                  40                  45

Trp Val Ala Gly Leu Arg Tyr Asp Gly Thr Lys Arg Glu Tyr Ala Asp
```

```
                50                  55                  60
Ser Val Arg Gly Arg Phe Thr Ile Ser Arg Asp Asn Thr Lys Asn Thr
 65                  70                  75                  80

Leu Tyr Leu Gln Met Asp Ser Leu Arg Gly Glu Asp Thr Ala Val Tyr
                 85                  90                  95

Phe Cys Ala Arg Val Arg Phe Ser Gly Tyr Asn Tyr Phe Glu Asn Trp
                100                 105                 110

Gly Lys Gly Thr Thr Val Thr Val Ser Ser Gly Gly Gly Ser Gly
                115                 120                 125

Gly Gly Gly Ser Gly Gly Gly Ser Ala Leu Glu Ile Val Met
            130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Arg Tyr Leu Ala Trp
                165                 170                 175

Tyr Gln Gln Lys Pro Gly Gln Ala Pro Arg Leu Leu Ile Tyr Gly Val
                180                 185                 190

Ser Ser Arg Ala Thr Gly Ile Pro Asp Arg Phe Ser Gly Ser Gly Ser
                195                 200                 205

Gly Thr Asp Phe Thr Leu Thr Ile Ser Arg Leu Glu Pro Glu Asp Phe
            210                 215                 220

Ala Val Tyr Tyr Cys Gln Gln Tyr Ala Ala Ser Pro Glu Thr Phe Gly
225                 230                 235                 240

Gln Gly Thr Lys Val Glu Ile Lys Arg Ala Ala Ala His His His His
                245                 250                 255

His His Gly Glu Gln Lys Leu Ile Ser Xaa Xaa Asn Leu
            260                 265

<210> SEQ ID NO 63
<211> LENGTH: 269
<212> TYPE: PRT
<213> ORGANISM: Homo sapiens

<400> SEQUENCE: 63

Met Ala Glu Val Gln Leu Val Glu Ser Gly Gly Gly Leu Val Lys Pro
 1               5                  10                  15

Gly Gly Ser Leu Arg Leu Ser Cys Ala Ala Ser Gly Phe Ser Phe Ser
                 20                  25                  30

Thr Tyr Asp Met His Trp Val Arg Gln Ala Pro Gly Lys Gly Leu Glu
                 35                  40                  45

Trp Val Ala Gly Leu Arg Tyr Asp Gly Ser Lys Lys Tyr Tyr Ala Asp
 50                  55                  60

Ser Val Lys Gly Arg Phe Thr Ile Ser Arg Asp Asn Thr Lys Asn Thr
 65                  70                  75                  80

Leu Tyr Leu Gln Met Asp Ser Leu Arg Gly Glu Asp Thr Ala Val Tyr
                 85                  90                  95

Tyr Cys Ala Arg Val Arg Phe Ser Gly Tyr Glu Tyr Phe Glu Asn Trp
                100                 105                 110

Gly Gln Gly Thr Leu Val Thr Val Ser Ser Gly Gly Gly Ser Gly
                115                 120                 125

Gly Gly Gly Ser Gly Gly Gly Ser Ala Leu Asp Val Val Met
            130                 135                 140

Thr Gln Ser Pro Ser Thr Leu Ser Ala Ser Val Gly Asp Arg Val Thr
145                 150                 155                 160

Ile Thr Cys Arg Ala Ser Gln Ser Val Ser Thr Trp Leu Ala Trp Tyr
```

```
                165                 170                 175
Gln Gln Lys Pro Gly Lys Ala Pro Lys Leu Leu Ile Tyr Gln Ala Ser
            180                 185                 190
Asn Leu Glu Ser Gly Val Pro Ser Arg Phe Ser Gly Ser Gly Ser Asp
        195                 200                 205
Thr Glu Phe Thr Leu Thr Ile Asn Asn Leu Gln Pro Ala Asp Phe Ala
    210                 215                 220
Thr Tyr Tyr Cys Gln Gln Tyr Asn Thr Tyr Ser Ser Ala Thr Phe Gly
225                 230                 235                 240
Gln Gly Thr Lys Val Glu Ile Lys Arg Ala Ala Ala His His His His
            245                 250                 255
His His Gly Glu Gln Lys Leu Ile Ser Glu Glu Asp Leu
        260                 265

<210> SEQ ID NO 64
<211> LENGTH: 270
<212> TYPE: PRT
<213> ORGANISM: Homo sapiens
<220> FEATURE:
<221> NAME/KEY: MOD_RES
<222> LOCATION: (267)..(267)
<223> OTHER INFORMATION: Any amino acid

<400> SEQUENCE: 64

Met Ala Glu Val Gln Leu Val Glu Ser Gly Gly Gly Val Val Gln Pro
1               5                   10                  15
Gly Arg Ser Leu Arg Leu Ser Cys Ala Ala Ser Gly Phe Ser Phe Ser
            20                  25                  30
Thr Tyr Asp Met His Trp Val Arg Gln Ala Pro Gly Lys Gly Leu Glu
        35                  40                  45
Trp Val Ala His Ile Arg Phe Asp Gly Ser Lys Thr Ser Tyr Ala Asp
    50                  55                  60
Ser Val Lys Gly Arg Phe Thr Ile Ser Arg Asp Asn Thr Lys Asn Thr
65                  70                  75                  80
Leu Phe Leu Gln Met Asn Ser Leu Arg Gly Glu Asp Thr Ala Ile Tyr
                85                  90                  95
Tyr Cys Ala Arg Val Arg Phe Ser Gly Tyr Asp Tyr Phe Glu Asn Trp
            100                 105                 110
Gly Gln Gly Thr Leu Val Thr Val Ser Ser Gly Gly Gly Ser Gly
        115                 120                 125
Gly Gly Gly Ser Gly Gly Gly Ser Ser Ala Leu Glu Ile Val Leu
    130                 135                 140
Thr Gln Ser Pro Gly Thr Leu Ser Leu Ser Pro Gly Glu Arg Ala Thr
145                 150                 155                 160
Leu Ser Cys Arg Ala Ser Gln Ser Val Ser Ser Ser Tyr Leu Ala Trp
                165                 170                 175
Tyr Gln Gln Lys Pro Gly Gln Ala Pro Arg Leu Leu Ile Tyr Gly Ala
            180                 185                 190
Ser Ser Arg Ala Thr Gly Ile Pro Asp Arg Phe Ser Gly Ser Gly Ser
        195                 200                 205
Gly Thr Asp Phe Thr Leu Thr Ile Ser Arg Leu Glu Pro Glu Asp Phe
    210                 215                 220
Ala Val Tyr Tyr Cys Gln Gln Tyr Gly Ser Ser Pro Pro Tyr Thr Phe
225                 230                 235                 240
Gly Gln Gly Thr Lys Leu Glu Ile Lys Arg Ala Ala Ala His His His
            245                 250                 255
```

His His His Gly Glu Gln Lys Leu Ile Ser Xaa Glu Asp Leu
             260                 265                 270

<210> SEQ ID NO 65
<211> LENGTH: 268
<212> TYPE: PRT
<213> ORGANISM: Homo sapiens
<220> FEATURE:
<221> NAME/KEY: MOD_RES
<222> LOCATION: (265)..(265)
<223> OTHER INFORMATION: Any amino acid

<400> SEQUENCE: 65

Met Ala Glu Val Gln Leu Val Glu Ser Gly Gly Asn Val Val Gln Pro
1               5                   10                  15

Gly Arg Ser Leu Arg Leu Ser Cys Ala Ala Ser Gly Leu Ser Phe Ser
            20                  25                  30

Thr Tyr Asp Met His Trp Val Arg Gln Ala Pro Gly Lys Gly Leu Glu
        35                  40                  45

Trp Val Ala Gly Val Arg Tyr Asp Gly Ser Lys Lys Tyr Tyr Thr Glu
    50                  55                  60

Ser Val Arg Gly Arg Phe Thr Ile Ser Arg Asp Asn Thr Lys Asn Thr
65                  70                  75                  80

Leu Phe Leu Gln Met Asp Ser Leu Arg Gly Asp Asp Thr Ala Val Tyr
                85                  90                  95

Tyr Cys Ala Arg Val Arg Phe Ser Gly Tyr Asp Tyr Phe Glu Asn Trp
            100                 105                 110

Gly Lys Gly Thr Leu Val Thr Val Ser Ser Gly Gly Gly Gly Ser Gly
        115                 120                 125

Gly Gly Gly Ser Gly Gly Gly Ser Ser Ala Leu Glu Ile Val Met
    130                 135                 140

Thr Gln Ser Pro Ala Thr Leu Ser Val Ser Pro Gly Glu Arg Ala Thr
145                 150                 155                 160

Leu Ser Cys Arg Ala Ser Gln Ser Val Ser Ser Asn Leu Ala Trp Tyr
                165                 170                 175

Gln Gln Lys Pro Gly Gln Ala Pro Arg Leu Leu Ile Tyr Gly Ala Ser
            180                 185                 190

Thr Arg Ala Thr Gly Ile Pro Ala Arg Phe Ser Gly Ser Gly Ser Gly
        195                 200                 205

Thr Glu Phe Thr Leu Thr Ile Ser Gly Leu Gln Ser Glu Asp Phe Ala
    210                 215                 220

Val Tyr Tyr Cys Gln Gln Tyr Asp Asn Trp Pro Leu Thr Phe Gly Gly
225                 230                 235                 240

Gly Thr Lys Val Glu Ile Lys Arg Ala Ala Ala His His His His
                245                 250                 255

His Gly Glu Gln Lys Leu Ile Ser Xaa Glu Asp Leu
            260                 265

<210> SEQ ID NO 66
<211> LENGTH: 269
<212> TYPE: PRT
<213> ORGANISM: Homo sapiens
<220> FEATURE:
<221> NAME/KEY: MOD_RES
<222> LOCATION: (267)..(267)
<223> OTHER INFORMATION: Any amino acid

<400> SEQUENCE: 66

Met Ala Glu Val Gln Leu Val Glu Ser Gly Gly Gly Val Val Gln Pro
1               5                   10                  15

Gly Arg Ser Leu Arg Leu Ser Cys Ala Ala Ser Gly Phe Ser Phe Ser
            20                  25                  30

Thr Tyr Asp Met His Trp Val Arg Gln Ala Pro Gly Lys Gly Leu Glu
            35                  40                  45

Trp Val Ala Gly Leu Arg Tyr Asp Gly Ser Lys Lys Tyr Tyr Ala Asp
 50                  55                  60

Ser Val Lys Gly Arg Phe Thr Ile Ser Arg Asp Asn Thr Lys Asn Thr
 65                  70                  75                  80

Leu Tyr Leu Gln Met Asp Ser Leu Arg Gly Glu Asp Thr Ala Val Tyr
                85                  90                  95

Tyr Cys Ala Arg Val Arg Phe Ser Gly Tyr Glu Tyr Phe Glu Asn Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ser Ala Leu Glu Ile Val Met
130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Ser Tyr Leu Ala Trp
                165                 170                 175

Tyr Gln His Lys Pro Gly Gln Ala Pro Arg Leu Leu Ile Tyr Gly Ala
            180                 185                 190

Ser Asn Arg Ala Thr Gly Ile Pro Asp Arg Phe Ser Gly Ser Gly Ser
            195                 200                 205

Gly Thr Asp Phe Thr Leu Thr Ile Ser Arg Leu Glu Pro Glu Asp Phe
210                 215                 220

Ala Val Tyr Tyr Cys Gln Gln Tyr Gly Ser Ser Pro Phe Thr Phe Gly
225                 230                 235                 240

Gly Gly Thr Lys Val Glu Ile Lys Arg Ala Ala Ala His His His His
                245                 250                 255

His His Gly Glu Gln Lys Leu Ile Ser Glu Xaa Asp Leu
            260                 265

<210> SEQ ID NO 67
<211> LENGTH: 269
<212> TYPE: PRT
<213> ORGANISM: Homo sapiens
<220> FEATURE:
<221> NAME/KEY: MOD_RES
<222> LOCATION: (266)..(266)
<223> OTHER INFORMATION: Any amino acid

<400> SEQUENCE: 67

Met Ala Glu Val Gln Leu Val Glu Ser Gly Gly Val Val Gln Pro
 1               5                  10                  15

Gly Arg Ser Leu Arg Leu Ser Cys Ala Ala Ser Gly Phe Ser Phe Ser
            20                  25                  30

Thr Tyr Asp Met His Trp Val Arg Gln Ala Pro Gly Lys Gly Leu Glu
            35                  40                  45

Trp Val Ala Gly Leu Arg Tyr Asp Gly Ser Lys Lys Tyr Tyr Ala Asp
 50                  55                  60

Ser Val Lys Gly Arg Phe Thr Ile Ser Arg Asp Asn Thr Lys Asn Thr
 65                  70                  75                  80

Leu Tyr Leu Gln Met Asp Ser Leu Arg Gly Glu Asp Thr Ala Val Tyr
                85                  90                  95

Tyr Cys Ala Arg Val Arg Phe Ser Gly Tyr Glu Tyr Phe Glu Asn Trp

```
            100                 105                 110
Gly Arg Gly Thr Leu Val Thr Val Ser Ser Gly Gly Gly Ser Gly
            115                 120                 125
Gly Gly Gly Ser Gly Gly Gly Ser Ser Ala Leu Glu Ile Val Leu
            130                 135                 140
Thr Gln Ser Pro Gly Thr Leu Ser Leu Ser Pro Gly Glu Arg Val Thr
145                 150                 155                 160
Leu Ser Cys Arg Ala Ser Gln Ser Val Ser Ser Thr Tyr Leu Ala Trp
            165                 170                 175
Tyr Gln Gln Lys Pro Gly Gln Ala Pro Arg Leu Leu Ile Tyr Gly Ala
            180                 185                 190
Ser Ser Arg Ala Thr Gly Ile Pro Asp Arg Phe Ser Gly Ser Gly Ser
            195                 200                 205
Gly Thr Asp Phe Thr Leu Thr Val Thr Arg Leu Glu Pro Glu Asp Phe
            210                 215                 220
Ala Val Tyr Tyr Cys Gln Gln Tyr Ala Ser Ser Pro Leu Thr Phe Gly
225                 230                 235                 240
Gly Gly Thr Lys Val Glu Ile Lys Arg Ala Ala Ala His His His His
            245                 250                 255
His His Gly Glu Gln Lys Leu Ile Ser Xaa Glu Asp Leu
            260                 265

<210> SEQ ID NO 68
<211> LENGTH: 269
<212> TYPE: PRT
<213> ORGANISM: Homo sapiens

<400> SEQUENCE: 68

Met Ala Glu Val Gln Leu Val Glu Thr Gly Gly Gly Val Val Gln Pro
1               5                   10                  15
Gly Arg Ser Leu Arg Leu Ser Cys Ala Ala Ser Gly Leu Ser Phe Ser
            20                  25                  30
Thr Tyr Asp Met His Trp Val Arg Gln Ala Pro Gly Lys Gly Leu Glu
            35                  40                  45
Trp Val Ala Gly Ile Arg Tyr Asp Gly Ser Lys Lys Tyr Tyr Ala Asp
        50                  55                  60
Ser Val Lys Gly Arg Phe Thr Ile Ser Arg Asp Asn Thr Arg Asn Thr
65                  70                  75                  80
Leu Tyr Leu Gln Met Asp Ser Leu Arg Gly Glu Asp Thr Ala Ile Tyr
            85                  90                  95
Tyr Cys Ala Arg Val Arg Phe Ser Gly Tyr Glu Tyr Phe Glu Asn Trp
            100                 105                 110
Gly Arg Gly Thr Leu Val Thr Val Ser Ser Gly Gly Gly Ser Gly
            115                 120                 125
Gly Gly Gly Ser Gly Gly Gly Ser Ser Ala Leu Glu Ile Val Met
            130                 135                 140
Thr Gln Ser Pro Ser Thr Leu Ser Leu Ser Pro Gly Glu Arg Ala Thr
145                 150                 155                 160
Leu Ser Cys Arg Ala Ser Gln Ser Val Ser Ser Tyr Leu Ala Trp
            165                 170                 175
Tyr Gln Gln Lys Pro Gly Gln Ala Pro Arg Leu Leu Ile Tyr Gly Ala
            180                 185                 190
Ser Ser Arg Ala Thr Gly Ile Pro Asp Arg Phe Ser Gly Ser Gly Ser
            195                 200                 205
Gly Thr Asp Phe Thr Leu Thr Ile Ser Arg Leu Glu Pro Glu Asp Phe
```

-continued

```
                210                 215                 220
Ala Val Tyr Tyr Cys Gln Gln Tyr Gly Ser Ser Ser Tyr Thr Phe Gly
225                 230                 235                 240

Gln Gly Thr Lys Leu Glu Ile Lys Arg Ala Ala His His His His
            245                 250                 255

His His Gly Glu Gln Lys Leu Ile Ser Glu Glu Asp Leu
        260                 265

<210> SEQ ID NO 69
<211> LENGTH: 269
<212> TYPE: PRT
<213> ORGANISM: Homo sapiens

<400> SEQUENCE: 69

Met Ala Glu Val Gln Leu Val Glu Ser Gly Gly Gly Leu Val Asn Pro
1               5                   10                  15

Gly Gly Ser Leu Arg Leu Ser Cys Ala Ala Ser Gly Phe Ser Phe Ser
            20                  25                  30

Thr Tyr Asp Met His Trp Val Arg Gln Ala Pro Gly Lys Gly Leu Glu
        35                  40                  45

Trp Val Ala His Ile Arg Phe Asp Gly Ser Lys Thr Ser Tyr Ala Asp
    50                  55                  60

Ser Val Lys Gly Arg Phe Thr Ile Ser Arg Asp Asn Thr Lys Asn Thr
65                  70                  75                  80

Leu Phe Leu Gln Met Asn Ser Leu Arg Gly Glu Asp Thr Ala Ile Tyr
                85                  90                  95

Tyr Cys Ala Arg Val Arg Phe Ser Gly Tyr Asp Tyr Phe Glu Asn Trp
            100                 105                 110

Gly Lys Gly Thr Leu Val Thr Val Ser Gly Gly Gly Gly Ser Gly
        115                 120                 125

Gly Gly Gly Ser Gly Gly Gly Ser Ser Ala Leu Glu Ile Val Met
    130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Ser Tyr Leu Ala Trp
                165                 170                 175

Tyr Gln Gln Lys Pro Gly Gln Ala Pro Arg Leu Leu Ile Tyr Gly Ala
            180                 185                 190

Ser Ser Arg Ala Thr Gly Ile Pro Asp Arg Phe Ser Gly Ser Gly Ser
        195                 200                 205

Gly Thr Asp Phe Thr Leu Thr Ile Ser Arg Leu Glu Pro Glu Asp Phe
    210                 215                 220

Ala Val Tyr Tyr Cys Gln Gln Tyr Gly Ser Ser Pro Gly Thr Phe Gly
225                 230                 235                 240

Gln Gly Thr Lys Val Glu Ile Lys Arg Ala Ala Ala His His His His
            245                 250                 255

His His Gly Glu Gln Lys Leu Ile Ser Glu Glu Asp Leu
        260                 265

<210> SEQ ID NO 70
<211> LENGTH: 270
<212> TYPE: PRT
<213> ORGANISM: Homo sapiens
<220> FEATURE:
<221> NAME/KEY: MOD_RES
<222> LOCATION: (267)..(267)
<223> OTHER INFORMATION: Any amino acid
```

<400> SEQUENCE: 70

```
Leu Ala Glu Val Gln Leu Val Glu Ser Gly Gly Gly Val Val Gln Pro
1               5                   10                  15

Gly Arg Ser Leu Arg Leu Ser Cys Ala Ala Ser Gly Phe Ser Phe Ser
            20                  25                  30

Thr Tyr Asp Met His Trp Val Arg Gln Ala Pro Gly Lys Gly Leu Glu
        35                  40                  45

Trp Val Ala His Ile Arg Phe Asp Gly Ser Lys Thr Ser Tyr Ala Asp
    50                  55                  60

Ser Val Lys Gly Arg Phe Thr Ile Ser Arg Asp Asn Thr Lys Asn Thr
65                  70                  75                  80

Leu Phe Leu Gln Met Asn Ser Leu Arg Ala Glu Asp Thr Ala Ile Tyr
                85                  90                  95

Tyr Cys Ala Arg Val Arg Phe Ser Gly Tyr Asp Tyr Phe Glu Asn Trp
            100                 105                 110

Gly Lys Gly Thr Leu Val Thr Val Ser Ser Gly Gly Gly Ser Gly
        115                 120                 125

Gly Gly Gly Ser Gly Gly Gly Ser Ser Ala Leu Glu Ile Val Leu
    130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Tyr Leu Ala Trp
            165                 170                 175

Tyr Gln Gln Lys Pro Gly Gln Ala Pro Arg Leu Leu Ile Tyr Gly Ala
            180                 185                 190

Ser Ser Arg Ala Thr Gly Ile Pro Asp Arg Phe Ser Gly Ser Gly Ser
            195                 200                 205

Gly Thr Asp Phe Thr Leu Thr Ile Ser Arg Leu Glu Pro Glu Asp Phe
    210                 215                 220

Ala Val Tyr Tyr Cys Gln Gln Tyr Gly Ser Ser Leu Ala Leu Thr Phe
225                 230                 235                 240

Gly Gly Gly Thr Lys Val Glu Ile Lys Arg Ala Ala Ala His His His
            245                 250                 255

His His His Gly Glu Gln Lys Leu Ile Ser Xaa Glu Asp Leu
            260                 265                 270
```

<210> SEQ ID NO 71
<211> LENGTH: 268
<212> TYPE: PRT
<213> ORGANISM: Homo sapiens

<400> SEQUENCE: 71

```
Met Ala Gln Val Gln Leu Val Glu Ser Gly Gly Gly Val Val Gln Pro
1               5                   10                  15

Gly Arg Ser Leu Arg Leu Ser Cys Ala Ala Ser Gly Phe Ser Phe Ser
            20                  25                  30

Thr Tyr Asp Met His Trp Val Arg Gln Ala Pro Gly Lys Gly Leu Glu
        35                  40                  45

Trp Val Ala His Ile Arg Phe Asp Gly Ser Lys Thr Ser Tyr Ala Asp
    50                  55                  60

Ser Val Lys Gly Arg Phe Thr Ile Ser Arg Asp Asn Thr Lys Asn Thr
65                  70                  75                  80

Leu Phe Leu Gln Met Asn Ser Leu Arg Gly Glu Asp Thr Ala Ile Tyr
                85                  90                  95

Tyr Cys Ala Arg Val Arg Phe Ser Gly Tyr Asp Tyr Phe Glu Asn Trp
```

Gly Lys Gly Thr Leu Val Thr Val Ser Ser Gly Gly Gly Ser Gly
            115                 120                 125

Gly Gly Gly Ser Gly Gly Gly Ser Ser Ala Leu Asp Ile Gln Leu
        130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Ser Ser Gly Leu Ala Trp Tyr
                165                 170                 175

Gln Gln Asn Pro Gly Lys Ala Pro Asn Leu Leu Ile Tyr Ala Ala Ser
                180                 185                 190

Asn Leu Gln Ser Gly Val Pro Ser Arg Phe Ser Gly Ser Gly Ser Gly
                195                 200                 205

Thr Asp Phe Thr Leu Thr Ile Ser Ser Leu Gln Pro Glu Asp Phe Ala
210                 215                 220

Thr Tyr Tyr Cys Gln Gln Thr Asn Ser Phe Pro Leu Thr Phe Gly Gly
225                 230                 235                 240

Gly Thr Lys Val Glu Ile Lys Arg Ala Ala Ala His His His His
                245                 250                 255

His Gly Glu Gln Lys Leu Ile Ser Glu Glu Asp Leu
            260                 265

<210> SEQ ID NO 72
<211> LENGTH: 269
<212> TYPE: PRT
<213> ORGANISM: Homo sapiens
<220> FEATURE:
<221> NAME/KEY: MOD_RES
<222> LOCATION: (266)..(266)
<223> OTHER INFORMATION: Any amino acid

<400> SEQUENCE: 72

Met Ala Gln Val Gln Leu Val Glu Ser Gly Gly Gly Val Val Gln Pro
1               5                   10                  15

Gly Arg Ser Leu Arg Leu Ser Cys Ala Ala Ser Gly Phe Ser Phe Ser
            20                  25                  30

Thr Tyr Asp Met His Trp Val Arg Gln Ala Pro Gly Lys Gly Leu Glu
        35                  40                  45

Trp Val Ala His Ile Arg Phe Asp Gly Ser Lys Thr Ser Tyr Ala Asp
    50                  55                  60

Ser Val Lys Gly Arg Phe Thr Ile Ser Arg Asp Asn Thr Lys Asn Thr
65                  70                  75                  80

Leu Phe Leu Gln Met Asn Ser Leu Arg Gly Glu Asp Thr Ala Ile Tyr
                85                  90                  95

Tyr Cys Ala Arg Val Arg Phe Ser Gly Tyr Asp Tyr Phe Glu Asn Trp
            100                 105                 110

Gly Arg Gly Thr Leu Val Thr Val Ser Ser Gly Gly Gly Ser Gly
        115                 120                 125

Gly Gly Gly Ser Gly Gly Gly Ser Ser Ala Leu Glu Ile Val Met
        130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Arg Tyr Leu Ala Trp
                165                 170                 175

Tyr Gln Gln Lys Pro Gly Gln Ala Pro Arg Leu Leu Ile Tyr Gly Val
                180                 185                 190

-continued

```
Ser Ser Arg Ala Thr Gly Ile Pro Asp Arg Phe Ser Gly Ser Gly Ser
            195                 200                 205

Gly Thr Asp Phe Thr Leu Thr Ile Ser Arg Leu Glu Pro Glu Asp Phe
        210                 215                 220

Ala Val Tyr Tyr Cys Gln Gln Tyr Ala Ala Ser Pro Glu Thr Phe Gly
225                 230                 235                 240

Gln Gly Thr Lys Val Glu Ile Lys Arg Ala Ala His His His His
                245                 250                 255

His His Gly Glu Gln Lys Leu Ile Ser Xaa Glu Asp Leu
        260                 265
```

<210> SEQ ID NO 73
<211> LENGTH: 269
<212> TYPE: PRT
<213> ORGANISM: Homo sapiens
<220> FEATURE:
<221> NAME/KEY: MOD_RES
<222> LOCATION: (266)..(266)
<223> OTHER INFORMATION: Any amino acid

<400> SEQUENCE: 73

```
Met Ala Glu Val Gln Leu Val Glu Ser Gly Gly Gly Val Val Gln Pro
1               5                   10                  15

Gly Arg Ser Leu Arg Leu Ser Cys Ala Ala Ser Gly Leu Ser Phe Ser
            20                  25                  30

Thr Tyr Asp Met His Trp Val Arg Gln Ala Pro Gly Lys Gly Leu Glu
        35                  40                  45

Trp Val Ala Gly Ile Arg Tyr Asp Gly Ser Lys Lys Tyr Tyr Ala Asp
    50                  55                  60

Ser Val Lys Gly Arg Phe Thr Ile Ser Arg Asp Asn Thr Arg Asn Thr
65                  70                  75                  80

Leu Tyr Leu Gln Met Asp Ser Leu Arg Gly Glu Asp Thr Ala Ile Tyr
                85                  90                  95

Tyr Cys Ala Arg Val Arg Phe Ser Gly Tyr Glu Tyr Phe Glu Asn Trp
            100                 105                 110

Gly Lys Gly Thr Met Val Thr Val Ser Ser Gly Gly Gly Gly Ser Gly
        115                 120                 125

Gly Gly Gly Ser Gly Gly Gly Ser Ser Ala Leu Glu Ile Val Met
    130                 135                 140

Thr Gln Ser Pro Gly Thr Leu Ser Leu Ser Pro Gly Glu Arg Ala Thr
145                 150                 155                 160

Leu Ser Cys Arg Ala Ser Gln Ser Val Ser Ser Arg Tyr Leu Ala Trp
                165                 170                 175

Tyr Gln Gln Lys Pro Gly Gln Ala Pro Arg Leu Leu Ile Tyr Gly Val
            180                 185                 190

Ser Ser Arg Ala Thr Gly Ile Pro Asp Arg Phe Ser Gly Ser Gly Ser
        195                 200                 205

Gly Thr Asp Phe Thr Leu Thr Ile Ser Arg Leu Glu Pro Glu Asp Phe
    210                 215                 220

Ala Val Tyr Tyr Cys Gln Gln Tyr Ala Ala Ser Pro Glu Thr Phe Gly
225                 230                 235                 240

Gln Gly Thr Lys Val Glu Ile Lys Arg Ala Ala His His His
                245                 250                 255

His His Gly Glu Gln Lys Leu Ile Ser Xaa Glu Asp Leu
        260                 265
```

<210> SEQ ID NO 74

```
<211> LENGTH: 269
<212> TYPE: PRT
<213> ORGANISM: Homo sapiens
<220> FEATURE:
<221> NAME/KEY: MOD_RES
<222> LOCATION: (269)..(269)
<223> OTHER INFORMATION: Any amino acid

<400> SEQUENCE: 74
```

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Leu Ser Phe Pro
            20                  25                  30

Thr Tyr Asp Met His Trp Val Arg Gln Ala Pro Gly Lys Gly Leu Glu
        35                  40                  45

Trp Val Ala His Ile Arg Phe Asp Gly Thr Lys Thr Ser Tyr Gly Asp
    50                  55                  60

Ala Val Arg Gly Arg Phe Thr Ile Ser Arg Asp Asn Thr Lys Asn Thr
65                  70                  75                  80

Leu Tyr Leu Gln Met Asn Arg Leu Arg Gly Glu Asp Thr Ala Ile Tyr
                85                  90                  95

Tyr Cys Ala Arg Val Arg Phe Ser Gly Tyr Asp Tyr Phe Glu Asn Trp
            100                 105                 110

Gly Arg Gly Thr Thr Val Thr Val Ser Ser Gly Gly Gly Ser Gly
            115                 120                 125

Gly Gly Gly Ser Gly Gly Gly Ser Ser Ala Leu Glu Ile Val Met
    130                 135                 140

Thr Gln Ser Pro Ala Thr Leu Ser Val Ser Pro Gly Glu Arg Ala Thr
145                 150                 155                 160

Leu Ser Cys Arg Ala Ser Gln Ser Val Ser Asn Leu Ala Trp Tyr
            165                 170                 175

Gln Gln Lys Pro Gly Gln Ala Pro Arg Leu Leu Ile Tyr Gly Ala Ser
            180                 185                 190

Thr Arg Ala Thr Gly Ile Pro Ala Arg Phe Ser Gly Ser Gly Ser Gly
        195                 200                 205

Thr Glu Phe Thr Leu Thr Ile Ser Gly Leu Gln Ser Glu Asp Phe Ala
    210                 215                 220

Val Tyr Tyr Cys Gln Gln Tyr Asp Asn Trp Pro Leu Thr Phe Gly Gly
225                 230                 235                 240

Gly Thr Lys Val Glu Ile Lys Arg Ala Ala Ala His His His His
                245                 250                 255

His Gly Glu Gln Lys Leu Ile Ser Glu Glu Asp Leu Xaa
            260                 265

```
<210> SEQ ID NO 75
<211> LENGTH: 271
<212> TYPE: PRT
<213> ORGANISM: Homo sapiens
<220> FEATURE:
<221> NAME/KEY: MOD_RES
<222> LOCATION: (268)..(268)
<223> OTHER INFORMATION: Any amino acid

<400> SEQUENCE: 75
```

Met Ala Glu Val Gln Leu Val Glu Thr Gly Gly Gly Val Val Gln Pro
1               5                   10                  15

Gly Arg Ser Leu Arg Leu Ser Cys Ala Ala Ser Gly Phe Ser Phe Ser
            20                  25                  30

Thr Tyr Asp Met His Trp Val Arg Gln Ala Pro Gly Lys Gly Leu Glu

```
                 35                  40                  45
Trp Val Ala Gly Leu Arg Tyr Asp Gly Ser Lys Lys Tyr Tyr Ala Asp
             50                  55                  60

Ser Val Lys Gly Arg Phe Thr Ile Ser Arg Asp Asn Thr Lys Asn Thr
 65                  70                  75                  80

Leu Tyr Leu Gln Met Asp Ser Leu Arg Gly Glu Asp Thr Ala Val Tyr
                 85                  90                  95

Tyr Cys Ala Arg Val Arg Phe Ser Gly Tyr Glu Tyr Phe Glu Asn Trp
                100                 105                 110

Gly Lys Gly Thr Leu Val Thr Val Ser Ser Gly Gly Gly Gly Ser Gly
            115                 120                 125

Gly Gly Gly Ser Gly Gly Gly Ser Ala Gln Ser Ala Leu Thr
            130                 135                 140

Gln Pro Arg Ser Val Ser Gly Ser Pro Gly Gln Ser Val Thr Ile Ser
145                 150                 155                 160

Cys Thr Gly Thr Ser Ser Asp Val Gly Gly Tyr Asn Tyr Val Ser Trp
                165                 170                 175

Tyr Gln Gln His Pro Gly Lys Ala Pro Lys Leu Met Ile Tyr Asp Val
            180                 185                 190

Ser Asn Arg Pro Ser Gly Val Ser Asn Arg Phe Ser Gly Ser Lys Ser
        195                 200                 205

Gly Asn Thr Ala Ser Leu Thr Ile Ser Gly Leu Gln Ala Glu Asp Glu
    210                 215                 220

Ala Asp Tyr Tyr Cys Ser Ser Tyr Thr Ser Ser Ser Thr Leu Val Ile
225                 230                 235                 240

Phe Gly Gly Arg Thr Lys Leu Thr Val Leu Gly Ala Ala Ala His His
                245                 250                 255

His His His His Gly Glu Gln Lys Leu Ile Ser Xaa Glu Asn Cys
            260                 265                 270

<210> SEQ ID NO 76
<211> LENGTH: 277
<212> TYPE: PRT
<213> ORGANISM: Homo sapiens
<220> FEATURE:
<221> NAME/KEY: MOD_RES
<222> LOCATION: (269)..(269)
<223> OTHER INFORMATION: Any amino acid

<400> SEQUENCE: 76

Met Ala Glu Val Gln Leu Val Gln Ser Gly Ala Glu Val Lys Lys Pro
 1               5                  10                  15

Gly Ser Ser Val Lys Val Ser Cys Lys Ala Ser Gly Val Thr Leu Ser
             20                  25                  30

Ile Tyr Ser Met Asn Trp Val Arg Gln Ala Pro Gly Gln Gly Leu Glu
         35                  40                  45

Trp Met Gly Arg Ile Ile Pro Ile Thr Gly Val Pro Asn Tyr Ser Gln
     50                  55                  60

Asn Phe Gln Gly Arg Val Thr Ile Thr Ala Asp Lys Ser Thr Ser Thr
 65                  70                  75                  80

Thr Tyr Met Glu Leu Ser Ser Leu Arg Ser Glu Asp Thr Ala Val Tyr
                 85                  90                  95

Tyr Cys Ala Leu Ser Gly Ala Gly Tyr Asn Tyr Tyr Gly Met Asp Val
            100                 105                 110

Trp Gly Gln Gly Thr Leu Val Thr Val Ser Ser Gly Gly Gly Gly Ser
        115                 120                 125
```

Gly Gly Gly Gly Ser Gly Gly Gly Ala Leu Glu Ile Val Leu Thr Gln
            130             135             140

Ser Pro Leu Ser Leu Pro Val Thr Pro Gly Glu Pro Ala Ser Ile Ser
145             150             155             160

Cys Arg Ser Ser Gln Ser Leu Leu His Ser Asn Gly Tyr Asn Tyr Leu
                165             170             175

Asp Trp Tyr Leu Gln Lys Pro Gly Gln Ser Pro Gln Leu Leu Ile Tyr
            180             185             190

Leu Gly Ser Asn Arg Ala Ser Gly Val Pro Asp Arg Phe Ser Gly Ser
        195             200             205

Gly Ser Gly Thr Asp Phe Thr Leu Lys Ile Ser Arg Val Glu Ala Glu
    210             215             220

Asp Val Gly Val Tyr Tyr Cys Met Gln Ala Leu Gln Thr Pro Leu Thr
225             230             235             240

Phe Gly Gly Gly Thr Lys Val Glu Ile Lys Arg Ala Ala Ala His His
                245             250             255

His His His His Gly Glu Gln Lys Leu Ile Ser Glu Xaa Asn Cys Lys
                260             265             270

Leu Leu Lys Val Val
            275

<210> SEQ ID NO 77
<211> LENGTH: 275
<212> TYPE: PRT
<213> ORGANISM: Homo sapiens
<220> FEATURE:
<221> NAME/KEY: MOD_RES
<222> LOCATION: (271)..(272)
<223> OTHER INFORMATION: Any amino acid
<220> FEATURE:
<221> NAME/KEY: MOD_RES
<222> LOCATION: (275)..(275)
<223> OTHER INFORMATION: Any amino acid

<400> SEQUENCE: 77

Met Ala Glu Val Gln Leu Val Gln Ser Gly Ala Glu Val Lys Lys Pro
1               5                   10                  15

Gly Ser Ser Val Lys Val Ser Cys Lys Ala Ser Gly Val Thr Leu Ser
            20                  25                  30

Ile Tyr Ser Met Asn Trp Val Arg Gln Ala Pro Gly Gln Gly Leu Glu
        35                  40                  45

Trp Met Gly Arg Ile Ile Pro Ile Thr Gly Val Pro Asn Tyr Ser Gln
    50                  55                  60

Asn Phe Gln Gly Arg Val Thr Ile Thr Ala Asp Lys Ser Thr Ser Thr
65                  70                  75                  80

Thr Tyr Met Glu Leu Ser Ser Leu Arg Ser Glu Asp Thr Ala Val Tyr
                85                  90                  95

Tyr Cys Ala Leu Ser Gly Ala Gly Tyr Asn Tyr Tyr Gly Met Asp Val
            100                 105                 110

Trp Gly Lys Gly Thr Leu Val Thr Val Ser Ser Gly Gly Gly Gly Ser
        115                 120                 125

Gly Gly Gly Gly Ser Gly Gly Gly Ser Ala Leu Glu Ile Val
    130             135             140

Leu Thr Gln Ser Pro Leu Ser Leu Pro Val Thr Pro Gly Glu Pro Ala
145             150             155             160

Ser Ile Ser Cys Arg Ser Ser Gln Ser Leu Leu His Ser Asn Gly Tyr
                165             170             175

Asn Tyr Leu Asp Trp Tyr Leu Gln Lys Pro Gly Gln Ser Pro His Leu

```
                        180                 185                 190
Leu Ile Tyr Leu Gly Ser Asn Arg Ala Ser Gly Val Pro Asp Arg Phe
        195                 200                 205

Ser Gly Ser Gly Ser Gly Thr Asp Phe Thr Leu Lys Ile Ser Arg Val
    210                 215                 220

Glu Ala Glu Asp Val Gly Val Tyr Tyr Cys Met Gln Ala Leu Gln Thr
225                 230                 235                 240

Pro Arg Thr Phe Gly Pro Gly Thr Lys Val Glu Ile Lys Arg Ala Ala
            245                 250                 255

Ala His His His His His Gly Glu Gln Lys Leu Ile Ser Xaa Xaa
        260                 265                 270

Asp Leu Xaa
        275

<210> SEQ ID NO 78
<211> LENGTH: 271
<212> TYPE: PRT
<213> ORGANISM: Homo sapiens
<220> FEATURE:
<221> NAME/KEY: MOD_RES
<222> LOCATION: (268)..(268)
<223> OTHER INFORMATION: Any amino acid

<400> SEQUENCE: 78

Met Ala Glu Val Gln Leu Val Glu Ser Gly Gly Gly Leu Val Gln Pro
1               5                   10                  15

Gly Arg Ser Leu Arg Leu Ser Cys Gly Ala Ser Gly Phe Thr Leu Ser
            20                  25                  30

Thr Tyr Gly Met His Trp Val Arg Gln Ala Ala Gly Lys Gly Leu Glu
        35                  40                  45

Trp Val Ala Val Ser Ser Tyr Asp Gly Arg Asn Glu Tyr Tyr Ala Asp
    50                  55                  60

Ser Val Lys Gly Arg Phe Thr Ile Ser Arg Asp Asn Phe Lys Asp Thr
65                  70                  75                  80

Leu Tyr Leu Gln Met Asn Asn Leu Arg Ala Glu Asp Thr Ala Val Tyr
                85                  90                  95

Tyr Cys Ala Lys Glu Val Gly Met Arg Ser Tyr Asp Ser Tyr Gly Met
            100                 105                 110

Asp Val Trp Gly Gln Gly Thr Met Val Thr Val Ser Ser Gly Gly Gly
        115                 120                 125

Gly Ser Gly Gly Gly Gly Ser Gly Gly Gly Gly Ser Ser Ala Leu Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Tyr Thr
225                 230                 235                 240

Phe Gly Gln Gly Thr Lys Val Glu Ile Lys Arg Ala Ala Ala His His
                245                 250                 255
```

```
His His His His Gly Glu Gln Lys Leu Ile Ser Xaa Glu Asp Leu
            260                 265                 270

<210> SEQ ID NO 79
<211> LENGTH: 267
<212> TYPE: PRT
<213> ORGANISM: Homo sapiens
<220> FEATURE:
<221> NAME/KEY: MOD_RES
<222> LOCATION: (223)..(223)
<223> OTHER INFORMATION: Any amino acid
<220> FEATURE:
<221> NAME/KEY: MOD_RES
<222> LOCATION: (225)..(225)
<223> OTHER INFORMATION: Any amino acid
<220> FEATURE:
<221> NAME/KEY: MOD_RES
<222> LOCATION: (252)..(252)
<223> OTHER INFORMATION: Any amino acid

<400> SEQUENCE: 79

Met Ala Gln Val Gln Leu Gln Gln Ser Gly Gly Gly Leu Val Gln Pro
1               5                   10                  15

Gly Gly Ser Leu Arg Leu Ser Cys Thr Ala Ser Gly Phe Thr Phe Ser
            20                  25                  30

Asn Tyr His Met Asn Trp Val Arg Gln Ala Pro Gly Lys Gly Leu Glu
        35                  40                  45

Trp Val Ser His Ile Ser Ser Ser Arg Thr Ile Lys Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Ala Gly Ser Gly Tyr Ser Ser Gly Pro Thr Asp Tyr
            100                 105                 110

Trp Gly Lys Gly Thr Met Val Thr Val Ser Ser Gly Gly Gly Gly Ser
        115                 120                 125

Gly Gly Gly Gly Ser Gly Gly Gly Gly Ser Ser Ala Gln Ser Val Leu
    130                 135                 140

Thr Gln Leu Pro Ser Val Ser Gly Ala Pro Gly Gln Arg Val Thr Ile
145                 150                 155                 160

Ser Cys Thr Gly Ser Ser Ser Asn Ile Gly Ala Gly Tyr Asp Val His
                165                 170                 175

Trp Tyr Gln Gln Leu Pro Gly Thr Ala Pro Lys Leu Leu Ile Tyr Gly
            180                 185                 190

Asn Ser Asn Arg Pro Ser Gly Val Pro Asp Arg Phe Ser Gly Ser Lys
        195                 200                 205

Ser Gly Thr Ser Ala Ser Leu Ala Ile Thr Gly Leu Gln Ala Xaa Asp
    210                 215                 220

Xaa Ala Asp Tyr Tyr Cys Gln Ser Tyr Asp Thr Asn Leu Arg Ala Tyr
225                 230                 235                 240

Val Phe Gly Thr Gly Thr Lys Leu Thr Val Leu Xaa Ala Ala Ala His
                245                 250                 255

His His His His His Gly Lys Gln Asn Ser Gln
            260                 265

<210> SEQ ID NO 80
<211> LENGTH: 275
<212> TYPE: PRT
<213> ORGANISM: Homo sapiens
```

-continued

```
<400> SEQUENCE: 80

Met Ala Glu Val Gln Leu Val Glu Ser Gly Gly Gly Val Val Gln Pro
1               5                   10                  15

Gly Arg Ser Leu Arg Leu Ser Cys Thr Ala Ser Gly Phe Ser Ser Ser
            20                  25                  30

Val Tyr Asp Met His Trp Val Arg Gln Ala Pro Gly Gln Gly Leu Glu
        35                  40                  45

Trp Val Ala Leu Ile Ser His Asp Gly Asn His Lys His Tyr Ala Asp
50                  55                  60

Ser Val Lys Gly Arg Phe Thr Ile Ser Arg Asp Asn Ser Lys Asn Ala
65                  70                  75                  80

Leu Tyr Leu Gln Met Asp Ser Leu Arg Gly Glu Asp Thr Ala Val Tyr
                85                  90                  95

Tyr Cys Ala Arg Asp Arg Phe Gly Arg Ser Gly Ile Lys Leu Lys Val
            100                 105                 110

Thr Tyr Leu Asp Tyr Trp Gly Glu Gly Thr Thr Val Thr Val Ser Ser
        115                 120                 125

Gly Gly Gly Gly Ser Gly Gly Gly Ser Gly Gly Gly Gly Ser Ser
130                 135                 140

Ala Leu Glu Ile Val Leu Thr Gln Ser Pro Ala Ser Leu Ser Leu Ser
145                 150                 155                 160

Pro Gly Glu Arg Ala Thr Leu Ser Cys Arg Ala Ser Glu Ser Ile His
                165                 170                 175

Arg Tyr Leu Ala Trp Tyr Gln Gln Lys Pro Gly Gln Ala Pro Arg Leu
            180                 185                 190

Leu Ile Tyr Asp Thr Ser Asn Arg Ala Thr Gly Ile Pro Ala Arg Phe
        195                 200                 205

Ser Gly Ser Gly Ser Gly Thr Asp Phe Thr Leu Thr Ile Ser Ser Leu
210                 215                 220

Glu Pro Glu Asp Phe Ala Val Tyr Tyr Cys Gln Gln Tyr Asn Ser Trp
225                 230                 235                 240

Pro Pro Ile Thr Phe Gly Gln Gly Thr Arg Leu Glu Ile Lys Arg Ala
                245                 250                 255

Ala Ala His His His His His His Gly Glu Gln Lys Leu Ile Ser Glu
            260                 265                 270

Glu Asp Leu
        275

<210> SEQ ID NO 81
<211> LENGTH: 269
<212> TYPE: PRT
<213> ORGANISM: Homo sapiens
<220> FEATURE:
<221> NAME/KEY: MOD_RES
<222> LOCATION: (268)..(268)
<223> OTHER INFORMATION: Any amino acid

<400> SEQUENCE: 81

Met Ala Gln Val Gln Leu Val Glu Ser Gly Gly Gly Val Val Gln Pro
1               5                   10                  15

Gly Lys Ser Leu Arg Leu Ser Cys Ala Ala Ser Gly Phe Asp Phe Ser
            20                  25                  30

Gly Tyr Gly Met His Trp Val Arg Gln Ala Pro Gly Lys Gly Leu Glu
        35                  40                  45

Trp Val Ala Phe Ile Ser Tyr Asp Ala Ser Asn Gln Tyr Tyr Ala Asp
50                  55                  60
```

```
Ser Val Lys Gly Arg Phe Thr Val Ser Arg Asp Asn Ser Lys Asn Thr
 65                  70                  75                  80

Val Ser Leu Gln Met Ser Ser Leu Lys Thr Asp Asp Thr Ala Val Tyr
                 85                  90                  95

Tyr Cys Ala Lys Asp Phe Ser Trp Ser Gly Ser Ile Asp Ser Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Ser Ala Leu Asp Val Val Met Thr
130                 135                 140

Gln Ser Pro Gly Thr Leu Ser Leu Ser Pro Gly Glu Arg Ala Thr Leu
145                 150                 155                 160

Ser Cys Arg Ala Ser Gln Ser Val Ser Ser Tyr Leu Ala Trp Tyr
                165                 170                 175

Gln Gln Lys Pro Gly Gln Ala Pro Arg Leu Leu Ile Tyr Gly Ala Ser
            180                 185                 190

Ser Arg Ala Thr Gly Ile Pro Asp Arg Phe Ser Gly Ser Gly Ser Gly
            195                 200                 205

Thr Asp Phe Thr Leu Thr Ile Ser Arg Leu Glu Pro Glu Asp Phe Ala
210                 215                 220

Val Tyr Tyr Cys Gln Gln Tyr Gly Ser Ser Leu Ser Leu Thr Phe Gly
225                 230                 235                 240

Gly Gly Thr Lys Val Glu Ile Lys Arg Ala Ala Ala His His His
                245                 250                 255

His His Gly Glu Gln Lys Leu Ile Ser Glu Glu Xaa Leu
            260                 265

<210> SEQ ID NO 82
<211> LENGTH: 274
<212> TYPE: PRT
<213> ORGANISM: Homo sapiens
<220> FEATURE:
<221> NAME/KEY: MOD_RES
<222> LOCATION: (271)..(271)
<223> OTHER INFORMATION: Any amino acid

<400> SEQUENCE: 82

Met Ala Glu Val Gln Leu Val Glu Ser Gly Gly Val Val Gln Pro
1               5                   10                  15

Gly Arg Ser Leu Arg Leu Ser Cys Thr Ala Ser Gly Phe Ser Ser
            20                  25                  30

Val Tyr Asp Met His Trp Val Arg Gln Ala Pro Gly Gln Gly Leu Glu
            35                  40                  45

Trp Val Ala Leu Ile Ser His Asp Gly Asn His Lys His Tyr Ala Asp
50                  55                  60

Ser Val Lys Gly Arg Phe Thr Ile Ser Arg Asp Asn Ser Lys Asn Ala
65                  70                  75                  80

Leu Tyr Leu Gln Met Asp Ser Leu Arg Gly Glu Asp Thr Ala Val Tyr
                85                  90                  95

Tyr Cys Ala Arg Asp Arg Phe Gly Arg Ser Gly Ile Lys Leu Lys Val
            100                 105                 110

Thr Tyr Leu Asp Tyr Trp Gly Lys Gly Thr Leu Val Thr Val Ser Ser
            115                 120                 125

Gly Gly Gly Gly Ser Gly Gly Gly Ser Gly Gly Gly Gly Ser Ser
130                 135                 140

Ala Leu Asp Ile Gln Met Thr Gln Ser Pro Ser Ser Leu Ser Ala Ser
145                 150                 155                 160
```

```
Val Gly Asp Arg Val Thr Ile Thr Cys Arg Ala Ser Gln Asn Ile Ser
            165                 170                 175

Ser Phe Leu Asn Trp Tyr Gln Lys Pro Gly Lys Ala Pro Lys Leu
            180                 185                 190

Leu Ile Tyr Ala Thr Ser Arg Leu Gln Ser Gly Val Pro Ser Arg Phe
            195                 200                 205

Ser Gly Ser Gly Ser Gly Thr Asp Phe Thr Leu Thr Ile Ser Ser Leu
            210                 215                 220

Gln Pro Glu Asp Phe Ala Thr Tyr Tyr Cys Gln Gln Ser Tyr Asn Thr
225                 230                 235                 240

Pro Leu Thr Phe Gly Gly Gly Thr Lys Val Asp Ile Lys Arg Ala Ala
                245                 250                 255

Ala His His His His His His Gly Glu Gln Lys Leu Ile Ser Xaa Glu
                260                 265                 270

Asp Leu

<210> SEQ ID NO 83
<211> LENGTH: 274
<212> TYPE: PRT
<213> ORGANISM: Homo sapiens
<220> FEATURE:
<221> NAME/KEY: MOD_RES
<222> LOCATION: (271)..(271)
<223> OTHER INFORMATION: Any amino acid

<400> SEQUENCE: 83

Met Ala Gln Val Gln Leu Val Glu Ser Gly Gly Gly Val Val Gln Pro
1               5                   10                  15

Gly Arg Ser Leu Arg Leu Ser Cys Ala Ala Ser Gly Phe Thr Ser Ser
            20                  25                  30

Pro Tyr Asp Met His Trp Val Arg Gln Ala Pro Gly Gln Gly Leu Glu
            35                  40                  45

Trp Val Ala Leu Ile Ser His Asp Gly Ser Tyr Lys His Tyr Thr Asp
        50                  55                  60

Ser Val Lys Gly Arg Phe Thr Ile Ser Arg Asp Asn Ser Lys Asn Ala
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Phe Gly Arg Ser Gly Ile Lys Leu Lys Val
            100                 105                 110

Thr Tyr Leu Asp Tyr Trp Gly Lys Gly Thr Leu Val Thr Val Ser Ser
            115                 120                 125

Gly Gly Gly Gly Ser Gly Gly Gly Ser Gly Gly Gly Gly Ser Ser
            130                 135                 140

Ala Leu Glu Ile Val Leu Thr Gln Ser Pro Gly Thr Leu Ser Leu Ser
145                 150                 155                 160

Pro Gly Glu Arg Ala Thr Leu Ser Cys Arg Ala Ser Glu Ser Val Asp
                165                 170                 175

Asn Thr Phe Leu Ala Trp Tyr Gln Gln Lys Pro Gly Gln Ala Pro Arg
            180                 185                 190

Leu Leu Ile Tyr Gly Ala Ser Ser Arg Ala Thr Gly Ile Pro Asp Arg
            195                 200                 205

Phe Ser Gly Gly Gly Ser Gly Thr Asp Phe Leu Thr Ile Ser Arg
            210                 215                 220

Leu Glu Pro Glu Asp Ser Ala Val Tyr Tyr Cys Gln Gln Tyr Gly Asn
225                 230                 235                 240
```

-continued

Ser Leu Asn Phe Gly Gly Gly Thr Lys Leu Glu Ile Lys Arg Ala Ala
            245                 250                 255

Ala His His His His His His Gly Glu Gln Lys Leu Ile Ser Xaa Glu
            260                 265                 270

Asp Leu

<210> SEQ ID NO 84
<211> LENGTH: 274
<212> TYPE: PRT
<213> ORGANISM: Homo sapiens
<220> FEATURE:
<221> NAME/KEY: MOD_RES
<222> LOCATION: (271)..(271)
<223> OTHER INFORMATION: Any amino acid

<400> SEQUENCE: 84

Met Ala Glu Val Gln Leu Val Glu Ser Gly Gly Val Val Gln Pro
1               5                   10                  15

Gly Arg Ser Leu Arg Leu Ser Cys Thr Ala Ser Gly Phe Ser Ser Ser
            20                  25                  30

Val Tyr Asp Met His Trp Val Arg Gln Ala Pro Gly Gln Gly Leu Glu
        35                  40                  45

Trp Val Ala Leu Ile Ser His Asp Gly Asn His Lys His Tyr Ala Asp
    50                  55                  60

Ser Val Lys Gly Arg Phe Thr Ile Ser Arg Asp Asn Ser Lys Asn Ala
65                  70                  75                  80

Leu Tyr Leu Gln Met Asp Ser Leu Arg Gly Glu Asp Thr Ala Val Tyr
                85                  90                  95

Tyr Cys Ala Arg Asp Arg Phe Gly Arg Ser Gly Ile Lys Leu Lys Val
            100                 105                 110

Thr Tyr Leu Asp Tyr Trp Gly Arg Gly Thr Leu Val Thr Val Ser Ser
        115                 120                 125

Gly Gly Gly Gly Ser Gly Gly Gly Ser Gly Gly Gly Gly Ser Ser
    130                 135                 140

Ala Leu Asp Ile Gln Leu Thr Gln Ser Pro Ser Thr Leu Ser Ala Ser
145                 150                 155                 160

Val Gly Asp Arg Val Thr Ile Thr Cys Arg Ala Ser Gln Ser Ile Thr
                165                 170                 175

Asn Leu Leu Ala Trp Tyr Gln Gln Lys Pro Gly Lys Ala Pro Asn Leu
            180                 185                 190

Leu Ile Tyr Lys Thr Ser Thr Leu Gln Ser Gly Val Pro Ser Arg Phe
        195                 200                 205

Ser Gly Ser Gly Ser Gly Thr Glu Phe Thr Leu Thr Ile Ser Ser Leu
    210                 215                 220

Gln Pro Asp Asp Phe Ala Thr Tyr Tyr Cys Gln Gln Tyr His Arg Phe
225                 230                 235                 240

Ser Tyr Ser Phe Gly Gln Gly Thr Lys Val Glu Ile Lys Arg Ala Ala
                245                 250                 255

Ala His His His His His His Gly Glu Gln Lys Leu Ile Ser Xaa Glu
            260                 265                 270

Asn Leu

<210> SEQ ID NO 85
<211> LENGTH: 274
<212> TYPE: PRT
<213> ORGANISM: Homo sapiens
<220> FEATURE:

```
<221> NAME/KEY: MOD_RES
<222> LOCATION: (271)..(271)
<223> OTHER INFORMATION: Any amino acid

<400> SEQUENCE: 85
```

Met Ala Glu Val Gln Leu Val Glu Ser Gly Gly Gly Val Val Gln Pro
1               5                   10                  15

Gly Arg Ser Leu Arg Leu Ser Cys Ala Ala Ser Gly Phe Ser Ser Ser
            20                  25                  30

Val Tyr Asp Met His Trp Val Arg Gln Ala Pro Gly Gln Gly Leu Glu
        35                  40                  45

Trp Val Ala Leu Ile Ser His Asp Gly Asn His Lys His Tyr Thr Asp
50                  55                  60

Ser Val Lys Gly Arg Phe Thr Ile Ser Arg Asp Asn Ser Lys Asn Ala
65                  70                  75                  80

Leu Tyr Leu Gln Met Asn Ser Leu Arg Gly Glu Asp Thr Ala Val Tyr
                85                  90                  95

Tyr Cys Ala Arg Asp Arg Phe Gly Arg Ser Gly Met Lys Leu Lys Val
            100                 105                 110

Thr Tyr Leu Asp Tyr Trp Gly Lys Gly Thr Leu Val Thr Val Ser Ser
        115                 120                 125

Gly Gly Gly Gly Ser Gly Gly Gly Ser Gly Gly Gly Gly Ser Ser
130                 135                 140

Ala Leu Asp Ile Gln Met Thr Gln Ser Pro Ser Ser Leu Ser Ala Ser
145                 150                 155                 160

Val Gly Asp Arg Val Thr Leu Thr Cys Arg Ala Ser Gln Ser Ile Asn
                165                 170                 175

Ala Tyr Leu Asn Trp Tyr Gln Gln Lys Pro Gly Lys Ala Pro Lys Leu
            180                 185                 190

Leu Ile Tyr Thr Ala Ser Ser Leu Gln Ser Gly Val Pro Ser Arg Phe
        195                 200                 205

Ser Gly Ser Gly Ser Gly Thr Asp Phe Thr Leu Thr Ile Ser Arg Leu
210                 215                 220

Gln Pro Glu Asp Phe Ala Thr Tyr Tyr Cys Gln Gln Thr Tyr Ser Ser
225                 230                 235                 240

Pro Leu Thr Phe Gly Gly Gly Thr Lys Val Glu Ile Lys Arg Ala Ala
                245                 250                 255

Ala His His His His His His Gly Glu Gln Lys Leu Ile Ser Xaa Glu
            260                 265                 270

Asp Leu

```
<210> SEQ ID NO 86
<211> LENGTH: 276
<212> TYPE: PRT
<213> ORGANISM: Homo sapiens

<400> SEQUENCE: 86
```

Met Ala Glu Val Gln Leu Val Glu Thr Gly Gly Gly Val Val Gln Pro
1               5                   10                  15

Gly Arg Ser Leu Arg Leu Ser Cys Thr Ala Ser Gly Phe Ser Ser Ser
            20                  25                  30

Val Tyr Asp Met His Trp Val Arg Gln Ala Pro Gly Gln Gly Leu Glu
        35                  40                  45

Trp Val Ala Leu Ile Ser His Asp Gly Asn His Lys His Tyr Ala Asp
50                  55                  60

Ser Val Lys Gly Arg Phe Thr Ile Ser Arg Asp Asn Ser Lys Asn Ala

```
65                  70                  75                  80
Leu Tyr Leu Gln Met Asp Ser Leu Arg Gly Glu Asp Thr Ala Val Tyr
                85                  90                  95

Tyr Cys Ala Arg Asp Arg Phe Gly Arg Ser Gly Ile Lys Leu Lys Val
            100                 105                 110

Thr Tyr Leu Asp Tyr Trp Gly Arg Gly Thr Thr Val Thr Val Ser Ser
        115                 120                 125

Gly Gly Gly Gly Ser Gly Gly Gly Ser Gly Gly Gly Gly Ser Ser Ser
    130                 135                 140

Ala Gln Ser Val Leu Thr Gln Pro Pro Ser Val Ser Ala Ala Pro Gly
145                 150                 155                 160

Gln Lys Val Thr Ile Ser Cys Ser Gly Ser Ser Ser Asn Ile Gly Lys
                165                 170                 175

Asn Tyr Val Ser Trp Tyr Gln Gln Val Pro Gly Thr Ala Pro Lys Leu
            180                 185                 190

Leu Ile Tyr Asp Asn Asn Lys Arg Pro Ser Gly Ile Pro Asp Arg Phe
        195                 200                 205

Ser Gly Ser Lys Ser Gly Thr Ser Ala Thr Leu Gly Ile Thr Gly Leu
    210                 215                 220

Gln Thr Gly Asp Glu Ala Asp Tyr His Cys Gly Thr Trp Asp Ser Ser
225                 230                 235                 240

Leu His Ser Gly Leu Phe Gly Gly Gly Thr Lys Leu Thr Val Leu Gly
                245                 250                 255

Ala Ala Ala His His His His His Gly Glu Gln Lys Leu Ile Ser
            260                 265                 270

Glu Glu Asp Leu
        275

<210> SEQ ID NO 87
<211> LENGTH: 269
<212> TYPE: PRT
<213> ORGANISM: Homo sapiens
<220> FEATURE:
<221> NAME/KEY: MOD_RES
<222> LOCATION: (249)..(249)
<223> OTHER INFORMATION: Any amino acid

<400> SEQUENCE: 87

Met Ala Glu Val Gln Leu Val Glu Ser Gly Gly Asp Leu Val Arg Pro
1               5                   10                  15

Gly Gly Ser Leu Arg Leu Ser Cys Thr Ile Ser Gly Val Thr Phe Asn
            20                  25                  30

Gln Tyr Ala Ile Thr Trp Val Arg Gln Ala Pro Gly Lys Gly Leu Gln
        35                  40                  45

Trp Leu Ser Thr Ile Ala Gly Thr Gly Thr Lys Thr Phe Tyr Ala Asp
    50                  55                  60

Ser Val Lys Gly Arg Phe Thr Met Ser Arg Asp Ser Gly Asn Thr
65                  70                  75                  80

Leu Tyr Leu Gln Met Asn Ser Leu Arg Asp Glu Asp Thr Ala Val Tyr
                85                  90                  95

Tyr Cys Ala Lys Ser Leu Ser Met Arg Tyr Phe Leu Asp Leu Trp Gly
            100                 105                 110

Arg Gly Thr Leu Val Thr Val Ser Ser Gly Gly Gly Ser Gly Gly
        115                 120                 125

Gly Gly Ser Gly Gly Gly Ser Ser Ala His Val Ile Leu Thr Gln
    130                 135                 140
```

```
Pro Pro Ser Ala Ser Gly Thr Pro Gly Gln Arg Val Ile Ile Ser Cys
145                 150                 155                 160

Ser Gly Ser Ser Ser Asn Ile Gly Ser Asn Thr Val Asn Trp Tyr Gln
                165                 170                 175

Gln Leu Pro Gly Thr Ala Pro Lys Leu Leu Ile Tyr Asn Asn Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Gln Ser Glu Asp Glu Ala Asp
210                 215                 220

Tyr Tyr Cys Ala Ala Trp Asp Asp Ser Leu Asn Gly Trp Val Phe Gly
225                 230                 235                 240

Gly Gly Thr Lys Val Thr Val Leu Xaa Ala Ala Ala His His His His
                245                 250                 255

His His Gly Glu Gln Lys Leu Ile Ser Glu Glu Asp Leu
            260                 265
```

<210> SEQ ID NO 88
<211> LENGTH: 271
<212> TYPE: PRT
<213> ORGANISM: Homo sapiens

<400> SEQUENCE: 88

```
Met Ala Gln Val Gln Leu Gln Glu Ser Gly Gly Asp Leu Val Lys Pro
1               5                   10                  15

Gly Gly Ser Leu Arg Leu Ser Cys Val Ala Ser Gly Leu Thr Phe Asn
            20                  25                  30

Ser Tyr Gly Met Ser Trp Val Arg Gln Ala Pro Gly Lys Gly Leu Glu
        35                  40                  45

Trp Val Ser Asp Ile Ser Ala Ser Gly Phe Asn Thr Tyr Tyr Val Asp
    50                  55                  60

Ser Leu Lys Gly Arg Phe Thr Ile Ser Arg Asp Asn Ser Arg Asn Thr
65                  70                  75                  80

Leu Phe Leu Gln Met Asn Asn Leu Arg Asp Glu Asp Thr Ala Ile Tyr
                85                  90                  95

Tyr Cys Ala Lys Asn Gly Gly Asp Tyr Met Gly Ala Tyr Ile Asp Asn
            100                 105                 110

Trp Gly Lys Gly Thr Leu Val Thr Val Ser Ser Gly Gly Gly Gly Ser
        115                 120                 125

Gly Gly Gly Gly Ser Gly Gly Gly Ser Ser Ala Gln Ser Val Leu
130                 135                 140

Thr Gln Pro Pro Ser Val Ser Ala Ala Pro Gly Gln Lys Val Thr Ile
145                 150                 155                 160

Ser Cys Ser Gly Ser Ser Ser Asn Ile Gly Asn Asn Tyr Val Ser Trp
                165                 170                 175

Tyr Gln Gln Leu Pro Gly Thr Ala Pro Lys Leu Leu Ile Tyr Asp Asn
            180                 185                 190

Asn Lys Arg Pro Ser Gly Ile Pro Asp Arg Phe Ser Gly Ser Lys Ser
        195                 200                 205

Gly Thr Ser Ala Thr Leu Gly Ile Thr Gly Leu Gln Thr Gly Asp Glu
    210                 215                 220

Ala Asp Tyr Tyr Cys Gly Thr Trp Asp Ser Ser Leu Ser Ala Gly Val
225                 230                 235                 240

Phe Gly Gly Gly Thr Gln Leu Thr Val Leu Gly Ala Ala Ala His His
                245                 250                 255
```

His His His His Gly Glu Gln Lys Leu Ile Ser Glu Glu Asp Leu
                260                 265                 270

<210> SEQ ID NO 89
<211> LENGTH: 270
<212> TYPE: PRT
<213> ORGANISM: Homo sapiens
<220> FEATURE:
<221> NAME/KEY: MOD_RES
<222> LOCATION: (267)..(267)
<223> OTHER INFORMATION: Any amino acid

<400> SEQUENCE: 89

Met Ala Gln Val Gln Leu Val Gln Ser Gly Ala Glu Val Lys Lys Pro
1               5                   10                  15

Gly Ser Ser Val Lys Val Ser Cys Arg Ala Ser Gly Gly Thr Phe Arg
                20                  25                  30

Ser Tyr Ser Phe Asn Trp Leu Arg Gln Ala Pro Gly Gln Gly Leu Glu
            35                  40                  45

Trp Met Gly Arg Ile Ile Pro Val Val Gly Val Leu Asp Tyr Ala Pro
    50                  55                  60

Lys Phe Gln Ala Arg Val Thr Phe Thr Val Asp Thr Ser Thr Ser Val
65                  70                  75                  80

Gly Tyr Met Asp Leu Asn Gly Leu Thr Pro Glu Asp Thr Ala Val Tyr
                85                  90                  95

Tyr Cys Ala Gly Gly Asp His Val Val Lys Ala Ala Leu Ala Tyr Trp
            100                 105                 110

Gly Gly Gly Thr Thr Val Thr Val Ser Ser Gly Gly Gly Ser Gly
        115                 120                 125

Gly Gly Gly Ser Gly Gly Gly Ser Ser Ala Gln Ser Ala Leu Thr
    130                 135                 140

Gln Pro Ala Ser Glu Ser Gly Ser Pro Gly Gln Ser Ile Thr Ile Ser
145                 150                 155                 160

Cys Thr Gly Thr Ser Thr Asp Val Gly Ala Arg Asn Ser Val Ser Trp
                165                 170                 175

Tyr Gln Gln His Pro Gly Lys Ala Pro Lys Leu Ile Leu Tyr Asp Val
            180                 185                 190

Ser His Arg Pro Ser Gly Val Ser Asn Arg Phe Ser Gly Ser Lys Ser
        195                 200                 205

Gly Asn Thr Ala Ser Leu Thr Ile Ser Gly Leu Gln Ala Glu Asp Glu
    210                 215                 220

Gly Asp Phe Tyr Cys Ser Ser Tyr Thr Thr Ser Asn Asn Leu Val Phe
225                 230                 235                 240

Gly Gly Gly Thr Lys Leu Thr Val Leu Gly Ala Ala Ala His His His
                245                 250                 255

His His His Gly Glu Gln Lys Leu Ile Ser Xaa Glu Asp Leu
                260                 265                 270

<210> SEQ ID NO 90
<211> LENGTH: 270
<212> TYPE: PRT
<213> ORGANISM: Homo sapiens
<220> FEATURE:
<221> NAME/KEY: MOD_RES
<222> LOCATION: (267)..(267)
<223> OTHER INFORMATION: Any amino acid

<400> SEQUENCE: 90

Met Ala Gln Val Gln Leu Gln Gln Ser Gly Pro Gly Leu Val Lys Pro
1               5                   10                  15

Ser Glu Thr Leu Ser Leu Thr Cys Thr Leu Ser Gly Gly Ser Met Glu
            20                  25                  30

Ser His Tyr Trp Ser Trp Ile Arg Gln Pro Pro Gly Lys Gly Leu Glu
            35                  40                  45

Trp Met Gly Arg Val Ser Tyr Ile Gly Ile Ser Asn Tyr Asn Pro Tyr
 50                  55                  60

Leu Lys Asn Arg Val Thr Ile Ser Gln Asp Lys Ser Lys Asn Gln Leu
 65                  70                  75                  80

Ser Leu Arg Leu Asn Ser Val Thr Ala Ala Asp Thr Ala Val Tyr Tyr
            85                  90                  95

Cys Ala Arg His Arg Leu Arg Ser Asp Gln Ala Phe Asp Leu Trp Gly
            100                 105                 110

Lys Gly Thr Leu Val Thr Val Ser Ser Gly Gly Gly Ser Gly Gly
            115                 120                 125

Gly Gly Ser Gly Gly Gly Ser Ser Ala Gln Ser Val Leu Thr Gln
            130                 135                 140

Pro Pro Ser Val Ser Gly Ala Pro Gly Gln Arg Val Thr Ile Ser Cys
145                 150                 155                 160

Thr Gly Ser Ser Ser Asn Ile Gly Ala Gly Tyr Asp Val His Trp Tyr
            165                 170                 175

Gln Gln Leu Pro Gly Thr Ala Pro Lys Leu Leu Ile Tyr Gly Asn Ser
            180                 185                 190

Asn Arg Pro Ser Gly Val Pro Asp Arg Phe Ser Gly Ser Lys Ser Gly
            195                 200                 205

Thr Ser Ala Ser Leu Ala Ile Thr Gly Leu Gln Ala Glu Asp Glu Ala
            210                 215                 220

Asp Tyr Tyr Cys Gln Ser Tyr Asp Ser Ser Leu Ser Gly Ser Val Phe
225                 230                 235                 240

Gly Gly Gly Thr Gln Leu Thr Val Leu Ser Ala Ala Ala His His His
            245                 250                 255

His His His Gly Glu Gln Lys Leu Ile Ser Xaa Glu Asp Leu
            260                 265                 270

<210> SEQ ID NO 91
<211> LENGTH: 269
<212> TYPE: PRT
<213> ORGANISM: Homo sapiens

<400> SEQUENCE: 91

Met Ala Glu Val Gln Leu Val Glu Ser Gly Gly Gly Val Val Gln Pro
 1               5                  10                  15

Gly Arg Ser Leu Arg Leu Ser Cys Thr Ile Ser Gly Val Thr Phe Asn
            20                  25                  30

Gln Tyr Ala Ile Thr Trp Val Arg Gln Ala Pro Gly Lys Gly Leu Gln
            35                  40                  45

Trp Leu Ser Thr Ile Ala Gly Thr Gly Thr Lys Thr Phe Tyr Ala Asp
 50                  55                  60

Ser Val Lys Gly Arg Phe Thr Met Ser Arg Asp Ser Ser Gly Asn Thr
 65                  70                  75                  80

Leu Tyr Leu Gln Met Asn Ser Leu Arg Asp Glu Asp Thr Ala Val Tyr
            85                  90                  95

Tyr Cys Ala Lys Ser Leu Ser Met Arg Tyr Phe Leu Asp Leu Trp Gly
            100                 105                 110

Arg Gly Thr Leu Val Thr Val Ser Ser Gly Gly Gly Gly Ser Gly Gly
            115                 120                 125

```
Gly Gly Ser Gly Gly Gly Ser Ser Ala Leu Pro Glu Leu Thr Gln
        130                 135                 140

Pro Pro Ser Ala Ser Gly Thr Pro Gly Gln Arg Val Thr Ile Ser Cys
145                 150                 155                 160

Ser Gly Ser Ser Ser Asn Ile Gly Ser Asn Thr Val Asn Trp Tyr Gln
                165                 170                 175

Gln Leu Pro Gly Thr Ala Pro Lys Leu Leu Ile Tyr Ser Asn Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Gln Ser Glu Asp Glu Ala Asp
    210                 215                 220

Tyr Tyr Cys Ala Ala Trp Asp Asp Ser Leu Asn Gly Leu Val Phe Gly
225                 230                 235                 240

Gly Gly Thr Lys Leu Thr Val Leu Gly Ala Ala Ala His His His His
            245                 250                 255

His His Gly Glu Gln Lys Leu Ile Ser Glu Glu Asp Leu
        260                 265

<210> SEQ ID NO 92
<211> LENGTH: 269
<212> TYPE: PRT
<213> ORGANISM: Homo sapiens
<220> FEATURE:
<221> NAME/KEY: MOD_RES
<222> LOCATION: (249)..(249)
<223> OTHER INFORMATION: Any amino acid

<400> SEQUENCE: 92

Met Ala Glu Val Gln Leu Val Glu Thr Gly Gly Asp Leu Val Arg Pro
1               5                   10                  15

Gly Gly Ser Leu Arg Leu Ser Cys Thr Ile Ser Gly Val Thr Phe Asn
            20                  25                  30

Gln Tyr Ala Ile Thr Trp Val Arg Gln Ala Pro Gly Lys Gly Leu Gln
        35                  40                  45

Trp Leu Ser Thr Ile Ala Gly Thr Gly Thr Lys Thr Phe Tyr Ala Asp
50                  55                  60

Ser Val Lys Gly Arg Phe Thr Met Ser Arg Asp Ser Gly Asn Thr
65                  70                  75                  80

Leu Tyr Leu Gln Met Asn Ser Leu Arg Asp Glu Asp Thr Ala Val Tyr
            85                  90                  95

Tyr Cys Ala Lys Ser Leu Ser Met Arg Tyr Phe Leu Asp Leu Trp Gly
        100                 105                 110

Gln Gly Thr Met Val Thr Val Ser Ser Gly Gly Gly Ser Gly Gly
    115                 120                 125

Gly Gly Ser Gly Gly Gly Gly Ser Ser Ala Gln Ser Val Leu Thr Gln
        130                 135                 140

Pro Pro Ser Ala Ser Gly Thr Pro Gly Gln Arg Val Thr Ile Ser Cys
145                 150                 155                 160

Ser Gly Ser Ser Ser Asn Ile Gly Ser Asn Thr Val Asn Trp Tyr Gln
                165                 170                 175

Gln Leu Pro Gly Thr Ala Pro Lys Leu Leu Ile Tyr Ser Asn Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Gln Ser Glu Asp Glu Ala Asp
```

```
              210                 215                 220
Tyr Tyr Cys Ala Ala Trp Asp Asp Ser Leu Asn Gly Trp Val Phe Gly
225                 230                 235                 240

Gly Gly Thr Lys Leu Thr Val Leu Xaa Ala Ala His His His His
                245                 250                 255

His His Gly Glu Gln Lys Leu Ile Ser Glu Glu Asp Leu
            260                 265

<210> SEQ ID NO 93
<211> LENGTH: 272
<212> TYPE: PRT
<213> ORGANISM: Homo sapiens
<220> FEATURE:
<221> NAME/KEY: MOD_RES
<222> LOCATION: (252)..(252)
<223> OTHER INFORMATION: Any amino acid
<220> FEATURE:
<221> NAME/KEY: MOD_RES
<222> LOCATION: (269)..(269)
<223> OTHER INFORMATION: Any amino acid

<400> SEQUENCE: 93

Met Ala Gln Val Gln Leu Gln Glu Ser Gly Pro Gly Leu Val Lys Pro
1               5                   10                  15

Ser Glu Thr Leu Ser Leu Thr Cys Ser Val Ser Gly Asp Ala Ile Ser
            20                  25                  30

Asn Gly Tyr Phe Trp Gly Trp Ile Arg Gln Pro Pro Gly Gly Gly Leu
        35                  40                  45

Glu Trp Ile Gly Ser Ile Ser His Arg Gly Ser Thr Tyr Tyr Asn Pro
    50                  55                  60
Ser Leu Lys Ser Arg Val Ser Ile Ser Val Asp Thr Ser Lys Asn Gln
65                  70                  75                  80

Phe Ser Leu Ser Leu Thr Ser Val Thr Ala Ala Asp Thr Ala Val Phe
                85                  90                  95

Tyr Cys Ala Arg Ser Asn Gly Asp Tyr Asp Thr Phe Thr Ala Tyr Tyr
            100                 105                 110

Trp Gly Arg Gly Thr Met Val Thr Val Ser Ser Gly Gly Gly Gly Ser
        115                 120                 125

Gly Gly Gly Gly Ser Gly Gly Gly Ser Ser Ala Gln Ala Val Leu
    130                 135                 140

Thr Gln Pro Pro Ser Val Ser Gly Ala Pro Gly Gln Arg Val Thr Ile
145                 150                 155                 160

Ser Cys Thr Gly Ser Ser Ser Asn Ile Gly Ala Gly Tyr Asp Val His
                165                 170                 175

Trp Tyr Gln Gln Leu Pro Gly Thr Ala Pro Lys Leu Leu Ile Tyr Gly
            180                 185                 190

Asn Ser Asn Arg Pro Ser Gly Val Pro Asp Arg Phe Ser Gly Ser Lys
        195                 200                 205

Ser Gly Thr Ser Ala Ser Leu Ala Ile Thr Gly Leu Gln Ala Glu Asp
    210                 215                 220

Glu Ala Asp Tyr Tyr Cys Gln Ser Tyr Asp Ser Ser Leu Ser Gly Ser
225                 230                 235                 240

Val Phe Gly Gly Gly Thr Lys Val Thr Val Leu Xaa Ala Ala Ala His
                245                 250                 255

His His His His Gly Glu Gln Lys Leu Ile Ser Xaa Glu Asp Leu
            260                 265                 270

<210> SEQ ID NO 94
```

```
<211> LENGTH: 270
<212> TYPE: PRT
<213> ORGANISM: Homo sapiens
<220> FEATURE:
<221> NAME/KEY: MOD_RES
<222> LOCATION: (250)..(250)
<223> OTHER INFORMATION: Any amino acid

<400> SEQUENCE: 94
```

Met Ala Gln Val Gln Leu Gln Glu Ser Gly Pro Gly Leu Leu Lys Pro
1               5                   10                  15

Ser Gln Thr Leu Ser Leu Thr Cys Thr Val Ser Gly Asp Ser Ile Ser
            20                  25                  30

Ser Gly Asp His Tyr Trp Asn Trp Ile Arg Gln Pro Ala Gly Lys Gly
        35                  40                  45

Leu Glu Trp Ile Gly Arg Leu Tyr Thr Asn Gly Ile Thr Asp Tyr Asn
    50                  55                  60

Pro Ser Leu Arg Ser Arg Val Ile Ile Ser Ala Asp Thr Ser Lys Asn
65                  70                  75                  80

Gln Phe Thr Leu Lys Leu Ser Ala Val Thr Ala Ala Asp Thr Ala Val
                85                  90                  95

Tyr Tyr Cys Ala Arg Asp Val Trp Glu Pro Gly Thr Phe Glu His Trp
            100                 105                 110

Gly Lys Gly Thr Met Val Thr Val Ser Ser Gly Gly Gly Ser Gly
        115                 120                 125

Gly Gly Gly Ser Gly Gly Gly Ser Ser Ala Leu Ser Ser Glu Leu
    130                 135                 140

Thr Gln Asp Pro Ala Val Ser Val Ala Leu Gly Gln Thr Val Arg Ile
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Ile Leu Val Ile Tyr Gly Lys Asn Asn
            180                 185                 190

Arg Pro Ser Gly Ile Pro Asp Arg Phe Ser Gly Ser Ser Ser Gly Asn
        195                 200                 205

Thr Ala Ser Leu Thr Ile Thr Gly Ala Gln Ala Glu Asp Glu Ala Asp
    210                 215                 220

Tyr Tyr Cys Asn Ser Arg Asp Ser Asn Gly Asp Val Leu Ser Val Phe
225                 230                 235                 240

Gly Gly Gly Thr Lys Leu Thr Val Leu Xaa Ala Ala Ala His His His
                245                 250                 255

His His His Gly Glu Gln Lys Leu Ile Ser Glu Glu Asp Leu
            260                 265                 270

```
<210> SEQ ID NO 95
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95
```

Ser Thr Tyr Gly Met His Trp Val Ala Val Ser Ser Tyr Asp Gly Arg
1               5                   10                  15

Asn Glu Tyr Ala Lys Glu Val Gly Met Arg Ser Tyr Asp Ser Tyr Gly
            20                  25                  30

Met Asp

```
<210> SEQ ID NO 96
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Thr Ser Tyr Gly Met His Trp Val Ala Val Ile Ser Tyr Asp Gly Arg
1               5                   10                  15

Lys Lys Tyr Ala Lys Asp Val Ser Leu Arg Ala Tyr Asp His Tyr Gly
            20                  25                  30

Met Asp

<210> SEQ ID NO 97
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ser Ser Tyr Gly Met His Trp Val Ala His Ile Ser Tyr Asp Gly Thr
1               5                   10                  15

Glu Thr His Ala Lys Asp Val Ser Leu Arg Ala Tyr Asp His Tyr Gly
            20                  25                  30

Met Asp

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ser Ser Tyr Gly Met His Trp Val Ala Val Ile Ser Tyr Asp Gly Ser
1               5                   10                  15

Asn Lys Tyr Ala Lys
            20

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Tyr Tyr Tyr Tyr Gly Met Asp
1               5

<210> SEQ ID NO 100
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
```

```
<223> OTHER INFORMATION: Ser or Thr
<220> FEATURE:
<221> NAME/KEY: MOD_RES
<222> LOCATION: (10)..(10)
<223> OTHER INFORMATION: Val, His, Asp or Leu
<220> FEATURE:
<221> NAME/KEY: MOD_RES
<222> LOCATION: (11)..(11)
<223> OTHER INFORMATION: Ile or Ser
<220> FEATURE:
<221> NAME/KEY: MOD_RES
<222> LOCATION: (16)..(16)
<223> OTHER INFORMATION: Ser, Arg, Thr or Pro
<220> FEATURE:
<221> NAME/KEY: MOD_RES
<222> LOCATION: (17)..(17)
<223> OTHER INFORMATION: Asn, Lys, Glu or Asp
<220> FEATURE:
<221> NAME/KEY: MOD_RES
<222> LOCATION: (18)..(18)
<223> OTHER INFORMATION: Lys, Glu, Thr or Ala
<220> FEATURE:
<221> NAME/KEY: MOD_RES
<222> LOCATION: (19)..(19)
<223> OTHER INFORMATION: Tyr or His
<220> FEATURE:
<221> NAME/KEY: MOD_RES
<222> LOCATION: (22)..(22)
<223> OTHER INFORMATION: Asp or Glu
<220> FEATURE:
<221> NAME/KEY: MOD_RES
<222> LOCATION: (24)..(24)
<223> OTHER INFORMATION: Gly or Ser
<220> FEATURE:
<221> NAME/KEY: MOD_RES
<222> LOCATION: (25)..(25)
<223> OTHER INFORMATION: Met or Leu
<220> FEATURE:
<221> NAME/KEY: MOD_RES
<222> LOCATION: (27)..(27)
<223> OTHER INFORMATION: Tyr, Ala, Ser or Asp
<220> FEATURE:
<221> NAME/KEY: MOD_RES
<222> LOCATION: (29)..(29)
<223> OTHER INFORMATION: Tyr or Asp
<220> FEATURE:
<221> NAME/KEY: MOD_RES
<222> LOCATION: (30)..(30)
<223> OTHER INFORMATION: Tyr, His, Ser, Pro, Arg or Asn

<400> SEQUENCE: 100

Xaa Xaa Tyr Gly Met His Trp Val Ala Xaa Xaa Ser Tyr Asp Gly Xaa
1               5                   10                  15

Xaa Xaa Xaa Ala Lys Xaa Val Xaa Xaa Arg Xaa Tyr Xaa Xaa Tyr Gly
            20                  25                  30

Met Asp

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asn Ser Trp Leu Ala Trp Tyr Val Leu Phe Gly Ala Ala Ser Ser Leu
1               5                   10                  15

Gln Gln Gln Ser Asn Asn Phe Pro Tyr
            20                  25

<210> SEQ ID NO 102
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Ser Trp Leu Ala Trp Tyr Leu Leu Ile Tyr Ala Ala Ser Ser Leu
1               5                   10                  15

Gln Gln Gln Ala Asn Ser Phe Pro
            20

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (8)..(8)
<223> OTHER INFORMATION: Leu or Val
<220> FEATURE:
<221> NAME/KEY: MOD_RES
<222> LOCATION: (10)..(10)
<223> OTHER INFORMATION: Ile or Phe
<220> FEATURE:
<221> NAME/KEY: MOD_RES
<222> LOCATION: (11)..(11)
<223> OTHER INFORMATION: Tyr, Gly, Cys or Asp
<220> FEATURE:
<221> NAME/KEY: MOD_RES
<222> LOCATION: (20)..(20)
<223> OTHER INFORMATION: Ala or Ser
<220> FEATURE:
<221> NAME/KEY: MOD_RES
<222> LOCATION: (22)..(22)
<223> OTHER INFORMATION: Ser or Asn

<400> SEQUENCE: 103

Xaa Ser Trp Leu Ala Trp Tyr Xaa Leu Xaa Xaa Ala Ala Ser Ser Leu
1               5                   10                  15

Gln Gln Gln Xaa Asn Xaa Phe Pro Tyr
            20                  25

<210> SEQ ID NO 104
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Tyr Tyr Ala Asn Trp Tyr Leu Val Ile Tyr Gly Gly Asn Ser Arg
1               5                   10                  15

Pro Asp Ser Arg Asp Ser Ser Asp Asn His Arg
            20                  25

<210> SEQ ID NO 105
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 105

Ser Tyr Tyr Ala Ser Trp Tyr Leu Val Ile Tyr Gly Lys Asn Asn Arg
1               5                   10                  15

Pro Asn Ser Arg Asp Ser Ser Gly Asn His
            20                  25

<210> SEQ ID NO 106
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (13)..(13)
<223> OTHER INFORMATION: Lys, Gly, Arg or Glu
<220> FEATURE:
<221> NAME/KEY: MOD_RES
<222> LOCATION: (15)..(15)
<223> OTHER INFORMATION: Asn or Ser
<220> FEATURE:
<221> NAME/KEY: MOD_RES
<222> LOCATION: (18)..(18)
<223> OTHER INFORMATION: Asn or Gln
<220> FEATURE:
<221> NAME/KEY: MOD_RES
<222> LOCATION: (24)..(24)
<223> OTHER INFORMATION: Gly or Asp
<220> FEATURE:
<221> NAME/KEY: MOD_RES
<222> LOCATION: (27)..(27)
<223> OTHER INFORMATION: Ala or Arg

<400> SEQUENCE: 106

Xaa Tyr Tyr Ala Xaa Trp Tyr Leu Val Ile Tyr Gly Xaa Asn Xaa Arg
1               5                   10                  15

Pro Xaa Ser Arg Asp Ser Ser Xaa Asn His Xaa
            20                  25
```